US 10,883,096 B2

(12) United States Patent
Rummel et al.

(10) Patent No.: US 10,883,096 B2
(45) Date of Patent: Jan. 5, 2021

(54) CARRIER FOR TARGETING NERVE CELLS

(71) Applicant: IPSEN BIOINNOVATION LIMITED, Abingdon (GB)

(72) Inventors: Andreas Rummel, Hannover (DE); Tanja Weil, Frankfurt am Main (DE); Aleksandrs Gutcaits, Riga (LV)

(73) Assignee: IPSEN BIOINNOVATION LIMITED, Abingdon (GB)

( * ) Notice: Subject to any disclaimer, the term of this patent is extended or adjusted under 35 U.S.C. 154(b) by 0 days.

(21) Appl. No.: 16/220,662

(22) Filed: Dec. 14, 2018

(65) Prior Publication Data

US 2020/0024588 A1 Jan. 23, 2020

Related U.S. Application Data

(60) Division of application No. 15/481,645, filed on Apr. 7, 2017, now Pat. No. 10,266,816, which is a division of application No. 14/451,984, filed on Aug. 5, 2014, now Pat. No. 9,650,622, which is a continuation of application No. 13/867,740, filed on Apr. 22, 2013, now Pat. No. 9,115,350, which is a continuation of application No. 11/919,302, filed as application No. PCT/EP2006/003896 on Apr. 26, 2006, now Pat. No. 8,481,040.

(30) Foreign Application Priority Data

Apr. 26, 2005 (DE) .................. 10 2005 019 302

(51) Int. Cl.
| | |
|---|---|
| *C12N 15/00* | (2006.01) |
| *C12N 9/52* | (2006.01) |
| *C07K 14/33* | (2006.01) |
| *A61K 38/00* | (2006.01) |

(52) U.S. Cl.
CPC ............... *C12N 9/52* (2013.01); *C07K 14/33* (2013.01); *A61K 38/00* (2013.01); *C12Y 304/24069* (2013.01); *Y02A 50/30* (2018.01)

(58) Field of Classification Search
CPC ........................................................ C12N 9/52
See application file for complete search history.

(56) References Cited

U.S. PATENT DOCUMENTS

| | | | |
|---|---|---|---|
| 5,668,255 A | 9/1997 | Murphy | |
| 5,939,070 A | 8/1999 | Johnson et al. | |
| 5,965,406 A | 10/1999 | Murphy et al. | |
| 5,989,545 A | 11/1999 | Foster et al. | |
| 6,022,950 A | 2/2000 | Murphy | |
| 6,203,794 B1 | 3/2001 | Dolly et al. | |
| 6,632,440 B1 | 10/2003 | Quinn et al. | |
| 6,787,517 B1 | 9/2004 | Gil et al. | |
| 7,172,764 B2 | 2/2007 | Li et al. | |
| 7,214,787 B1 | 5/2007 | Smith et al. | |
| 7,273,722 B2 | 9/2007 | Lin et al. | |
| 7,341,843 B2 | 3/2008 | Atassi | |
| 7,368,532 B2 | 5/2008 | Shone et al. | |
| 7,456,272 B2 | 11/2008 | Lin et al. | |
| 7,514,088 B2 | 4/2009 | Steward et al. | |
| 7,556,817 B2 | 7/2009 | Steward et al. | |
| 7,563,874 B2 | 7/2009 | Marks et al. | |
| 7,628,992 B1 | 12/2009 | Dolly et al. | |
| 7,713,737 B2 | 5/2010 | Mrsny | |
| 7,786,285 B2 | 8/2010 | Smith et al. | |
| 8,128,940 B2 | 3/2012 | Steward et al. | |
| 8,293,230 B2 | 10/2012 | Rummel | |
| 8,309,686 B2 | 11/2012 | Lin et al. | |
| 8,445,650 B2 | 5/2013 | Simpson et al. | |
| 8,460,682 B2 | 6/2013 | Steward et al. | |
| 8,476,024 B2 | 7/2013 | Mahrhold et al. | |
| 8,481,040 B2 | 7/2013 | Rummel et al. | |
| 8,623,999 B2 | 1/2014 | Steward et al. | |
| 9,005,628 B2 | 4/2015 | Dolly et al. | |
| 9,650,622 B2 * | 5/2017 | Rummel | ................. A61P 25/24 |
| 2002/0068699 A1 | 6/2002 | Donovan | |
| 2002/0137886 A1 | 9/2002 | Lin et al. | |

(Continued)

FOREIGN PATENT DOCUMENTS

| | | |
|---|---|---|
| AU | 2005281830 B2 | 3/2006 |
| DE | 102004043009.8 | 9/2004 |

(Continued)

OTHER PUBLICATIONS

Binz, T. et al., "Arg362 and Tyr365 of the Botulinum Neurotoxin Type A Light Chain Are Involved in Transition State Stabilization," Biochemistry; 41 :1717-1723 (2002).

(Continued)

*Primary Examiner* — Albert M Navarro
*Assistant Examiner* — Mark Navarro
(74) *Attorney, Agent, or Firm* — Gene J. Yao; Barnes & Thornburg LLP

(57) ABSTRACT

The present invention relates to a transport protein which can be obtained by modifying the heavy chain of the neurotoxin formed by *Clostridium botulinum* wherein (i) the protein binds specifically to nerve cells with a higher or lower affinity as the native neurotoxin; (ii) the protein has an increased or reduced neurotoxicity compared to the native neurotoxin, the neurotoxicity being preferably determined in the hemidiaphragm assay; and/or (iii) the protein comprises a lower affinity against neutralizing antibodies compared to the native neurotoxin. The invention also relates to methods for producing the same and the use thereof in cosmetic and pharmaceutical compositions.

8 Claims, 6 Drawing Sheets

Figure 1:
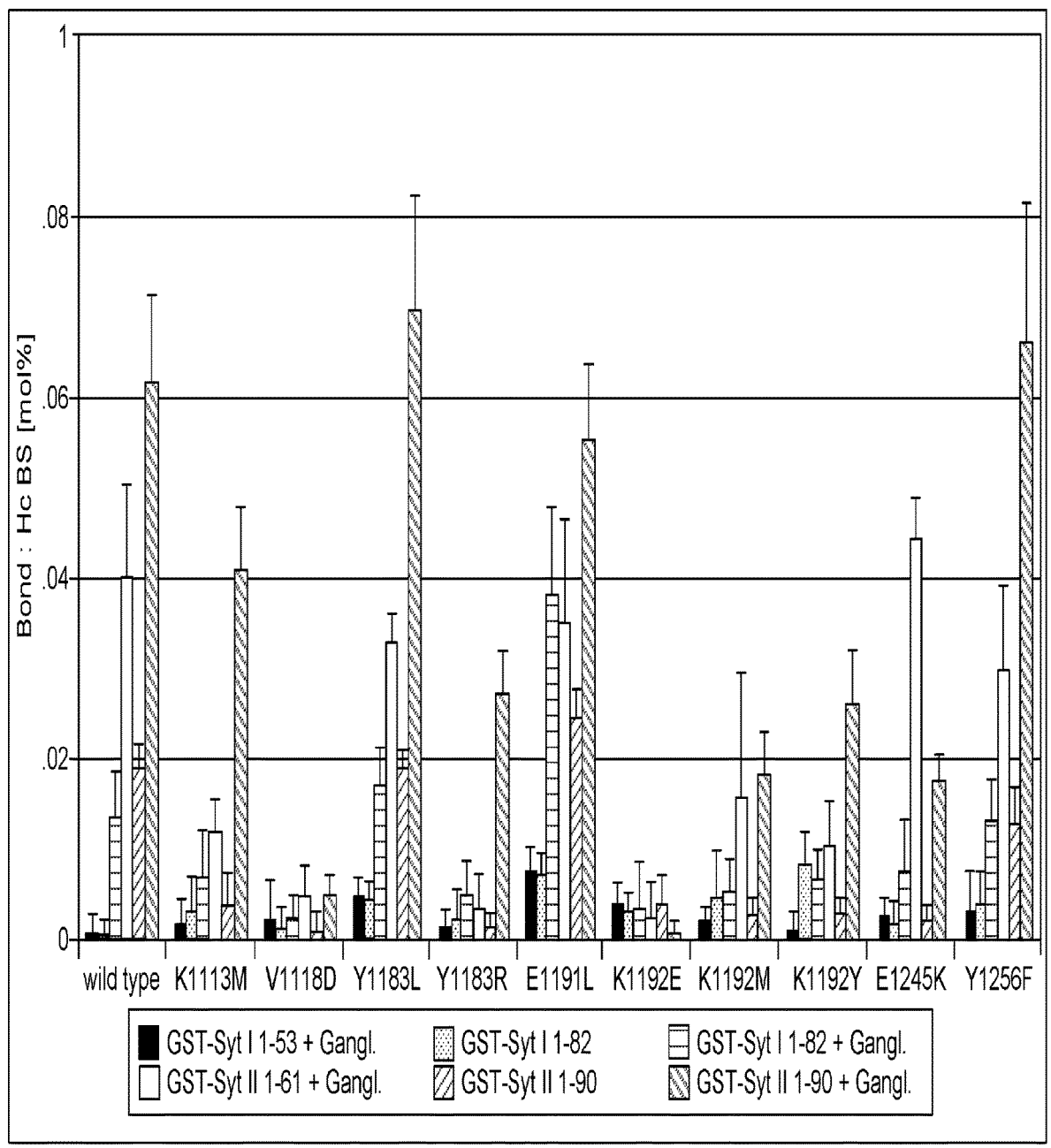

Specification includes a Sequence Listing.

(56) References Cited

U.S. PATENT DOCUMENTS

| | | |
|---|---|---|
| 2003/0049264 A1 | 3/2003 | Foster et al. |
| 2003/0103957 A1 | 6/2003 | McKerracher |
| 2003/0147895 A1 | 8/2003 | Shone et al. |
| 2003/0147921 A1 | 8/2003 | Goodnough et al. |
| 2003/0215468 A1 | 11/2003 | Williams et al. |
| 2004/0013687 A1 | 1/2004 | Simpson et al. |
| 2004/0115727 A1 | 6/2004 | Steward et al. |
| 2004/0175385 A1 | 9/2004 | Marks et al. |
| 2004/0191877 A1 | 9/2004 | Roberts et al. |
| 2004/0191887 A1 | 9/2004 | Chapman et al. |
| 2004/0208889 A1 | 10/2004 | Sutton et al. |
| 2004/0265935 A1 | 12/2004 | Atassi |
| 2005/0129677 A1 | 6/2005 | Li et al. |
| 2006/0204524 A1 | 9/2006 | Ichtchenko et al. |
| 2007/0059326 A1 | 3/2007 | Baldwin et al. |
| 2007/0118934 A1 | 5/2007 | Yu et al. |
| 2007/0258992 A1 | 11/2007 | Atassi |
| 2007/0299008 A1 | 12/2007 | Rummel |
| 2008/0050352 A1 | 2/2008 | Webb et al. |
| 2008/0096248 A1 | 4/2008 | Steward et al. |
| 2008/0102090 A1 | 5/2008 | Panjwani et al. |
| 2009/0053248 A1 | 2/2009 | Simpson et al. |
| 2009/0252722 A1 | 10/2009 | Mahrhold et al. |
| 2009/0311275 A1 | 12/2009 | Rummel et al. |
| 2012/0173140 A1 | 7/2012 | Steward et al. |
| 2013/0116191 A1 | 5/2013 | Rummel |
| 2013/0203148 A1 | 8/2013 | Steward et al. |
| 2013/0315888 A1 | 11/2013 | Rummel et al. |
| 2014/0099294 A1 | 4/2014 | Dolly et al. |
| 2015/0030584 A1 | 1/2015 | Rummel |

FOREIGN PATENT DOCUMENTS

| | | |
|---|---|---|
| GB | 2416692 A | 2/2006 |
| WO | 2000055208 A2 | 9/2000 |
| WO | 2001014570 A1 | 3/2001 |
| WO | 2001058936 | 8/2001 |
| WO | 2002040506 | 5/2002 |
| WO | 2002044199 | 6/2002 |
| WO | 2004009126 A1 | 1/2004 |

OTHER PUBLICATIONS

Bowie et al., Science, 247:1306-1310 (1990).

East, Organization and phylogenie interrelationships of genes encoding components of the botulinum toxin complex in proteolytic Clostridium botulinum types A, B, and F: Evidence of chimeric sequences in the gene encoding the non-toxic nonhemagglutinin component, International Journal of Systematic Bacteriology, 46(6):1105-1112 (1996).

Gimenez, J.A. and DasGupta, B.R., "Botulinum Type A Neurotoxin Digested with Pepsin Yields 132, 97, 72, 45, 42, and 18 kD Fragments," J of Protein Chemistry, 12(3) :351-363 (1993).

Ginalski et al., "Structure-based sequence alignment for the η-trefoll subdomain of the clostridial neurotoxin family provides residue level indormation about the putative ganglioside binding site," FEBS Letters, 482:119-124 (2000).

Goodnough et al , "Development of a delivery vehicle for intracellular transport of botulinum neurotoxin antagonists," FEBS Letters, 513:163-168 (2002).

Goschel, H. et al., "Botulinum A Toxin Therapy: Neutralizing and Nonneutralizing Antibodies—Therapeutic Consequences," Exp. Neural., 147:96-102 (1997).

Greenspan et al., Nature Biotechnology, 7: 936-937 (1999).

Habermann, E. et al., "Tetanus Toxin Blocks the Neuromuscular Transmission in vitro Like Botulinum A Toxin," Naunyn-Schmiedeberq's Arch. Pharmacol., 311 :33-40 (1980).

Herreros, J. et al., "C-terminal Half of Tetanus Toxin Fragment C is Sufficient for Neuronal Binding and Interaction with a Putative Protein Receptor," Biochem. J., 347:199-204 (2000).

Hutson, R.A. et al., "Nucleotide Sequence of the Gene Coding for Non-Proteolytic Clostridium botulinum Type B Neurotoxin: Comparison with Other Clostridial Neurotoxins," Current Microbiology, 28:101-110 (1994).

Ihara et al., "Sequence of the Gene for Clostridium botulinum Type B Neurotoxin Associated with Infant Botulism, Expression of the C-terminal Half of Heavy Chain and its Binding Activity," Biochimica et Biophysica Acta, 1625:19-26 (2003).

Karalewitz et al., "Identification of a Unique Ganglioside Binding Loop within Botulinum Neurotoxins C and D-SA," Biochem., 49(37):8117-8126 (201 O).

Lacy, D.B. et al., "Crystal Structure of Botulinum Neurotoxin Type A and Implications for Toxicity," Nature Structural Biology, 5(1 0):898-902 (1998).

Lough et al., "Identification of a binding site for ganglioside on the receptor binding domain of tetanus toxin," Biochemsitry, 41:13644-13652 (2002).

Maksymowych, A.B. and Simpson, L.L., "Strudural Features of the Botulinum Neurotoxin Molecule that Govern Binding and Transcytosis Across Polarized Human Intestinal Epithelial Cells," J. Pharmacol. and Exp. Therapeutics, 31 0(2):633-641 (2004).

Nippon Salkingaku Zasschl, vol. 57, No. 1, p. 245, abstract 2053 (2002).

Rummel et al., "Identification of the protein receptor binding site of botulinum neurotoxins B and G proves the double-receptor concept," PNAS, 1 04( 1) :359-364 (2007).

Rummel, A. et al., "Synaptotagmins I and II Act as Nerve Cell Receptors for Botulinum Neurotoxin G," J. Biol. Chem., 279(29):30865-30870 (2004).

Rummel, A., et al., "The Hcc-domain of Botulinum Neurotoxins A and B Exhibits a Singular Ganglioside Binding Site Displaying Serotype Specific Carbohydrate Interaction," Molecular Microbiology, 51 (3):631-643 (2004).

Santos-Buelga, J.A. et al., "Characterization of the Genes Encoding the Botulinum Neurotoxin Complex in a Strain of Clostridium botulinum Producing Type Band F Neurotoxins," Current Microbiology, 37:312-318 (1998).

Schiavo et al., "Neurotoxins Affecting Neuroexocytosis," Physiological Revs., 80(2):717-766 (2000).

Shone, C. C. et al., "Inactivation of Clostridium botulinum Type A Neurotoxin by Trypsin and Purification of Two Tryptic Fragments," Eur. J. Biochem., 151 :75-82 (1985).

Smith, T.J. et al., "Sequence Variation within Botulinum Neurotoxin Serotypes Impacts Antibody Binding and Neutralization," Infection and Immunity, 73(9):5450-5457 (2005).

Sutton et al., "Tyrosine-1290 of tetanus neurotoxin plays a key role in its binding to qanqliosides and functional bindinq to neurones," FEBS Letters, 493:45-49 (2001).

Swaminathan et al., "Structural Analysis of the Catalytic and Binding Sites of Clostridium botulinum Neurotoxin," Nature Struct. Biol., 7 (8):693-699 (2000).

Swiss-Prot accession No. Q3LRX9. Clostridium botulinum toxin type A (2009).

Swiss-Prot accession No. O45894, Clostridium botuiinum toxin type A (2009).

Sycha, T. et al , "Botulinum Toxin in the Treatment of Rare Head and Neck Pain Syndromes: A Systematic Review of the Literature," J. Neural., 251(Suppl1):119-I30 (2004).

Tsukamoto et al., "Biding of Clostridium botulinum Type C and D Neurotoxins to Ganglioside and Phospholipid: Novel Insights into the Receptor for Clostridial Neurotoxins," J. Biol. Chem., 280:35164-35171 (2005).

Willems et al, "Sequence of the gene coding for the neurotoxin of Clostridium botulinum type A associated with infant botulism: comparison with other clostridial neurotoxins," Research Microbiology, 144(7):547-556 (1993).

Willems et al., Botulinum neurotoxin type A—Clostridium botulinum, Accession No. 140645 (1993).

Mazuet et al., J. of Clinical Microbiology, 50:4091-4094 (2012).

(56) References Cited

OTHER PUBLICATIONS

Baldwin, M. R. et al, Infection and Immunity, Oct. 2005, vol. 73(10): Characterization of the antibody Response to the Receptor Binding Domain of Botulinum Neurotoxin Serotypes A and E.
Uniprot.org accession No. 045894, 1 page, date Jan. 23, 2002.

* cited by examiner

CARRIER FOR TARGETING NERVE CELLS

This application is a division of U.S. application Ser. No. 15/481,645, filed Apr. 7, 2017, which is a division of U.S. application Ser. No. 14/451,984, now U.S. Pat. No. 9,650,622, filed Aug. 5, 2014, which is a continuation of U.S. application Ser. No. 13/867,740, now U.S. Pat. No. 9,115,350, filed Apr. 22, 2013, which is a continuation of U.S. application Ser. No. 11/919,302, now U.S. Pat. No. 8,481,040, filed Feb. 29, 2008, which is a National Phase filing of International Application No. PCT/EP2006/003896, filed Apr. 26, 2006, which claims priority to German Patent Application No. 102005019302.1, filed Apr. 26, 2005, the contents of each are hereby incorporated by reference in their entireties.

This application contains a Sequence Listing which has been filed electronically in ASCII format and is hereby incorporated by reference in its entirety. Said ASCII copy, created on Feb. 18, 2019, is named 75874-288718_SL.txt and is 313,682 bytes in size.

The present invention relates to a transport protein which binds to neurons with a higher or lower affinity than the neurotoxin formed by *Clostridium botulinum*. The transport protein is preferably absorbed by receptor-mediated endocytosis. This protein is used as a transporting means translocating other chemical substances (e.g. proteases) from the acid endosomal compartment into the cytosol of neurons which are unable physiologically to penetrate into the cytosol of nerve cells through the plasma membrane. The present invention relates, in particular, to the use of a transport protein for the introduction of inhibitors of the release of neurotransmitters.

Nerve cells release transmitter substances by exocytosis. The fusion of the membranes of intracellular vesicles with the plasma membrane is referred to as exocytosis. In the course of this process the vesicular contents is simultaneously released into the synaptic gap. The fusion of the two membranes is regulated by calcium, reacting with the protein synaptotagmin. Jointly with other co-factors synaptotagmin controls the status of three so-called fusion proteins, SNAP-25, synaptobrevin 2 and syntaxin 1A. While syntaxin 1A and synaptobrevin 2 are integrated into the plasma and/or vesicle membrane, SNAP-25 binds only lightly to the plasma membrane. To the extent that the intracellular calcium concentration increases, the three proteins bind to one another, both membranes approaching one another and subsequently fusing together. In the case of cholinergic neurons acetyl choline is released, causing muscle contractions, perspiration and other cholinergically provoked reactions.

The above mentioned fusion proteins are the target molecules (substrates) of the light chain (LC) of the clostridial neurotoxins, formed by the bacteria *C. botulinum, C. butyricum, C. baratii* and *C. tetani*.

The anaerobic, gram-positive bacterium *C. botulinum* produces seven different serotypes of the clostridial neurotoxins. The latter are referred to as the Botulinus neurotoxins (BoNT/A to BoNT/G). Among these, in particular BoNT/A and BoNT/B cause a neuroparalytic disorder in humans and animals, referred to as botulism. The spores of *C. botulinum* can be found in the soil, but may also develop in incorrectly sterilised and sealed home-made food preserves, to which many cases of botulism are attributed.

BoNT/A is the most active of all known biological substances. As little as 5-6 pg of purified BoNT/A represents an MLD (Multiple Lethal Dose). One unit (Engl.: Unit, U) of BoNT/A is defined as the MLD, killing half of the female Swiss Webster mice, each weighing 18-20 g, after intraperitoneal injection. Seven immunologically different BoNTs were characterised. They are denoted as BoNT/A, B, C1, D, E, F and G and may be distinguished by neutralisation with serotype-specific antibodies. The different serotypes of BoNTs differ in affected animal species with regard to severity and duration of the paralysis caused. Thus, with regard to paralysis, BoNT/A is 500 times more potent in rats for example, than BoNT/B. In addition, BoNT/B has proved to be non-toxic in primates at a dosage of 480 U/kg of body weight. The same quantity of BoNT/A corresponds to 12 times the lethal dose of this substance in primates. On the other hand, the duration of paralysis after BoNT/A injection in mice is ten times longer than after injection of BoNT/E.

BoNTs are used for treating neuromuscular disorders, characterised by hyperactivity in skeleton muscles, caused by pathologically overactive peripheral nerves. BoNT/A has been approved by the U.S. Food and Drug Administration for treating blepharospasm, strabismus, hyperhidrosis, wrinkles and hemi-facial spasms. Compared to BoNT/A the remaining BoNT serotypes are evidently less efficacious and manifest a shorter duration of efficacy. Clinical effects of BoNT/A administered peripheral-intramuscularly are usually noticeable within a week. The duration of symptom suppression by one single intramuscular injection of BoNT/A is normally about three to six months.

The clostridial neurotoxins specifically hydrolyse different proteins of the fusion apparatus. BoNT/A, C1 and E break up SNAP-25, while BoNT/B, D, F, G as well as tetanus neurotoxin (TeNT) attack the vesicle-associated membrane protein (VAMP) 2—also referred to as synaptobrevin 2—. BoNT/C1 furthermore breaks up syntaxin 1A.

The *Clostridium* bacteria release the neurotoxins as single-chain polypeptides each having 1251 to 1315 amino acids. Thereafter endogenous proteases split each of these proteins at a defined location into 2 chains each ('nicking'), the two chains however remaining interlinked by a disulphide-bridge. These dual-chain proteins are referred to as holotoxins (see Shone et al. (1985), Eur. J. Biochem. 151, 75-82). The two chains have different functions. While the smaller fragment, the light chain (light chain=LC), represents a $Zn^{2+}$-dependent endoprotease, the larger unit (heavy chain=HC) represents the transporting means of the light chain. By treating the HC with endopeptidases two 50 kDa fragments were brought about (see Gimenez et al. (1993), J. Protein Chem. 12, 351-363). The amino-terminal half ($H_N$-fragment) integrates into membranes at a low pH-value and translocates the LC into the cytosol of the nerve cell. The carboxyl-terminal half ($H_C$-fragment) binds to complex polysialogangliosides, occurring exclusively in nerve cell membranes and to protein receptors identified only partially to date (Halpern et al. (1993), Curr Top Microbial Immunol 195, 221-241). The latter explains the high neuroselectivity of the clostridial neurotoxins. Crystalline structures confirm that BoNT/A disposes of three domains, which may be harmonised by the three steps of the action mechanism (see Lacy et al. (1998), Nat. Struct. Biol. 5, 898-902). Moreover, these data give rise to the conclusion that within the $H_C$-fragment two autonomous subunits (sub-domains) exist of 25 kDa each. The first proof for the existence of the two functional sub-domains was brought about by the amino-terminal ($H_{CN}$) and the carboxyl-terminal half ($H_{CC}$) of the $H_C$-fragment of the TeNT, which were expressed in recombinant form and which revealed that the $H_{CC}$-, but not the $H_{CN}$ domain binds to neurons (see Herreros et al. (2000), Biochem. J. 347, 199-204). At a later stage, a single ganglioside binding site within the $H_{CC}$-domains of BoNT/A and B was localised and characterised (see Rummel et al. (2004), Mol. Microbiol. 51, 631-643). The site for binding the synaptotagmin I and II, identified as protein receptor for BoNT/B and G, could likewise be restricted to the region of the $H_{CC}$-domains of BoNT/B and G (see Rummel et al. (2004), J Biol Chem 279, 30865-70). The document does, however, not disclose the amino acids relevant to the binding pocket of BoNT/B and G.

Under physiological conditions the HC with the $H_C$-fragment binds to neuronal gangliosides, is absorbed inside the cell by receptor-mediated endocytosis and reaches the natural vesicle circulation via the endosomal compartment. In the acid medium of the early endosomes, the $H_N$ fragment penetrates into the vesicle membrane and forms a pore. Each substance (X), linked to the HC via a disulphide bridge, will be split off the HC by intracellular redox systems, gaining access to the disulphide bridge and reducing it. X will ultimately appear in the cytosol.

In the case of the clostridial neurotoxins the HC is the carrier of an LC, splitting its specific substrate in the cytosol in the final step. The cycle of complex formation and dissociation of the fusion proteins is interrupted and the release of acetyl choline is consequently inhibited. As a result thereof, striated muscles are paralysed and sweat glands cease their secretion. The active period of the individual BoNT serotypes differs and depends on the presence of intact LC in the cytosol. As all neurons possess receptors for clostridial neurotoxins, it is not only the release of acetyl choline which may be affected, but potentially also the release of the substance P, of noradrenalin, GABA, glycine, endorphin and other transmitters and hormones.

That the cholinergic transmission is blocked preferentially, may be explained by the fact that the HC in the periphery enters into the neuron. Central synapses are protected by the blood-brain-barrier, which cannot be surmounted by proteins.

In a ligand-receptor study specific amino acid residues were substituted within the $H_{CC}$-domain of BoNT/B and G in order to identify and characterise the binding pocket of the protein receptor in order to thus modify the affinity to the protein receptor. The affinity of the mutated $H_C$-fragments of BoNT/B and G were determined by synaptotagmin in gluthathione-S-transferase-(GST)-pull-down experiments. The HC exhibiting the same mutations was subsequently coupled to LC-B or, respectively LC-G. The potency of these constructs was analysed by means of the isolated nerve-muscle-preparation of the mouse (Hemi-Diaphragm-Assay=HDA). In this preparation the *Nervus phrenicus* is to be found, which consists of cholinergic motor neurons and represents the most important physiological object of clostridial neurotoxins. Subsequently, individual amino acids were substituted in the $H_{CC}$-domain of BoNT/A in a depression, located analogously to the site of the protein-receptor-binding pockets in BoNT/B and G. The full-length BoNT/A single mutants were subsequently likewise analysed by HDA with regard to modified potency, giving indications as to modified ligand-protein-receptor-interactions.

In the more recent past, the BoNT/A complex, also referred to as progenitor toxin A, has been used for treating motor dystonias, as well as for attenuating excessive sympathetic activity (see Benecke et al. (1995), Akt. Neurol. 22, 209ff) and for alleviating pain and migraine (see Sycha et al. (2004), J. Neurol. 251, 19-30). This complex consists of the neurotoxin, various haemagglutinines and a non-toxic, non-haemagglutinating protein. The complex dissociates within a few minutes at physiological pH. The resultant neurotoxin is the sole ingredient of the complex which is therapeutically relevant and brings about an alleviation of the symptoms. Since the underlying neurological illness is not cured, the complex needs to be injected again at intervals of three to four months. Depending on the quantity of the injected foreign protein, some patients develop specific BoNT/A-antibodies. These patients become resistant to the neurotoxin. Once antigen-sensitive cells have recognised the neurotoxin and antibodies have been formed, the relevant memory cells are conserved over years. For this reason it is important to treat the patients with preparations of the highest possible activity at the lowest possible dosage. The preparations should furthermore not contain any further proteins of bacterial origin, since these may act as immuno-adjuvants. Such substances attract macrophages, which recognise both the immuno-adjuvants as well as the neurotoxins, presenting them to the lymphocytes, which thereupon respond by forming immunoglobulins. Consequently, only products of extreme purity, not containing any foreign proteins, should be used for therapy. The resistance of patients to the neurotoxin, viewed at a molecular level, is based predominantly on the presence of neutralising antibodies.

In what follows, the present invention proposes a transport protein (Trapo), which is able to overcome the above described problems of the methods known to date.

This object was obtained by a new transport protein, which can be obtained by modifying the heavy chain of the neurotoxin formed by *Clostridium botulinum*, wherein
(i) the protein binds to nerve cells with a higher or lower affinity than the native neurotoxin;
(ii) the protein has an increased or reduced neurotoxicity compared to the native neurotoxin, the neurotoxicity being preferably determined in the hemidiaphragm assay; and/or,
(iii) compared to the native neurotoxin, the protein exhibits a lower affinity in relation to neutralising antibodies.

According to a preferred embodiment of the present invention, a transport protein is provided which binds to nerve cells with a higher or lower affinity than the native neurotoxin formed by *C. botulinum*.

According to a further preferred embodiment of the present invention, a transport protein is provided which is obtained by modifying the HC of the neurotoxin formed by *C. botulinum*, the protein binding specifically to nerve cells with a higher or lower affinity than the native neurotoxin. The transport protein is preferably absorbed by these cells by endocytosis.

In addition, according to a further preferred embodiment, a transport protein is provided which is obtained by modifying the HC of the neurotoxin formed by *C. botulinum*, the protein, by substituting surface-exposed amino acids, in particular on the ganglioside- and protein-receptor binding pockets of the binding of neutralising antibodies no longer being accessible.

In what follows, terms are defined, which are to be understood in the context of the present application.

"Binding to nerve cells with a higher or lower affinity than native neurotoxin". The native neurotoxin is in this case the native neurotoxin of *C. botulinum*. Preferably, the native neurotoxin is in this context Botulinus neurotoxin A and/or Botulinus neurotoxin B and/or Botulinus neurotoxin G from *C. botulinum*. The Botulinus neurotoxin prepared in recombinant form from *E. coli*, which, inter alia, contains the amino acid sequence identical to the native Botulinus neurotoxin, acts in a pharmacologically identical manner to the native Botulinus neurotoxin and is referred to as recombinant Botulinus neurotoxin wild type. The nerve cells mentioned in this case are cholinergic motor neurons. Preferably, the transport protein binds specifically to the molecules associated with the plasma membrane, transmembrane proteins, synaptic vesicle proteins, a protein of the synaptotagmin family or the synaptic vesicle glycoproteins 2 (SV2), preferably synaptotagmin I and/or synaptotagmin II and/or SV2A, SV2B or SV2C, particularly preferably human synaptotagmin I and/or human synaptotagmin II and/or human SV2A, SV2B or SV2C. Bonding is preferably determined in vitro. Particularly preferably, the determination is performed by using a GST-pull-down-assay, elucidated in detail in the examples.

"the protein has an increased or reduced neurotoxicity compared to the native neurotoxin". The native neurotoxin is in this case the native neurotoxin of *C. botulinum*. Preferably, the native neurotoxin is in this context the Botulinus neurotoxin A and/or Botulinus neurotoxin B and/or Botulinus neurotoxin G from *C. botulinum*. The Botulinus neurotoxin prepared in recombinant form from *E. coli*, which, inter alia, contains the amino acid sequence identical to the native Botulinus neurotoxin, acts in a pharmacologically identical manner to the native Botulinus neurotoxin and is referred to as recombinant Botulinus neurotoxin wild type. The nerve cells mentioned in this case are cholinergic motor neurons. The neurotoxicity is preferably determined with the aid of the Hemi-Diaphragm-Assay (HDA) known in the art. The neurotoxicity of the mutants can preferably be determined as described by Habermann et al., Naunyn Schmiedeberg's Arch. Pharmacol. 311 (1980), 33-40.

"Neutralising antibodies". Neutralising antibodies directed against Botulinus neurotoxin are known (Göschel H, Wohlfarth K, Frevert J, Dengler R, Bigalke H. Botulinum A toxin therapy: neutralizing and nonneutralizing antibodies—therapeutic consequences, Exp. Neurol. 1997 September; 147(1):96-102). It was found that antibodies neutralising neurotoxin interact, in particular, with the active centres such as, for example, the ganglioside- and protein-receptor binding pockets within the $H_{CC}$-domain of the neurotoxin. If the surfaces surrounding the binding pockets are modified in the neurotoxin by amino acid substitutions without negatively impairing their functionality, the neutralising antibodies lose their binding sites and the mutated neurotoxin is no longer neutralised.

The term "modification of the heavy chain of the neurotoxin formed by *C. botulinum*." The amino acid and/or nucleic acid sequence of the heavy chain (HC) of the neurotoxin formed by *C. botulinum* are generally available from publicly accessible databases, for each of the known serotypes A to G (also refer to table 1). Modification includes in this context that at least one amino acid is deleted, added, inserted into the amino acid sequence, or that at least one amino acid of the native neurotoxin is substituted by another naturally occurring or not naturally occurring amino acid and/or that one amino acid in the given amino acid sequence is modified post-translationally. Post-translational modifications include in this context glycosylations, acetylations, acylations, de-aminations, phosphorylisations, isoprenylisations, glycosyl phosphatidyl inositolisations and further modifications known to the person skilled in the art.

The HC of the neurotoxin formed by *C. botulinum* includes three sub-domains, i.e. the amino-terminal 50 kDa-sized translocation domain $H_N$, the 25 kDa $H_{CN}$-domain following thereon, and the carboxyl-terminally situated 25 kDa $H_{CC}$-domain. Together, the $H_{CN}$- and $H_{CC}$-domains are denoted as $H_C$-fragment. The corresponding amino acid sections of the respective sub-domains for the individual serotypes and their variations are apparent from Table 1.

"Ganglioside Receptor"

The HCs of the Botulinus neurotoxins exhibit a high affinity to peripheral nerve cells which is mediated predominantly by the interaction with complex polysialogangliosides—these are glycolipids consisting of more than one sialic acid—(Halpern et al. (1995), Curr. Top. Microbiol. Immunol. 195, 221-41; WO 2006/02707). The LCs bound to them consequently only reach this cell type and become active in these cells only. BoNT/A and B merely bind one ganglioside GT1b molecule.

In the case of BoNT/B and BoNT/G the protein receptors are synaptotagmin I and synaptotagmin II. In the case of BoNT/A the protein receptors are the synaptic vesicles glycoproteins 2 (SV2), preferably SV2A, SV2B and SV2C.

At present 13 isoforms pertaining to the family of synaptotagmins are known. All are characterised by two carboxyl-terminal $Ca^{2+}$ binding C2-domains, a central transmembrane domain (TMD), which anchors the synaptotagmin in the synaptic vesicle membrane, and an amino terminus having different lengths. After the $Ca^{2+}$ inflow the fusion of the synaptic vesicle with the plasma membrane is initiated, whereupon the intraluminal amino terminus of the synaptotagmin is presented extracellularly and is available as receptor anchor for BoNT/B and G. Analogously thereto, the fourth luminal domain of the SV2 isoforms is available extracellularly, after exocytosis, for the interaction with BoNT/A.

The character of individual amino acids of the binding pocket was so modified by specific mutagenesis that binding to a protein receptor is rendered more difficult or is inhibited. For this purpose, the $H_C$-fragments of BoNT/B and BoNT/G were expressed in *E. coli* and isolated in the postulated binding pocket in recombinant form as wild type or with individual amino acid substitutions (mutations/substitutions). For a GST-pull-down-assay, in order to study the interaction in vitro between BoNT/B and BoNT/G as well as between synaptotagmin I and synaptotagmin II, the respective GST-synaptotagmin-fusion protein was incubated with different quantities of the respective $H_C$-fragment of BoNT/B or, respectively, BoNT/G and a phase separation was performed. Free $H_C$-fragment remained in the separated supernatant while bound BoNT $H_C$-fragment could be detected in the solid phase, together with GST-synaptotagmin-fusion protein. Substitution of the respective $H_C$-fragments by the full-length BoNT/B and G in the GST-pull-down assay showed the same results.

It was found in this context that the BoNT/B wild type only binds in the presence of complex gangliosides and synaptotagmin I with transmembrane domain, while synaptotagmin II binds both with or without transmembrane domain as well as in the presence or absence of complex gangliosides. By specifically substituting amino acids within the protein receptor binding site of BoNT/B it was possible to significantly increase or decrease the interaction between both synaptotagmin molecules (FIG. 1).

Figure 2:
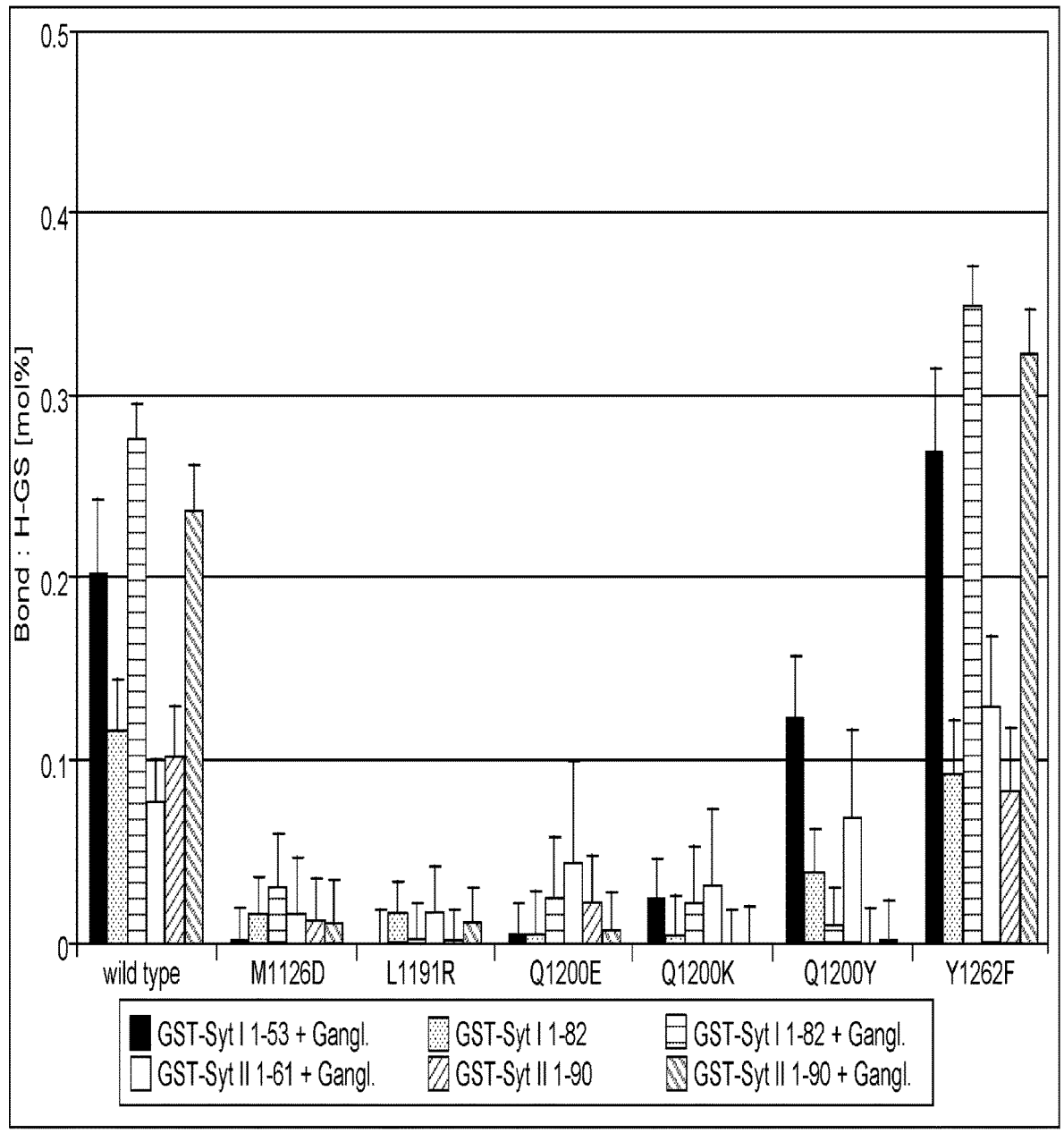

Furthermore, it was shown for the BoNT/G wild type that binding to synaptotagmin I and synaptotagmin II, in each case with or without transmembrane domain, is taking place both in the presence as well as in the absence of complex gangliosides. By specifically substituting amino acids homologous to BoNT/B, within the protein receptor binding site of BoNT/G, it was possible to significantly increase or decrease the interaction between both synaptotagmin molecules (FIG. 2).

Figure 3:
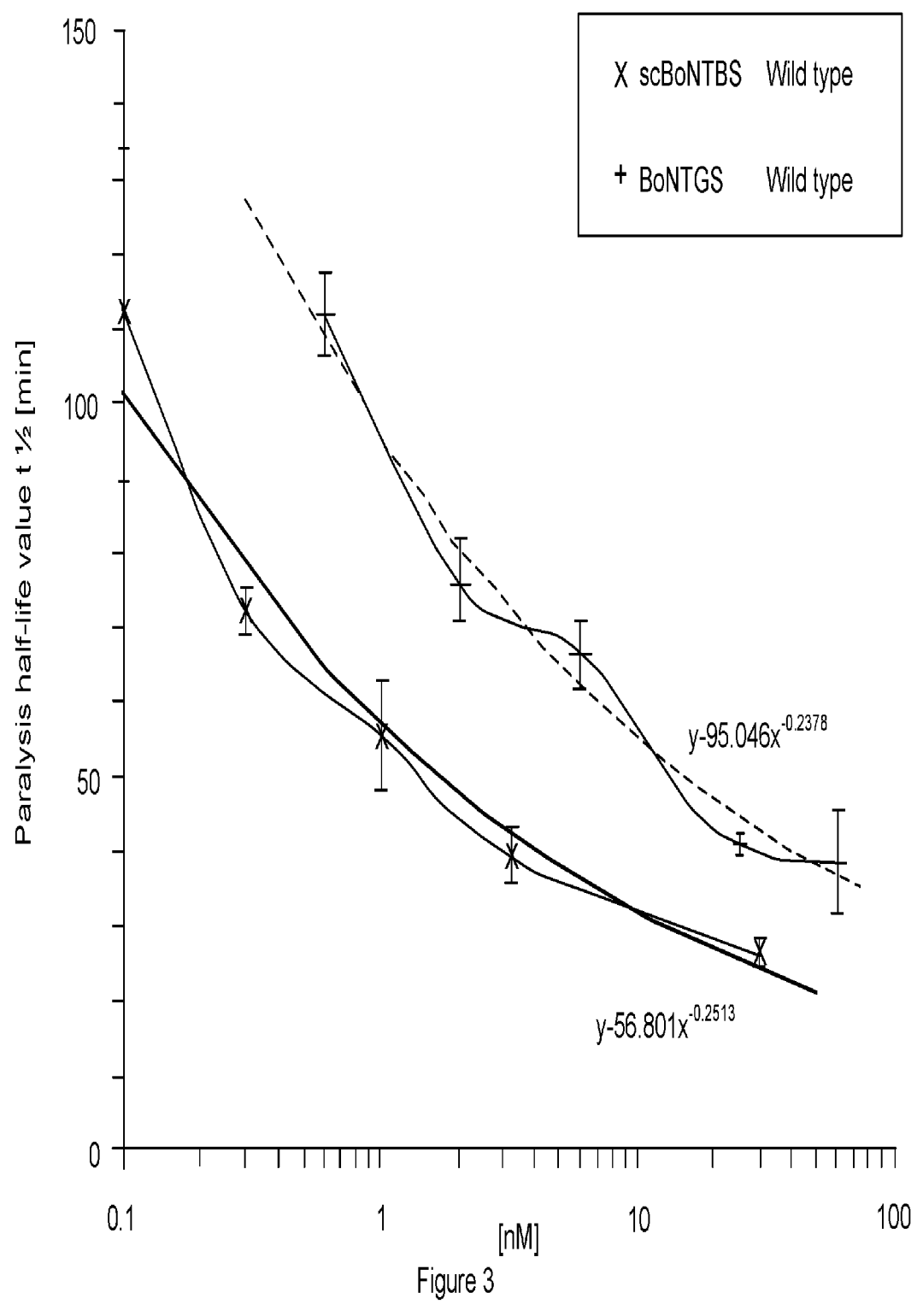
Figure 4:
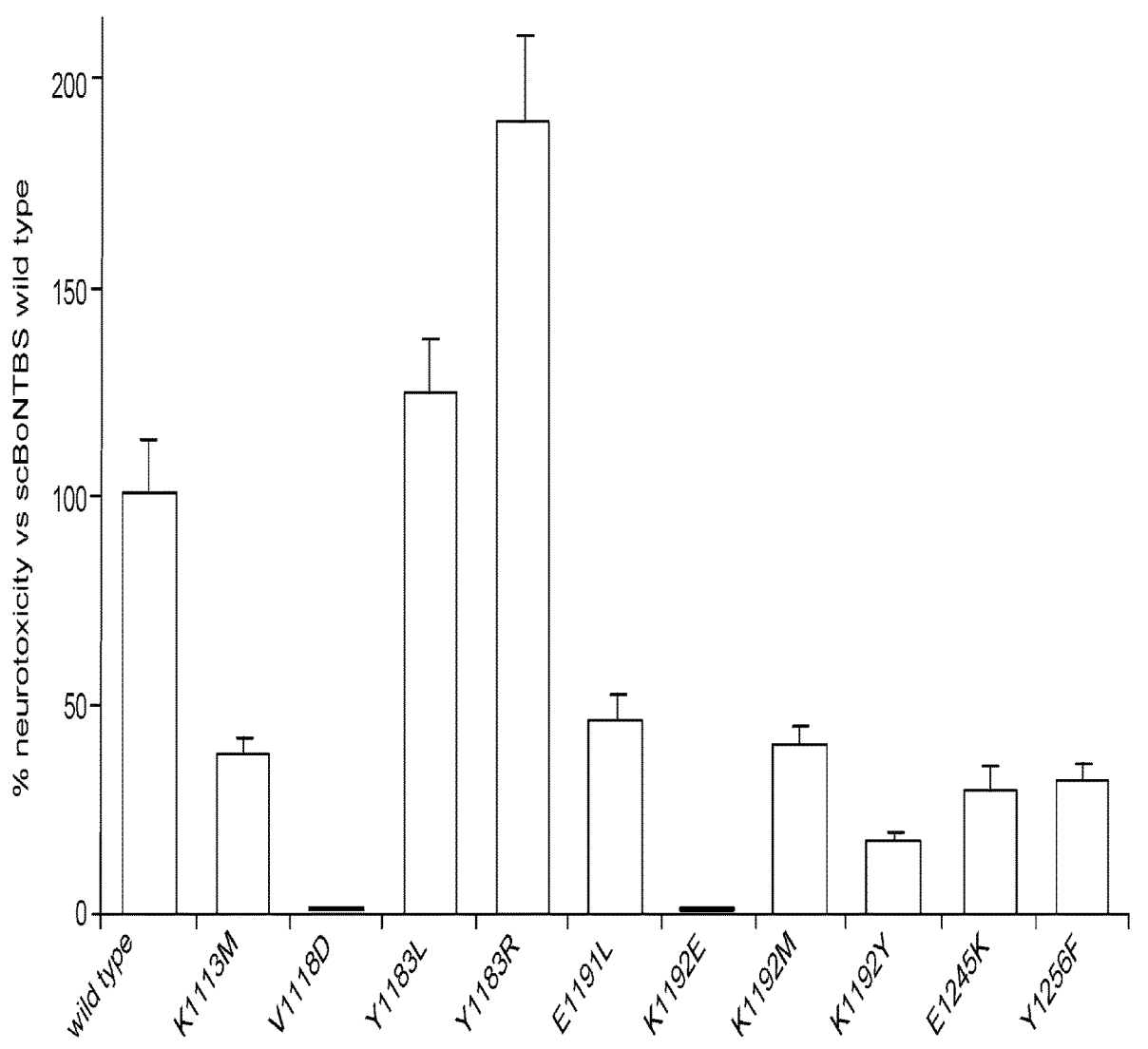
Figure 5:
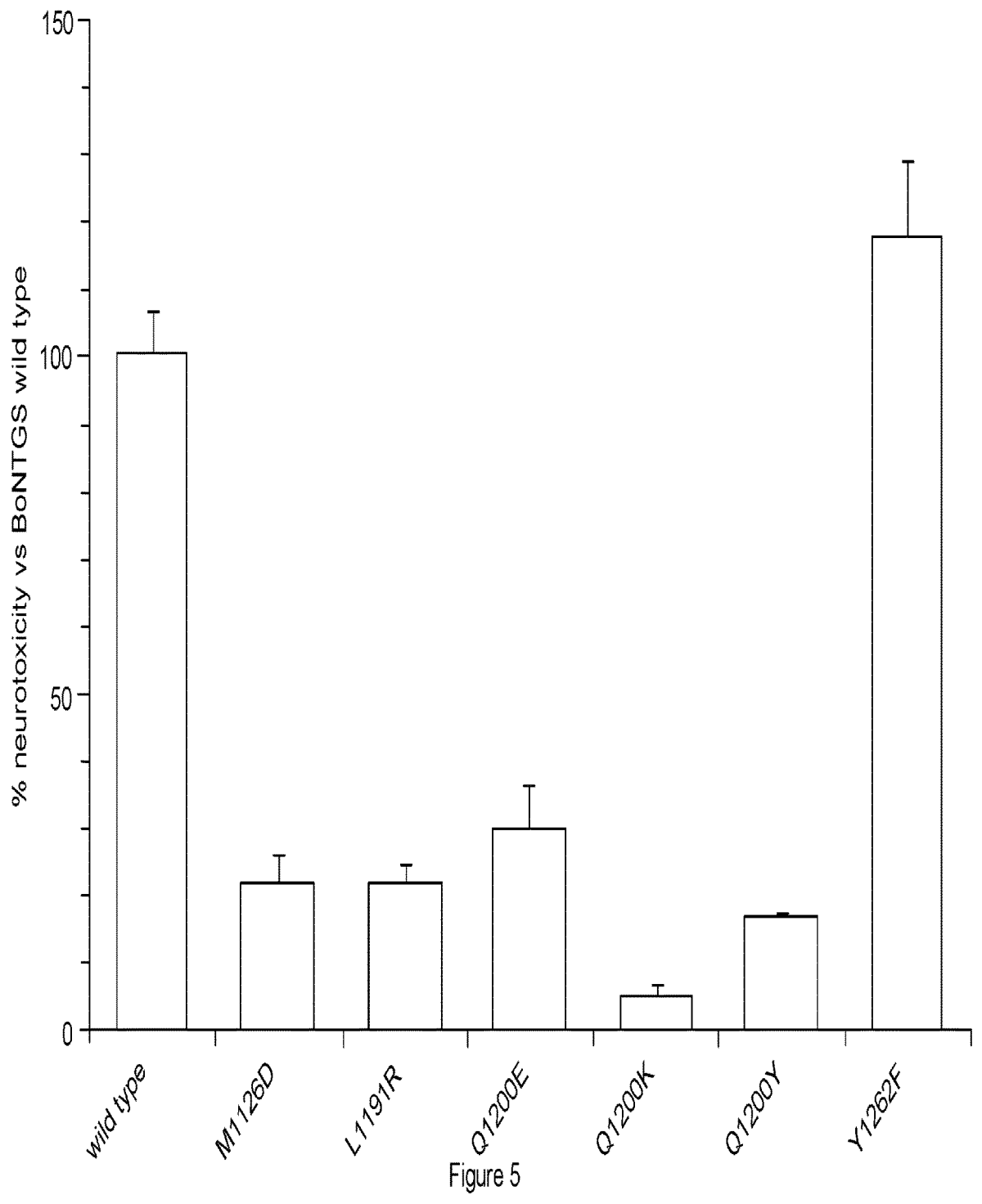
Figure 6:
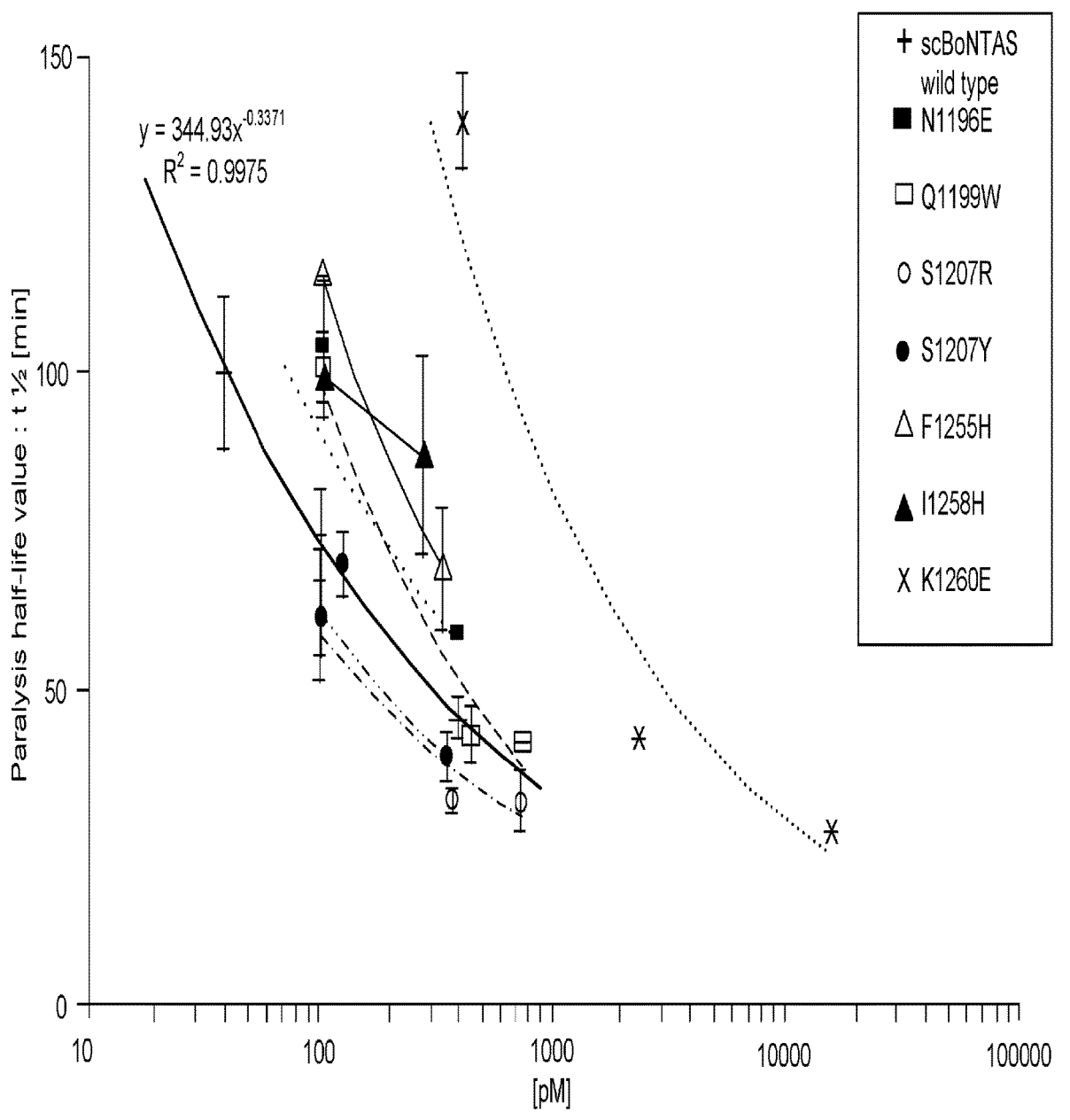

The potency of the full-length form of BoNT/A, B and G wild types was determined in the HDA by a dosage-effect-graph (FIGS. 3 and 6). The potency of the different full-length forms of BoNT/A, B and G single mutants was subsequently determined in the HDA (FIG. 6) and plotted against the potency of the BoNT/B and G wild types by means of an applied potency function (FIGS. 4 and 5). For example, the substitution of the amino acids valine 1118 by aspartate or lysine 1192 by glutamate in BoNT/B results in a drastic reduction of the potency to <2%. In contrast thereto, the mutation of the tyrosine 1183 in leucine or arginine, respectively, brings about a significant increase of the potency of BoNT/B (FIG. 4). Modifying tyrosine 1256 to phenylalanine in BoNT/G results likewise in an increase in potency while the mutation of glutamine 1200 in glutamate, lysine or tyrosine causes a considerable decrease of the potency of BoNT/G (FIG. 5). In the case of BoNT/A, modifying serine 1207 to arginine or tyrosine brings about an increase in potency while the mutation of lysine 1260 to glutamate causes a drastic potency reduction of the BoNT/A (FIG. 6).

According to a preferred embodiment the transport protein exhibits an affinity which is at least 15% higher or at least 15% lower than the native neurotoxin. Preferably, the transport protein exhibits an affinity which is at least 50% higher or lower, particularly preferred at least 80% higher or lower, and, in particular, at least 90% higher or lower than the native neurotoxin.

According to a preferred embodiment the modification of the HC takes place in the region of the $H_C$-fragment of the given neurotoxin. If the modification includes a substitution, deletion, insertion or addition, the latter may be performed, for example, by specific mutagenesis, methods in this context being known to the person skilled in the art. The amino acids present in the native neurotoxin are in this context modified either by naturally occurring or by not naturally occurring amino acids. Amino acids are, in principle, divided into different physicochemical groups. Aspartate and glutamate belong to the negatively-charged amino acids. Histidine, arginine and lysine belong to the positively-charged amino acids. Asparagine, glutamine, serine, threonine, cysteine and tyrosine belong to the polar amino acids. Glycine, alanine, valine, leucine, isoleucine, methionine, proline, phenylalanine and tryptophane belong to the non-polar amino acids. Aromatic side groups are to be found among the amino acids histidine, phenylalanine, tyrosine and tryptophane. In general, it is preferred to substitute an amino acid by a different amino acid pertaining to another physicochemical group.

According to a preferred embodiment of the invention, the transport protein is a Botulinus neurotoxin serotype A to G. The amino acid sequences of the native neurotoxins can in this context be obtained from publicly accessible databases as follows:

TABLE 1

Database numbers of the amino acid sequences and distribution of the sub-domains of the seven Botulinus neurotoxins.

| BoNT | Database no. of the protein sequence | SEQ ID NO.: | Number of the amino acids | $H_N$ | HC $H_{CN}$ | $H_{CC}$ |
|---|---|---|---|---|---|---|
| BoNT/A | AAA23262 AAM75961 AAQ06331 BTCLAB | 2 | 1296 | 449-866 | 867-1091 | 1092-1296 |
| | P10845 | 3 | 1296 | 449-866 | 867-1091 | 1092-1296 |
| | CAA36289 | 4 | 1296 | 449-866 | 867-1091 | 1092-1296 |
| | CAA51824 I40645 Q45894 | 5 | 1296 | 449-866 | 867-1091 | 1092-1296 |
| BoNT/B | AAL11499 AAL11498 | 6 | 1291 | 442-855 | 866-1078 | 1079-1291 |
| | CAA73968 | 7 | 1291 | 442-855 | 866-1078 | 1079-1291 |
| | AAK97132 | 8 | 1291 | 442-855 | 866-1078 | 1079-1291 |
| | A48940 AAA23211 P10844 | 9 | 1291 | 442-855 | 866-1078 | 1079-1291 |
| | BAC22064 | 10 | 1291 | 442-855 | 866-1078 | 1079-1291 |
| | CAA50482 I40631 | 11 | 1291 | 442-855 | 866-1078 | 1079-1291 |
| BoNT/C1 | A49777 BAA14235 CAA51313 S46431 | 12 | 1291 | 450-863 | 864-1092 | 1093-1291 |
| | BAB71749 | 13 | 1291 | 450-863 | 864-1092 | 1093-1291 |
| | P18640 | 14 | 1291 | 450-863 | 864-1092 | 1093-1291 |
| | BAA08418 | 15 | 1280 | 450-863 | 864-1083 | 1084-1280 |
| | BAA89713 | 16 | 1280 | 450-863 | 864-1083 | 1084-1280 |
| BoNT/D | CAA38175 P19321 S11455 | 17 | 1276 | 446-859 | 860-1079 | 1080-1276 |
| | AAB24244 | 18 | 1276 | 446-859 | 860-1079 | 1080-1276 |
| | BAA07477 S70582 | 19 | 1285 | 446-859 | 860-1088 | 1089-1285 |
| | BAA90661 | 20 | 1285 | 446-859 | 860-1088 | 1089-1285 |
| BoNT/E | BAB86845 CAA44558 S21178 | 21 | 1252 | 423-842 | 843-1066 | 1067-1252 |
| | CAA43999 Q00496 | 22 | 1251 | 423-842 | 843-1066 | 1067-1251 |
| | CAA43998 JH0256 P30995 | 23 | 1251 | 423-842 | 843-1066 | 1067-1251 |
| BoNT/F | 1904210A AAA23263 I40813 P30996 | 24 | 1274 | 440-860 | 861-1086 | 1087-1274 |
| | CAA73972 | 25 | 1280 | 440-861 | 862-1087 | 1088-1280 |
| | AAA23210 CAA57358 | 26 | 1278 | 440-861 | 862-1084 | 1085-1278 |
| | CAA48329 S33411 | 27 | 1268 | 432-853 | 854-1075 | 1076-1268 |
| BoNT/G | CAA52275 Q60393 | 28 | 1297 | 447-860 | 861-1086 | 1087-1297 |
| | S39791 | 29 | 1297 | 447-860 | 861-1086 | 1087-1297 |

With regard to the $H_C$-fragment of these Botulinus neurotoxins, the amino acids in the amino acid positions from
867 to 1296 of the C. botulinum neurotoxin serotype A,
866 to 1291 of the C. botulinum neurotoxin serotype B,
864 to 1291 or, respectively, 1280 of the C. botulinum neurotoxin serotype C1,
860 to 1276 or, respectively, 1285 of the C. botulinum neurotoxin serotype D,
843 to 1251 or, respectively, 1252 of the C. botulinum or C. butyricum neurotoxin serotype E,
861 to 1274, 862 to 1280 or, respectively, 1278 and 854 to 1268 of the C. botulinum or, respectively, C. baratii neurotoxin serotype F
861 to 1297 of the C. botulinum neurotoxin serotype G
are preferred for modification.

It is, therefore, preferred to modify post-translationally, and/or add, and/or delete, and/or insert, and/or substitute by an either naturally occurring or not naturally occurring amino acid at least one amino acid in the aforesaid positions.

According to a preferred embodiment, the neurotoxin is Botulinus neurotoxin serotype A. In this case, preferably at least one amino acid in the positions threonine 1195, asparagine 1196, glutamine 1199, lysine 1204, isoleucine 1205, leucine 1206, serine 1207, leucine 1209, aspartate 1213, leucine 1217, phenylalanine 1255, asparagine 1256, isoleucine 1258 and/or lysine 1260 of the Botulinus neurotoxin serotype A protein sequences is modified post-translationally, and/or added, and/or deleted, and/or inserted and/or substituted by an either naturally occurring or not naturally occurring amino acid. The positions asparagine 1196, glutamine 1199, serine 1207, phenylalanine 1255, isoleucine 1258 and/or lysine 1260 of the Botulinus neurotoxin serotype A protein sequences are particularly preferred. In particular, the positions serine 1207, substituted by arginine or tyrosine, and lysine 1260, substituted by glutamate, are preferred.

According to a preferred embodiment, the neurotoxin is Botulinus neurotoxin serotype B. In this case, preferably at least one amino acid in the positions lysine 1113, aspartate 1114, serine 1116, proline 1117, valine 1118, threonine 1182, tyrosine 1183, phenylalanine 1186, lysine 1188, glutamate 1191, lysine 1192, leucine 1193, phenylalanine 1194, phenylalanine 1204, phenylalanine 1243, glutamate 1245, lysine 1254, aspartate 1255 and tyrosine 1256 of the Botulinus neurotoxin serotype B protein sequences is modified post-translationally, and/or added, and/or deleted, and/or inserted and/or substituted by an either naturally occurring or not naturally occurring amino acid. The positions valine 1118, tyrosine 1183, glutamate 1191, lysine 1192, glutamate 1245 and tyrosine 1256 of the Botulinus neurotoxin serotype B protein sequences are particularly preferred. In particular, the positions of tyrosine 1183 and glutamate 1191, substituted by leucine, are preferred.

According to a further preferred embodiment, the neurotoxin is Botulinus neurotoxin serotype G. In this case, preferably at least one amino acid in the positions phenylalanine 1121, lysine 1123, alanine 1124, serine 1125, methionine 1126, valine 1190, leucine 1191, serine 1194, glutamate 1196, threonine 1199, glutamine 1200, leucine 1201, phenylalanine 1202, phenylalanine 1212, phenylalanine 1248, lysine 1250, aspartate 1251 and tyrosine 1262 of the Botulinus neurotoxin serotype G protein sequences is modified post-translationally, and/or added, and/or deleted, and/or inserted and/or substituted by an either naturally occurring or not naturally occurring amino acid. The positions methionine 1126, leucine 1191, threonine 1199, glutamine 1200, lysine 1250 and tyrosine 1262 of the Botulinus neurotoxin serotype G protein sequences are particularly preferred. In particular, the position tyrosine 1262, substituted by phenylalanine, is preferred.

The transport protein provided in the present invention exhibits an increased or reduced specific affinity of its protein-binding domain, in particular to molecules pertaining to the family of the synaptotagmins or the synaptic vesicle glycoproteins 2.

A further embodiment of the present invention relates to a composition containing a transport protein according to the invention and at least one intervening molecule (X). The intervening molecule may be a small organic molecule, a peptide or a protein; preferably covalently bonded to the transport protein by a peptide bond, an ester bond, an ether bond, a sulphide bond, a disulphide bond or a carbon-carbon-bond.

In addition, the intervening molecule includes all known therapeutically active substances. Cytostatics, antibiotics, virustatics, but also immunoglobulins are preferred in this context.

In a preferred embodiment, the protein is a protease, splitting one or a plurality of proteins of the release apparatus of neurotransmitters, the protease being selected from the group of neurotoxins consisting of the LCs of the C. botulinum neurotoxins, in particular of the serotype A, B, C1, D, E, F and G or a proteolytically active fragment of the LC of a C. botulinum neurotoxin, in particular a neurotoxin of the serotype A, B, C1, D, E, F and G, the fragment exhibiting at least 0.01%, preferably at least 5%, particularly preferably at least 50%, in particular at least 90% of the proteolytic activity of the native protease. Preferably, the transport protein and the protease are derived from the same C. botulinum neurotoxin serotype, in particular and preferably the $H_N$-domain of the transport protein and the protease are derived from the C. botulinum neurotoxin serotype A. The sequences of the proteases are generally accessible at databases and the database numbers are apparent from Table 1. The proteolytic activity of the proteases is determined by way of substrate separation kinetics (see Binz et al. (2002), Biochemistry 41(6), 1717-23).

According to a further embodiment of the present invention, a process for producing the transport protein is provided. In this case, in a first step a nucleic acid coding for the transport protein is provided. The coding nucleic acid may represent in this context RNA, DNA or mixtures thereof. The nucleic acid may furthermore be modified with regard to its nuclease resistance, such as e.g. by inserting phosphorthioate bonds. The nucleic acid may be produced from a starting nucleic acid, the latter being accessible e.g. by cloning from genomic or cDNA-databases. Moreover, the nucleic acid may be produced directly by solid phase synthesis. Suitable methods are known to the person skilled in the art. If one starts with a starting nucleic acid, a specific modification, e.g. by locality-specific mutagenesis, may be brought about, resulting in at least one addition, insertion, deletion and/or substitution on the amino acid level. The nucleic acid is then linked operatively to a suitable promoter. Suitable promoters for expression in known expression systems are known to the person skilled in the art. The choice of promoter depends in this case on the expression systems used for expression. In general, constitutive promoters are preferred, but inducible promoters may likewise be used. The construct produced in this manner includes at least one part of a vector, in particular regulatory elements, the vector being selected, for example, from X-derivates, adenoviruses, baculoviruses, vaccinia viruses, SV40-viruses and retroviruses. The vector is preferably capable of expressing the nucleic acid in a given host cell.

The invention further provides host cells, which contain the vector and are suitable for expressing the vector. Numerous prokaryotic and eukaryotic expression systems are known in the state of the art, the host cells being selected, for example, from prokaryotic cells such as E. coli or B. subtilis, from eukaryotic cells such as S. cerevisiae and P. pastoris. Although higher eukaryotic cells, such as insect cells or mammal cells, may be used as well, host cells are nevertheless preferred, which, like C. botulinum, do not possess a glycosylation apparatus.

According to a preferred embodiment the nucleic acid codes for the $H_C$-fragment of the C. botulinum neurotoxin. This nucleic acid contains endonuclease-interfaces, flanking the nucleic acid coding for the $H_C$-fragment, the endonuclease sites being compatible with those of other $H_C$-fragments of C. botulinum neurotoxins, in order to permit their easy modular substitution in the gene coding for the transport protein, while the similarity of the amino acid sequence is preserved.

If a composition according to the invention is provided, which, apart from the transport system, further contains at least one intervening molecule, and this intervening molecule is a peptide or protein, functionalised either with a carboxyl-terminal cysteine or a mercapto-group, then, in an analogous manner, as described before, the peptide and/or protein may be produced recombinantly, for example by using binary vectors or various host cells. If the same host cell is used for the expression both of the transport protein and the peptide or protein, an intermolecular disulphide bond is preferably formed in situ. For a more efficient production in the same host cell, the nucleic acid coding for the peptide or protein may also be translated with that of the transport protein in the same reading frame, so that a single-chain polypeptide is produced. In this case, preferably an intramolecular disulphide bond is formed in situ. For simple hydrolysis of the likewise present peptide cross-linking between the transport protein and the peptide and/or protein, an amino acid sequence is inserted at the amino-terminus of the transport protein, which is either specifically recognised and split by the protease thrombin or by a specific endoprotease of the host cell.

Surprisingly, it was found that the insert-sequence CXXXZKTKSLVPRGSKBXXC (SEQ ID NO:1), with X signifying any desired amino acid and Z and B being selected independently of each other from alanine, valine, serine, threonine and glycine, is split efficiently in vivo by an endogenous protease of a bacterial host, preferably *E. coli*. The insertion of the insert-sequence between the amino acid sequence of the transport protein and a further peptide or protein therefore offers the advantage that post-treatment at a later stage, e.g. by thrombin, is not necessary. The *E. coli*-strain *E. coli* K12 is particularly preferred.

Preferably, the insert-sequence forms part of a loop with 18 20, preferably amino acids.

If this is not possible, an appropriate intermolecular disulphide-bond, after separate purification of the transport protein and the protein, may subsequently be brought about by oxidation processes known to the person skilled in the art. The peptide or protein may also be obtained directly by synthesis or fragment condensation. Appropriate methods are known to the person skilled in the art.

The transport protein and the peptide, or protein, respectively, are subsequently purified. For this purpose methods are used, known to the person skilled in the art, such as e.g. chromatography-methods or electrophoresis.

A further embodiment of the present invention relates to the pharmaceutical composition, which includes the transport protein or a composition and optionally a pharmaceutically acceptable excipient, a diluent and/or an additive.

The pharmaceutical composition is suitable for oral, intravenous, subcutaneous, intramuscular and topical administration. Intramuscular administration is preferred in this context. A dosing unit of the pharmaceutical composition contains approximately 0.1 pg to 1 mg of transport protein and/or the composition according to the invention.

The pharmaceutical composition is suitable to treat disorders of neurotransmitter release and disorders such as hemi-facial spasms, spasmodic torticollis, blepharospasm, spasticities, dystonias, migraine, pain, disorders of the neck and lumbar vertebral column, strabism, hypersalivation, wound healing, snoring and depression.

A further embodiment of the present invention includes a cosmetic composition, containing a transport protein and a cosmetically acceptable excipient, diluent and/or additive. The cosmetic composition is suitable for treating hyperhidrosis and facial wrinkles.

FIG. 1: Study of the in vitro bond of the wild type and mutated BoNT/B $H_C$-fragments to shortened GST-syt I and GST-syt II fusion proteins in the presence or absence of complex gangliosides by means of GST-pull-down assay.

FIG. 2: Study of the in vitro bond of the wild type and mutated BoNT/G $H_C$-fragments to shortened GST-syt I and GST-syt II fusion proteins in the presence or absence of complex gangliosides by means of GST-pull-down assay.

FIG. 3: Dosage-effect-graph of the BoNT/B and G wild types in the HDA. The applied potency functions permit a relative comparison of the paralysis times of single mutants with those of the associated wild types.

FIG. 4: Increase and decrease of the neurotoxicity of the BoNT/B single mutants compared to the wild type in the HDA.

FIG. 5: Increase and decrease of the neurotoxicity of the BoNT/G single mutants compared to the wild type in the HDA.

FIG. 6: Dosage-effect-graphs of the BoNT/A wild type and the BoNT/A single mutants in the HDA.

In detail, the present invention relates to a transport protein (Trapo), formed by modifying the HC of the neurotoxin produced by *C. botulinum*, preferably specifically binding to neurons, and preferably absorbed intracellularly by receptor-mediated endocytosis and translocated from the acid endosomal compartment into the cytosol of neurons. This protein is used as a transporting means in order to introduce into the cells proteases and other substances bound to the said transporting means, unable to penetrate physiologically into the plasma membrane and to reach the cytosol of nerve cells. The substrates of the proteases are intracellularly localised proteins and peptides participating in the transmitter release. After separation of the substrates, the specific functions of the neurons are blocked; the cells themselves are not damaged. One of these functions is exocytosis, bringing about the neurotransmitter release. If the release of transmitters is inhibited, the transmission of signals from cell to cell is blocked. For example, striated muscles are paralysed if the release of acetyl choline is inhibited at the neuromuscular contact point. This effect may be used therapeutically, if the transport protein is applied to nerve ends of spastic or dystonic muscles. Other active substances are, for example, substances exhibiting anti-viral action. Conjugated with the transport protein, they are of use for treating viral infections of the nervous system. The present invention also relates to the use of a transport protein for inhibiting the release of neurotransmitters.

Transport proteins with a relatively low affinity bind to the nerve cells, but are not absorbed by them. These transport proteins are therefore suitable to serve as specific transporting means towards the surface of the nerve cells.

If patients are treated with the progenitor toxins A and B from *C. botulinum*, the injection of these non-human proteins, despite the low dosage, causes the formation of antibodies, so that the therapy shows no effect and must therefore be stopped in order to prevent anaphylactic shock. By applying a substance with the same active mechanism having a higher transport efficiency of the enzymatic activity, the dosage may be lowered drastically and the formation of antibodies will not occur. These properties are attributed to the transport protein described herein.

Although examples for application are given, the suitable mode of application and the dosage is, in general, individually determined by the treating physician. Such decisions are routinely made by each physician well versed in the relevant special field. Thus, the mode of application and the dosage of the neurotoxin may e.g. be selected in accordance with the invention described herein, based on criteria such as the solubility of the selected neurotoxin or the intensity of the pain to be treated.

The treatment interval for the native progenitor toxins A and B from *C. botulinum* is currently three to four months on average. Prolonging this interval would reduce the risk of the formation of antibodies and allow a longer treatment period with BoNT. The increase of LC in the cytosol would retard its decomposition and would thus also prolong the duration of efficacy. The transport protein described here exhibits a higher affinity and absorption rate than the native HC.

The following example merely serves for elucidation and should not be understood in a limiting manner.

Material and Methods

Plasmid Construction and Preparation of Recombinant Proteins

Plasmids for *E. coli* expression of recombinant $H_C$-fragments of BoNT/B and BoNT/G as well as of the full-length form of BoNT/A, B and G with carboxyl-terminal StrepTag for affinity purification were brought about by PCR-methods with suitable primers, chromosomal DNA coding for BoNT/A (AAA23262) BoNT/B (AAA23211) and BoNT/G (CAA52275) and the expression vector pQe3 (Quiagen AG) serving as the starting vector. Shortened variations of rat-synaptotagmin I (syt I) (amino acids 1-53; amino acids 1-82) and rat-synaptotagmin II (syt II) (amino acids 1-61; amino acids 1-90) were cloned into the GST-coding vector pGEX-2T (Amersham Biosciences AB). The nucleic acid sequences of all plasmids were confirmed by DNA-sequencing. The recombinant $H_C$-fragments and those of the full-length form of BoNT were prepared at room temperature in the *E. coli*-strain M15 [pRep4] (Qiagen) during induction for ten hours and purified on a StrepTactin-matrix (IBA GmbH) in accordance with the manufacturer's instructions. The GST-fusion proteins obtained from *E. coli* BL21 were isolated with the aid of glutathione immobilised on sepharose micro-beads. Fractions containing the desired proteins were combined and dialysed against Tris-NaCl-triton-buffer (20 mM Tris-HCl, 150 mM NaCl, 0.5% Triton X-100, pH 7.2).

GST-Pull-Down Assay

GST-fusion proteins (0.12 nmol each), which had been immobilised on 10 µl GT-sepharose micro-beads, were incubated at 4° C. for 2 h with $H_C$-fragments (0.1 nmol) in the absence or in the presence of a bovine brain-ganglioside-mixture (18% GM1, 55% GD1a, 10% GT1b, 2% other gangliosides; Calbiochem; 20 µg each) in a total volume of 180 µl Tris-NaCl-triton-buffer. The micro-beads were collected by centrifuging, the supernatant was removed and the separated micro-beads were in each case rinsed three times with 400 µl of the same buffer. The rinsed pellet fractions were boiled in SDS-sample buffer and studied, together with the supernatant fractions, by SDS-PAGE and Coomassie blue staining.

The BoNT/B wild type binds only in the presence of complex gangliosides and synaptotagmin I with transmembrane domain, while synaptotagmin II binds with or without transmembrane domain as well as in the presence or in the absence of complex gangliosides. By specifically substituting amino acids within the protein receptor binding site of BoNT/B it was possible to significantly increase (E1191L; Y1183L) or decrease (V1118D; K1192E) the interaction between both synaptotagmin molecules (FIG. 1).

For the BoNT/G wild type it was shown that binding to synaptotagmin I and synaptotagmin II, in each case with or without transmembrane domain, is taking place both in the presence as well as in the absence of complex gangliosides. By specifically substituting amino acids homologous to BoNT/B, within the protein receptor binding site of BoNT/G, it was possible to significantly increase (Y1262F) or decrease (Q1200E) the interaction between both synaptotagmin molecules (FIG. 2).

By detecting the bond of the recombinant $H_C$-fragments of BoNT/B and G to isolated, immobilised gangliosides, it was possible to exclude damage to the function of the neighbouring ganglioside-binding pocket by the mutations introduced into the syt-binding pocket and to draw adequate conclusions to an intact tertiary structure of the $H_C$-fragment. These results were supported by CD-spectroscopic studies as well as by thermal denaturation experiments, likewise displaying intact tertiary structures of the mutated $H_C$-fragments of BoNT/B and G.

Mouse Hemidiaphragm Assay (HDA)

The neurotoxicity of the BoNT/A, B and G-mutants was determined as described by Habermann et al., Naunyn Schmiedeberg's Arch. Pharmacol. 311 (1980), 33-40.

The potency of the full-length form of BoNT/A, B and G wild types was determined in the HDA by a dosage-effect-graph (FIGS. 3 and 6). The potency of the different full-length forms of BoNT/A, B and G single mutants was subsequently determined in the HDA (FIG. 6) and plotted against the potency of the BoNT/B and G wild types by means of an applied potency function (FIGS. 4 and 5). Thus, the substitution of the amino acids valine 1118 by aspartate or lysine 1192 by glutamate in BoNT/B results in a drastic reduction of the potency to <2%. In contrast thereto, the mutation of the tyrosine 1183 in leucine or arginine, respectively, brings about a significant increase of the potency of BoNT/B (FIG. 4). Modifying tyrosine 1256 to phenylalanine in BoNT/G results likewise in an increase in potency while the mutation of glutamine 1200 in glutamate, lysine or tyrosine causes a considerable decrease of the potency of BoNT/G (FIG. 5). In the case of BoNT/A, modifying serine 1207 to arginine or tyrosine brings about an increase in potency while the mutation of lysine 1260 to glutamate causes a drastic potency reduction of the BoNT/A (FIG. 6).

The invention claimed is:

1. An expression vector comprising a nucleic acid sequence that encodes a transport protein comprising a modified clostridial neurotoxin, wherein:
   (a) the modified clostridial neurotoxin comprises a heavy chain comprising: (i) an $H_N$-fragment; and (ii) an $H_C$-fragment comprising a $H_{CC}$-fragment and a $H_{CN}$-fragment, wherein the $H_{CC}$-fragment binds to a nerve cell with a higher or lower affinity than the corresponding native neurotoxin; and
   (b) the modified clostridial neurotoxin is a *Clostridium botulinum* neurotoxin serotype A selected from SEQ ID NO: 2, 3, 4, and 5, modified by the substitution of at least one amino acid at any one of positions 1195, 1196, 1199, 1204, 1205, 1206, 1207, 1209, 1213, 1217, 1255, 1256, 1258, and/or 1260 with either a naturally occurring or a non-naturally occurring amino acid.

2. A host cell comprising the vector of claim 1.

3. The host cell of claim 2, wherein the cell is *Escherichia coli, Saccharomyces cerevisiae, Pichia pastoris* or *Bacillus megaterium*.

4. The vector of claim 1, wherein the modified clostridial neurotoxin is a *Clostridium botulinum* neurotoxin serotype A selected from SEQ ID NO: 2, 3, and 4, modified by the substitution of at least one amino acid at any one of positions 1195, 1196, 1199, 1204, 1205, 1206, 1207, 1209, 1213, 1217, 1255, 1256, 1258, and/or 1260 with either a naturally occurring or a non-naturally occurring amino acid.

5. The vector of claim 1, wherein the modified clostridial neurotoxin is a *Clostridium botulinum* neurotoxin serotype A of SEQ ID NO: 2, modified by the substitution of at least one amino acid at any one of positions 1195, 1196, 1199, 1204, 1205, 1206, 1207, 1209, 1213, 1217, 1255, 1256, 1258, and/or 1260 with either a naturally occurring or a non-naturally occurring amino acid.

6. The vector of claim 1, wherein the modified clostridial neurotoxin is a *Clostridium botulinum* neurotoxin serotype A of SEQ ID NO: 3, modified by the substitution of at least one amino acid at any one of positions 1195, 1196, 1199, 1204, 1205, 1206, 1207, 1209, 1213, 1217, 1255, 1256, 1258, and/or 1260 with either a naturally occurring or a non-naturally occurring amino acid.

7. The vector of claim 1, wherein the modified clostridial neurotoxin is a *Clostridium botulinum* neurotoxin serotype A of SEQ ID NO: 4, modified by the substitution of at least one amino acid at any one of positions 1195, 1196, 1199, 1204, 1205, 1206, 1207, 1209, 1213, 1217, 1255, 1256, 1258, and/or 1260 with either a naturally occurring or a non-naturally occurring amino acid.

8. The vector of claim 1, wherein the modified clostridial neurotoxin is a *Clostridium botulinum* neurotoxin serotype A of SEQ ID NO: 5, modified by the substitution of at least one amino acid at any one of positions 1195, 1196, 1199, 1204, 1205, 1206, 1207, 1209, 1213, 1217, 1255, 1256, 1258, and/or 1260 with either a naturally occurring or a non-naturally occurring amino acid.

* * * * *

SEQUENCE LISTING

<160> NUMBER OF SEQ ID NOS: 29

<210> SEQ ID NO 1
<211> LENGTH: 20
<212> TYPE: PRT
<213> ORGANISM: Artificial Sequence
<220> FEATURE:
<223> OTHER INFORMATION: Cleavage site
<220> FEATURE:
<221> NAME/KEY: VARIANT

```
<222> LOCATION: (2)..(4)
<223> OTHER INFORMATION: Xaa = any naturally occurring amino acid
<220> FEATURE:
<221> NAME/KEY: VARIANT
<222> LOCATION: (5)..(5)
<223> OTHER INFORMATION: Xaa = a selection from Alanine, Valine, Serine,
      Threonine, and Glycine
<220> FEATURE:
<221> NAME/KEY: VARIANT
<222> LOCATION: (17)..(17)
<223> OTHER INFORMATION: Xaa = a selection from Alanine, Valine, Serine,
      Threonine, and Glycine
<220> FEATURE:
<221> NAME/KEY: VARIANT
<222> LOCATION: (18)..(19)
<223> OTHER INFORMATION: Xaa = any naturally occurring amino acid

<400> SEQUENCE: 1

Cys Xaa Xaa Xaa Lys Thr Lys Ser Leu Val Pro Arg Gly Ser Lys
1               5                   10                  15

Xaa Xaa Xaa Cys
            20

<210> SEQ ID NO 2
<211> LENGTH: 1296
<212> TYPE: PRT
<213> ORGANISM: Clostridium botulinum
<300> PUBLICATION INFORMATION:
<308> DATABASE ACCESSION NUMBER: VERSION AAA23262.1  GI:144865
<300> PUBLICATION INFORMATION:
<308> DATABASE ACCESSION NUMBER: AAM75961
<300> PUBLICATION INFORMATION:
<308> DATABASE ACCESSION NUMBER: AAQ06331

<400> SEQUENCE: 2

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
```

-continued

```
              210                 215                 220
Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                    245                 250                 255

Glu Val Ser Phe Glu Glu Leu Arg Thr Phe Gly Gly His Asp Ala Lys
                260                 265                 270

Phe Ile Asp Ser Leu Gln Glu Asn Glu Phe Arg Leu Tyr Tyr Tyr Asn
                275                 280                 285

Lys Phe Lys Asp Ile Ala Ser Thr Leu Asn Lys Ala Lys Ser Ile Val
            290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                    325                 330                 335

Lys Phe Asp Lys Leu Tyr Lys Met Leu Thr Glu Ile Tyr Thr Glu Asp
                340                 345                 350

Asn Phe Val Lys Phe Phe Lys Val Leu Asn Arg Lys Thr Tyr Leu Asn
                355                 360                 365

Phe Asp Lys Ala Val Phe Lys Ile Asn Ile Val Pro Lys Val Asn Tyr
            370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                    405                 410                 415

Lys Asn Phe Thr Gly Leu Phe Glu Phe Tyr Lys Leu Leu Cys Val Arg
                420                 425                 430

Gly Ile Ile Thr Ser Lys Thr Lys Ser Leu Asp Lys Gly Tyr Asn Lys
                435                 440                 445

Ala Leu Asn Asp Leu Cys Ile Lys Val Asn Asn Trp Asp Leu Phe Phe
            450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                    485                 490                 495

Asp Leu Ile Gln Gln Tyr Tyr Leu Thr Phe Asn Phe Asn Glu Pro
                500                 505                 510

Glu Asn Ile Ser Ile Glu Asn Leu Ser Ser Asp Ile Ile Gly Gln Leu
                515                 520                 525

Glu Leu Met Pro Asn Ile Glu Arg Phe Pro Asn Gly Lys Lys Tyr Glu
530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                    565                 570                 575

Leu Asn Pro Ser Arg Val Tyr Thr Phe Phe Ser Ser Asp Tyr Val Lys
                580                 585                 590

Lys Val Asn Lys Ala Thr Glu Ala Ala Met Phe Leu Gly Trp Val Glu
                595                 600                 605

Gln Leu Val Tyr Asp Phe Thr Asp Glu Thr Ser Glu Val Ser Thr Thr
            610                 615                 620

Asp Lys Ile Ala Asp Ile Thr Ile Ile Ile Pro Tyr Ile Gly Pro Ala
625                 630                 635                 640
```

-continued

```
Leu Asn Ile Gly Asn Met Leu Tyr Lys Asp Asp Phe Val Gly Ala Leu
                645                 650                 655
Ile Phe Ser Gly Ala Val Ile Leu Leu Glu Phe Ile Pro Glu Ile Ala
            660                 665                 670
Ile Pro Val Leu Gly Thr Phe Ala Leu Val Ser Tyr Ile Ala Asn Lys
        675                 680                 685
Val Leu Thr Val Gln Thr Ile Asp Asn Ala Leu Ser Lys Arg Asn Glu
    690                 695                 700
Lys Trp Asp Glu Val Tyr Lys Tyr Ile Val Thr Asn Trp Leu Ala Lys
705                 710                 715                 720
Val Asn Thr Gln Ile Asp Leu Ile Arg Lys Met Lys Glu Ala Leu
                725                 730                 735
Glu Asn Gln Ala Glu Ala Thr Lys Ala Ile Ile Asn Tyr Gln Tyr Asn
                740                 745                 750
Gln Tyr Thr Glu Glu Lys Asn Asn Ile Asn Phe Asn Ile Asp Asp
        755                 760                 765
Leu Ser Ser Lys Leu Asn Glu Ser Ile Asn Lys Ala Met Ile Asn Ile
    770                 775                 780
Asn Lys Phe Leu Asn Gln Cys Ser Val Ser Tyr Leu Met Asn Ser Met
785                 790                 795                 800
Ile Pro Tyr Gly Val Lys Arg Leu Glu Asp Phe Asp Ala Ser Leu Lys
                805                 810                 815
Asp Ala Leu Leu Lys Tyr Ile Tyr Asp Asn Arg Gly Thr Leu Ile Gly
                820                 825                 830
Gln Val Asp Arg Leu Lys Asp Lys Val Asn Asn Thr Leu Ser Thr Asp
        835                 840                 845
Ile Pro Phe Gln Leu Ser Lys Tyr Val Asp Asn Gln Arg Leu Leu Ser
    850                 855                 860
Thr Phe Thr Glu Tyr Ile Lys Asn Ile Ile Asn Thr Ser Ile Leu Asn
865                 870                 875                 880
Leu Arg Tyr Glu Ser Asn His Leu Ile Asp Leu Ser Arg Tyr Ala Ser
                885                 890                 895
Lys Ile Asn Ile Gly Ser Lys Val Asn Phe Asp Pro Ile Asp Lys Asn
                900                 905                 910
Gln Ile Gln Leu Phe Asn Leu Glu Ser Ser Lys Ile Glu Val Ile Leu
        915                 920                 925
Lys Asn Ala Ile Val Tyr Asn Ser Met Tyr Glu Asn Phe Ser Thr Ser
    930                 935                 940
Phe Trp Ile Arg Ile Pro Lys Tyr Phe Asn Ser Ile Ser Leu Asn Asn
945                 950                 955                 960
Glu Tyr Thr Ile Ile Asn Cys Met Glu Asn Asn Ser Gly Trp Lys Val
                965                 970                 975
Ser Leu Asn Tyr Gly Glu Ile Ile Trp Thr Leu Gln Asp Thr Gln Glu
                980                 985                 990
Ile Lys Gln Arg Val Val Phe Lys Tyr Ser Gln Met Ile Asn Ile Ser
        995                 1000                1005
Asp Tyr Ile Asn Arg Trp Ile Phe Val Thr Ile Thr Asn Asn Arg
    1010                1015                1020
Leu Asn Asn Ser Lys Ile Tyr Ile Asn Gly Arg Leu Ile Asp Gln
    1025                1030                1035
Lys Pro Ile Ser Asn Leu Gly Asn Ile His Ala Ser Asn Asn Ile
    1040                1045                1050
```

Met Phe Lys Leu Asp Gly Cys Arg Asp Thr His Arg Tyr Ile Trp
1055                1060                1065

Ile Lys Tyr Phe Asn Leu Phe Asp Lys Glu Leu Asn Glu Lys Glu
1070                1075                1080

Ile Lys Asp Leu Tyr Asp Asn Gln Ser Asn Ser Gly Ile Leu Lys
1085                1090                1095

Asp Phe Trp Gly Asp Tyr Leu Gln Tyr Asp Lys Pro Tyr Tyr Met
1100                1105                1110

Leu Asn Leu Tyr Asp Pro Asn Lys Tyr Val Asp Val Asn Asn Val
1115                1120                1125

Gly Ile Arg Gly Tyr Met Tyr Leu Lys Gly Pro Arg Gly Ser Val
1130                1135                1140

Met Thr Thr Asn Ile Tyr Leu Asn Ser Ser Leu Tyr Arg Gly Thr
1145                1150                1155

Lys Phe Ile Ile Lys Lys Tyr Ala Ser Gly Asn Lys Asp Asn Ile
1160                1165                1170

Val Arg Asn Asn Asp Arg Val Tyr Ile Asn Val Val Val Lys Asn
1175                1180                1185

Lys Glu Tyr Arg Leu Ala Thr Asn Ala Ser Gln Ala Gly Val Glu
1190                1195                1200

Lys Ile Leu Ser Ala Leu Glu Ile Pro Asp Val Gly Asn Leu Ser
1205                1210                1215

Gln Val Val Val Met Lys Ser Lys Asn Asp Gln Gly Ile Thr Asn
1220                1225                1230

Lys Cys Lys Met Asn Leu Gln Asp Asn Asn Gly Asn Asp Ile Gly
1235                1240                1245

Phe Ile Gly Phe His Gln Phe Asn Asn Ile Ala Lys Leu Val Ala
1250                1255                1260

Ser Asn Trp Tyr Asn Arg Gln Ile Glu Arg Ser Ser Arg Thr Leu
1265                1270                1275

Gly Cys Ser Trp Glu Phe Ile Pro Val Asp Asp Gly Trp Gly Glu
1280                1285                1290

Arg Pro Leu
1295

<210> SEQ ID NO 3
<211> LENGTH: 1296
<212> TYPE: PRT
<213> ORGANISM: Clostridium botulinum

<400> SEQUENCE: 3

Met Pro Phe Val Asn Lys Gln Phe Asn Tyr Lys Asp Pro Val Asn Gly
1               5                   10                  15

Val Asp Ile Ala Tyr Ile Lys Ile Pro Asn Val Gly Gln Met Gln Pro
                20                  25                  30

Val Lys Ala Phe Lys Ile His Asn Lys Ile Trp Val Ile Pro Glu Arg
            35                  40                  45

Asp Thr Phe Thr Asn Pro Glu Glu Gly Asp Leu Asn Pro Pro Pro Glu
        50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
                100                 105                 110

```
Arg Gly Ile Pro Phe Trp Gly Gly Ser Thr Ile Asp Thr Glu Leu Lys
            115                 120                 125

Val Ile Asp Thr Asn Cys Ile Asn Val Ile Gln Pro Asp Gly Ser Tyr
130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Ser Leu Glu Val Asp Thr Asn Pro Leu Leu
            195                 200                 205

Gly Ala Gly Lys Phe Ala Thr Asp Pro Ala Val Thr Leu Ala His Glu
            210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
            275                 280                 285

Lys Phe Lys Asp Ile Ala Ser Thr Leu Asn Lys Ala Lys Ser Ile Val
            290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
            370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
            435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
            515                 520                 525
```

-continued

```
Glu Leu Met Pro Asn Ile Glu Arg Phe Pro Asn Gly Lys Lys Tyr Glu
        530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
    930                 935                 940

Phe Trp Ile Arg Ile Pro Lys Tyr Phe Asn Ser Ile Ser Leu Asn Asn
```

```
                945                 950                 955                 960
            Glu Tyr Thr Ile Ile Asn Cys Met Glu Asn Asn Ser Gly Trp Lys Val
                            965                 970                 975
            Ser Leu Asn Tyr Gly Glu Ile Ile Trp Thr Leu Gln Asp Thr Gln Glu
                        980                 985                 990
            Ile Lys Gln Arg Val Val Phe Lys Tyr Ser Gln Met Ile Asn Ile Ser
                    995                 1000                1005
            Asp Tyr Ile Asn Arg Trp Ile Phe Val Thr Ile Thr Asn Asn Arg
                1010                1015                1020
            Leu Asn Asn Ser Lys Ile Tyr Ile Asn Gly Arg Leu Ile Asp Gln
                1025                1030                1035
            Lys Pro Ile Ser Asn Leu Gly Asn Ile His Ala Ser Asn Asn Ile
                1040                1045                1050
            Met Phe Lys Leu Asp Gly Cys Arg Asp Thr His Arg Tyr Ile Trp
                1055                1060                1065
            Ile Lys Tyr Phe Asn Leu Phe Asp Lys Glu Leu Asn Glu Lys Glu
                1070                1075                1080
            Ile Lys Asp Leu Tyr Asp Asn Gln Ser Asn Ser Gly Ile Leu Lys
                1085                1090                1095
            Asp Phe Trp Gly Asp Tyr Leu Gln Tyr Asp Lys Pro Tyr Tyr Met
                1100                1105                1110
            Leu Asn Leu Tyr Asp Pro Asn Lys Tyr Val Asp Val Asn Asn Val
                1115                1120                1125
            Gly Ile Arg Gly Tyr Met Tyr Leu Lys Gly Pro Arg Gly Ser Val
                1130                1135                1140
            Met Thr Thr Asn Ile Tyr Leu Asn Ser Ser Leu Tyr Arg Gly Thr
                1145                1150                1155
            Lys Phe Ile Ile Lys Lys Tyr Ala Ser Gly Asn Lys Asp Asn Ile
                1160                1165                1170
            Val Arg Asn Asn Asp Arg Val Tyr Ile Asn Val Val Val Lys Asn
                1175                1180                1185
            Lys Glu Tyr Arg Leu Ala Thr Asn Ala Ser Gln Ala Gly Val Glu
                1190                1195                1200
            Lys Ile Leu Ser Ala Leu Glu Ile Pro Asp Val Gly Asn Leu Ser
                1205                1210                1215
            Gln Val Val Val Met Lys Ser Lys Asn Asp Gln Gly Ile Thr Asn
                1220                1225                1230
            Lys Cys Lys Met Asn Leu Gln Asp Asn Asn Gly Asn Asp Ile Gly
                1235                1240                1245
            Phe Ile Gly Phe His Gln Phe Asn Asn Ile Ala Lys Leu Val Ala
                1250                1255                1260
            Ser Asn Trp Tyr Asn Arg Gln Ile Glu Arg Ser Ser Arg Thr Leu
                1265                1270                1275
            Gly Cys Ser Trp Glu Phe Ile Pro Val Asp Asp Gly Trp Gly Glu
                1280                1285                1290
            Arg Pro Leu
                1295

<210> SEQ ID NO 4
<211> LENGTH: 1296
<212> TYPE: PRT
<213> ORGANISM: Clostridium botulinum
<300> PUBLICATION INFORMATION:
<308> DATABASE ACCESSION NUMBER: CAA36289
```

<400> SEQUENCE: 4

```
Met Gln Phe Val Asn Lys Gln Phe Asn Tyr Lys Asp Pro Val Asn Gly
1               5                   10                  15

Val Asp Ile Ala Tyr Ile Lys Ile Pro Asn Val Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
            115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415
```

-continued

```
Lys Asn Phe Thr Gly Leu Phe Glu Phe Tyr Lys Leu Leu Cys Val Arg
            420                 425                 430
Gly Ile Ile Thr Ser Lys Thr Lys Ser Leu Asp Lys Gly Tyr Asn Lys
            435                 440                 445
Ala Leu Asn Asp Leu Cys Ile Lys Val Asn Asn Trp Asp Leu Phe Phe
450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Asn Ile Ser Leu
                485                 490                 495
Asp Leu Ile Gln Gln Tyr Tyr Leu Thr Phe Asn Phe Asp Asn Glu Pro
            500                 505                 510
Glu Asn Ile Ser Ile Glu Asn Leu Ser Ser Asp Ile Ile Gly Gln Leu
            515                 520                 525
Glu Leu Met Pro Asn Ile Glu Arg Phe Pro Asn Gly Lys Lys Tyr Glu
            530                 535                 540
Leu Asp Lys Tyr Thr Met Phe His Tyr Leu Arg Ala Gln Glu Phe Glu
545                 550                 555                 560
His Gly Lys Ser Arg Ile Ala Leu Thr Asn Ser Val Asn Glu Ala Leu
            565                 570                 575
Leu Asn Pro Ser Arg Val Tyr Thr Phe Phe Ser Ser Asp Tyr Val Lys
            580                 585                 590
Lys Val Asn Lys Ala Thr Glu Ala Ala Met Phe Leu Gly Trp Val Glu
            595                 600                 605
Gln Leu Val Tyr Asp Phe Thr Asp Glu Thr Ser Glu Val Ser Thr Thr
            610                 615                 620
Asp Lys Ile Ala Asp Ile Thr Ile Ile Pro Tyr Ile Gly Pro Ala
625                 630                 635                 640
Leu Asn Ile Gly Asn Met Leu Tyr Lys Asp Asp Phe Val Gly Ala Leu
            645                 650                 655
Ile Phe Ser Gly Ala Val Ile Leu Leu Glu Phe Ile Pro Glu Ile Ala
            660                 665                 670
Ile Pro Val Leu Gly Thr Phe Ala Leu Val Ser Tyr Ile Ala Asn Lys
            675                 680                 685
Val Leu Thr Val Gln Thr Ile Asp Asn Ala Leu Ser Lys Arg Asn Glu
            690                 695                 700
Lys Trp Asp Glu Val Tyr Lys Tyr Ile Val Thr Asn Trp Leu Ala Lys
705                 710                 715                 720
Val Asn Thr Gln Ile Asp Leu Ile Arg Lys Lys Met Lys Glu Ala Leu
            725                 730                 735
Glu Asn Gln Ala Glu Ala Thr Lys Ala Ile Ile Asn Tyr Gln Tyr Asn
            740                 745                 750
Gln Tyr Thr Glu Glu Lys Asn Asn Ile Asn Phe Asn Ile Asp Asp
            755                 760                 765
Leu Ser Ser Lys Leu Asn Glu Ser Ile Asn Lys Ala Met Ile Asn Ile
            770                 775                 780
Asn Lys Phe Leu Asn Gln Cys Ser Val Ser Tyr Leu Met Asn Ser Met
785                 790                 795                 800
Ile Pro Tyr Gly Val Lys Arg Leu Glu Asp Phe Asp Ala Ser Leu Lys
            805                 810                 815
Asp Ala Leu Leu Lys Tyr Ile Tyr Asp Asn Arg Gly Thr Leu Ile Gly
            820                 825                 830
```

-continued

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
            885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
            915                 920                 925

Lys Asn Ala Ile Val Tyr Asn Ser Met Tyr Glu Asn Phe Ser Thr Ser
            930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
            965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
            995                 1000                1005

Asp Tyr Ile Asn Arg Trp Ile Phe Val Thr Ile Thr Asn Asn Arg
            1010                1015                1020

Leu Asn Asn Ser Lys Ile Tyr Ile Asn Gly Arg Leu Ile Asp Gln
            1025                1030                1035

Lys Pro Ile Ser Asn Leu Gly Asn Ile His Ala Ser Asn Asn Ile
            1040                1045                1050

Met Phe Lys Leu Asp Gly Cys Arg Asp Thr His Arg Tyr Ile Trp
            1055                1060                1065

Ile Lys Tyr Phe Asn Leu Phe Asp Lys Glu Leu Asn Glu Lys Glu
            1070                1075                1080

Ile Lys Asp Leu Tyr Asp Asn Gln Ser Asn Ser Gly Ile Leu Lys
            1085                1090                1095

Asp Phe Trp Gly Asp Tyr Leu Gln Tyr Asp Lys Pro Tyr Tyr Met
            1100                1105                1110

Leu Asn Leu Tyr Asp Pro Asn Lys Tyr Val Asp Val Asn Asn Val
            1115                1120                1125

Gly Ile Arg Gly Tyr Met Tyr Leu Lys Gly Pro Arg Gly Ser Val
            1130                1135                1140

Met Thr Thr Asn Ile Tyr Leu Asn Ser Ser Leu Tyr Arg Gly Thr
            1145                1150                1155

Lys Phe Ile Ile Lys Lys Tyr Ala Ser Gly Asn Lys Asp Asn Ile
            1160                1165                1170

Val Arg Asn Asn Asp Arg Val Tyr Ile Asn Val Val Val Lys Asn
            1175                1180                1185

Lys Glu Tyr Arg Leu Ala Thr Asn Ala Ser Gln Ala Gly Val Glu
            1190                1195                1200

Lys Ile Leu Ser Ala Leu Glu Ile Pro Asp Val Gly Asn Leu Ser
            1205                1210                1215

Gln Val Val Val Met Lys Ser Lys Asn Asp Gln Gly Ile Thr Asn
            1220                1225                1230

Lys Cys Lys Met Asn Leu Gln Asp Asn Asn Gly Asn Asp Ile Gly

```
              1235                1240                1245

Phe  Ile  Gly  Phe  His  Gln  Phe  Asn  Asn  Ile  Ala  Lys  Leu  Val  Ala
              1250                1255                1260

Ser  Asn  Trp  Tyr  Asn  Arg  Gln  Ile  Glu  Arg  Ser  Ser  Arg  Thr  Leu
              1265                1270                1275

Gly  Cys  Ser  Trp  Glu  Phe  Ile  Pro  Val  Asp  Asp  Gly  Trp  Gly  Glu
              1280                1285                1290

Arg  Pro  Leu
              1295

<210> SEQ ID NO 5
<211> LENGTH: 1296
<212> TYPE: PRT
<213> ORGANISM: Clostridium botulinum
<300> PUBLICATION INFORMATION:
<308> DATABASE ACCESSION NUMBER: CAA51824
<300> PUBLICATION INFORMATION:
<308> DATABASE ACCESSION NUMBER: I40645
<300> PUBLICATION INFORMATION:
<308> DATABASE ACCESSION NUMBER: Q45894

<400> SEQUENCE: 5

Met  Pro  Phe  Val  Asn  Lys  Gln  Phe  Asn  Tyr  Lys  Asp  Pro  Val  Asn  Gly
    1                  5                   10                  15

Val  Asp  Ile  Ala  Tyr  Ile  Lys  Ile  Pro  Asn  Ala  Gly  Gln  Met  Gln  Pro
                       20                  25                  30

Val  Lys  Ala  Phe  Lys  Ile  His  Asn  Lys  Ile  Trp  Val  Ile  Pro  Glu  Arg
                  35                  40                  45

Asp  Thr  Phe  Thr  Asn  Pro  Glu  Glu  Gly  Asp  Leu  Asn  Pro  Pro  Pro  Glu
         50                  55                  60

Ala  Lys  Gln  Val  Pro  Val  Ser  Tyr  Tyr  Asp  Ser  Thr  Tyr  Leu  Ser  Thr
    65                  70                  75                  80

Asp  Asn  Glu  Lys  Asp  Asn  Tyr  Leu  Lys  Gly  Val  Thr  Lys  Leu  Phe  Glu
                       85                  90                  95

Arg  Ile  Tyr  Ser  Thr  Asp  Leu  Gly  Arg  Met  Leu  Leu  Thr  Ser  Ile  Val
                  100                 105                 110

Arg  Gly  Ile  Pro  Phe  Trp  Gly  Gly  Ser  Thr  Ile  Asp  Thr  Glu  Leu  Lys
             115                 120                 125

Val  Ile  Asp  Thr  Asn  Cys  Ile  Asn  Val  Ile  Gln  Pro  Asp  Gly  Ser  Tyr
         130                 135                 140

Arg  Ser  Glu  Glu  Leu  Asn  Leu  Val  Ile  Ile  Gly  Pro  Ser  Ala  Asp  Ile
    145                 150                 155                 160

Ile  Gln  Phe  Glu  Cys  Lys  Ser  Phe  Gly  His  Asp  Val  Leu  Asn  Leu  Thr
                       165                 170                 175

Arg  Asn  Gly  Tyr  Gly  Ser  Thr  Gln  Tyr  Ile  Arg  Phe  Ser  Pro  Asp  Phe
                  180                 185                 190

Thr  Phe  Gly  Phe  Glu  Glu  Ser  Leu  Glu  Val  Asp  Thr  Asn  Pro  Leu  Leu
             195                 200                 205

Gly  Ala  Gly  Lys  Phe  Ala  Thr  Asp  Pro  Ala  Val  Thr  Leu  Ala  His  Glu
         210                 215                 220

Leu  Ile  His  Ala  Glu  His  Arg  Leu  Tyr  Gly  Ile  Ala  Ile  Asn  Pro  Asn
    225                 230                 235                 240

Arg  Val  Phe  Lys  Val  Asn  Thr  Asn  Ala  Tyr  Tyr  Glu  Met  Ser  Gly  Leu
                       245                 250                 255

Glu  Val  Ser  Phe  Glu  Glu  Leu  Arg  Thr  Phe  Gly  Gly  His  Asp  Ala  Lys
                  260                 265                 270
```

```
Phe Ile Asp Ser Leu Gln Glu Asn Glu Phe Arg Leu Tyr Tyr Asn
            275                 280                 285
Lys Phe Lys Asp Val Ala Ser Thr Leu Asn Lys Ala Lys Ser Ile Ile
290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
            340                 345                 350
Asn Phe Val Asn Phe Phe Lys Val Ile Asn Arg Lys Thr Tyr Leu Asn
            355                 360                 365
Phe Asp Lys Ala Val Phe Arg Ile Asn Ile Val Pro Asp Glu Asn Tyr
    370                 375                 380
Thr Ile Lys Asp Gly Phe Asn Leu Lys Gly Ala Asn Leu Ser Thr Asn
385                 390                 395                 400
Phe Asn Gly Gln Asn Thr Glu Ile Asn Ser Arg Asn Phe Thr Arg Leu
                405                 410                 415
Lys Asn Phe Thr Gly Leu Phe Glu Phe Tyr Lys Leu Leu Cys Val Arg
            420                 425                 430
Gly Ile Ile Pro Phe Lys Thr Lys Ser Leu Asp Glu Gly Tyr Asn Lys
            435                 440                 445
Ala Leu Asn Asp Leu Cys Ile Lys Val Asn Asn Trp Asp Leu Phe Phe
    450                 455                 460
Ser Pro Ser Glu Asp Asn Phe Thr Asn Asp Leu Asp Lys Val Glu Glu
465                 470                 475                 480
Ile Thr Ala Asp Thr Asn Ile Glu Ala Ala Glu Glu Asn Ile Ser Leu
                485                 490                 495
Asp Leu Ile Gln Gln Tyr Tyr Leu Thr Phe Asp Phe Asp Asn Glu Pro
            500                 505                 510
Glu Asn Ile Ser Ile Glu Asn Leu Ser Ser Asp Ile Ile Gly Gln Leu
            515                 520                 525
Glu Pro Met Pro Asn Ile Glu Arg Phe Pro Asn Gly Lys Lys Tyr Glu
    530                 535                 540
Leu Asp Lys Tyr Thr Met Phe His Tyr Leu Arg Ala Gln Glu Phe Glu
545                 550                 555                 560
His Gly Asp Ser Arg Ile Ile Leu Thr Asn Ser Ala Glu Glu Ala Leu
                565                 570                 575
Leu Lys Pro Asn Val Ala Tyr Thr Phe Phe Ser Ser Lys Tyr Val Lys
            580                 585                 590
Lys Ile Asn Lys Ala Val Glu Ala Phe Met Phe Leu Asn Trp Ala Glu
            595                 600                 605
Glu Leu Val Tyr Asp Phe Thr Asp Glu Thr Asn Glu Val Thr Thr Met
    610                 615                 620
Asp Lys Ile Ala Asp Ile Thr Ile Val Pro Tyr Ile Gly Pro Ala
625                 630                 635                 640
Leu Asn Ile Gly Asn Met Leu Ser Lys Gly Glu Phe Val Glu Ala Ile
                645                 650                 655
Ile Phe Thr Gly Val Val Ala Met Leu Glu Phe Ile Pro Glu Tyr Ala
            660                 665                 670
Leu Pro Val Phe Gly Thr Phe Ala Ile Val Ser Tyr Ile Ala Asn Lys
            675                 680                 685
Val Leu Thr Val Gln Thr Ile Asn Asn Ala Leu Ser Lys Arg Asn Glu
```

```
                    690                 695                 700
Lys Trp Asp Glu Val Tyr Lys Tyr Thr Val Thr Asn Trp Leu Ala Lys
705                 710                 715                 720

Val Asn Thr Gln Ile Asp Leu Ile Arg Glu Lys Met Lys Lys Ala Leu
                    725                 730                 735

Glu Asn Gln Ala Glu Ala Thr Lys Ala Ile Ile Asn Tyr Gln Tyr Asn
                    740                 745                 750

Gln Tyr Thr Glu Glu Lys Asn Asn Ile Asn Phe Asn Ile Asp Asp
                    755                 760                 765

Leu Ser Ser Lys Leu Asn Glu Ser Ile Asn Ser Ala Met Ile Asn Ile
                    770                 775                 780

Asn Lys Phe Leu Asp Gln Cys Ser Val Ser Tyr Leu Met Asn Ser Met
785                 790                 795                 800

Ile Pro Tyr Ala Val Lys Arg Leu Lys Asp Phe Asp Ala Ser Val Arg
                    805                 810                 815

Asp Val Leu Leu Lys Tyr Ile Tyr Asp Asn Arg Gly Thr Leu Val Leu
                    820                 825                 830

Gln Val Asp Arg Leu Lys Asp Glu Val Asn Asn Thr Leu Ser Ala Asp
                    835                 840                 845

Ile Pro Phe Gln Leu Ser Lys Tyr Val Asp Asn Lys Lys Leu Leu Ser
                    850                 855                 860

Thr Phe Thr Glu Tyr Ile Lys Asn Ile Val Asn Thr Ser Ile Leu Ser
865                 870                 875                 880

Ile Val Tyr Lys Lys Asp Asp Leu Ile Asp Leu Ser Arg Tyr Gly Ala
                    885                 890                 895

Lys Ile Asn Ile Gly Asp Arg Val Tyr Tyr Asp Ser Ile Asp Lys Asn
                    900                 905                 910

Gln Ile Lys Leu Ile Asn Leu Glu Ser Ser Thr Ile Glu Val Ile Leu
                    915                 920                 925

Lys Asn Ala Ile Val Tyr Asn Ser Met Tyr Glu Asn Phe Ser Thr Ser
                    930                 935                 940

Phe Trp Ile Lys Ile Pro Lys Tyr Phe Ser Lys Ile Asn Leu Asn Asn
945                 950                 955                 960

Glu Tyr Thr Ile Ile Asn Cys Ile Glu Asn Asn Ser Gly Trp Lys Val
                    965                 970                 975

Ser Leu Asn Tyr Gly Glu Ile Ile Trp Thr Leu Gln Asp Asn Lys Gln
                    980                 985                 990

Asn Ile Gln Arg Val Val Phe Lys Tyr Ser Gln Met Val Asn Ile Ser
                    995                 1000                1005

Asp Tyr Ile Asn Arg Trp Ile Phe Val Thr Ile Thr Asn Asn Arg
     1010                1015                1020

Leu Thr Lys Ser Lys Ile Tyr Ile Asn Gly Arg Leu Ile Asp Gln
     1025                1030                1035

Lys Pro Ile Ser Asn Leu Gly Asn Ile His Ala Ser Asn Lys Ile
     1040                1045                1050

Met Phe Lys Leu Asp Gly Cys Arg Asp Pro Arg Tyr Ile Met
     1055                1060                1065

Ile Lys Tyr Phe Asn Leu Phe Asp Lys Glu Leu Asn Glu Lys Glu
     1070                1075                1080

Ile Lys Asp Leu Tyr Asp Ser Gln Ser Asn Ser Gly Ile Leu Lys
     1085                1090                1095

Asp Phe Trp Gly Asn Tyr Leu Gln Tyr Asp Lys Pro Tyr Tyr Met
     1100                1105                1110
```

```
Leu Asn Leu Phe Asp Pro Asn Lys Tyr Val Asp Val Asn Asn Ile
    1115                1120                1125

Gly Ile Arg Gly Tyr Met Tyr Leu Lys Gly Pro Arg Gly Ser Val
    1130                1135                1140

Val Thr Thr Asn Ile Tyr Leu Asn Ser Thr Leu Tyr Glu Gly Thr
    1145                1150                1155

Lys Phe Ile Ile Lys Lys Tyr Ala Ser Gly Asn Glu Asp Asn Ile
    1160                1165                1170

Val Arg Asn Asn Asp Arg Val Tyr Ile Asn Val Val Val Lys Asn
    1175                1180                1185

Lys Glu Tyr Arg Leu Ala Thr Asn Ala Ser Gln Ala Gly Val Glu
    1190                1195                1200

Lys Ile Leu Ser Ala Leu Glu Ile Pro Asp Val Gly Asn Leu Ser
    1205                1210                1215

Gln Val Val Val Met Lys Ser Lys Asp Asp Gln Gly Ile Arg Asn
    1220                1225                1230

Lys Cys Lys Met Asn Leu Gln Asp Asn Asn Gly Asn Asp Ile Gly
    1235                1240                1245

Phe Ile Gly Phe His Leu Tyr Asp Asn Ile Ala Lys Leu Val Ala
    1250                1255                1260

Ser Asn Trp Tyr Asn Arg Gln Val Gly Lys Ala Ser Arg Thr Phe
    1265                1270                1275

Gly Cys Ser Trp Glu Phe Ile Pro Val Asp Asp Gly Trp Gly Glu
    1280                1285                1290

Ser Ser Leu
    1295

<210> SEQ ID NO 6
<211> LENGTH: 1291
<212> TYPE: PRT
<213> ORGANISM: Clostridium botulinum
<300> PUBLICATION INFORMATION:
<308> DATABASE ACCESSION NUMBER: AAL11498
<300> PUBLICATION INFORMATION:
<308> DATABASE ACCESSION NUMBER: AAL11499

<400> SEQUENCE: 6

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Met Gly Arg
                20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
                100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140
```

```
Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asn Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
                260                 265                 270

Gly Gly Gln Asp Pro Ser Ile Ile Ser Pro Ser Thr Asp Lys Ser Ile
            275                 280                 285

Tyr Asp Lys Val Leu Gln Asn Phe Arg Gly Ile Val Asp Arg Leu Asn
290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asn Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Ala Tyr Asn Thr Gln Asn Asn
465                 470                 475                 480

Tyr Ile Glu Asn Asp Phe Ser Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Tyr Val Pro Val Tyr Lys Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
```

```
                 565                 570                 575
Tyr Ile Lys Thr Ala Asn Lys Val Val Glu Ala Gly Leu Phe Ala Gly
                580                 585                 590

Trp Val Lys Gln Ile Val Asn Asp Phe Val Ile Glu Ala Asn Lys Ser
                595                 600                 605

Ser Thr Met Asp Lys Ile Ala Asp Ile Ser Leu Ile Val Pro Tyr Ile
            610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
                660                 665                 670

Asp Asn Lys Asn Lys Ile Ile Glu Thr Ile Asn Ser Ala Leu Thr Lys
                675                 680                 685

Arg Asp Glu Lys Trp Ile Asp Met Tyr Gly Leu Ile Val Ala Gln Trp
            690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Lys Tyr Asn Ile Tyr Ser Glu Lys Glu Arg Ser Asn Ile Asn Ile Asp
                740                 745                 750

Phe Asn Asp Val Asn Ser Lys Leu Asn Glu Gly Ile Asn Gln Ala Ile
            755                 760                 765

Asp Asn Ile Asn Asn Phe Ile Asn Glu Cys Ser Val Ser Tyr Leu Met
        770                 775                 780

Lys Lys Met Ile Pro Leu Ala Val Glu Lys Leu Leu Asp Phe Asp Asn
785                 790                 795                 800

Thr Leu Arg Lys Asn Leu Leu Asn Tyr Ile Asp Glu Asn Lys Leu Tyr
            805                 810                 815

Leu Ile Gly Ser Ala Glu Tyr Glu Lys Ser Lys Val Asp Lys Tyr Leu
            820                 825                 830

Lys Thr Ser Ile Pro Phe Asp Leu Ser Thr Tyr Thr Asn Asn Thr Ile
            835                 840                 845

Leu Ile Glu Ile Phe Asn Lys Tyr Asn Ser Asp Ile Leu Asn Asn Ile
            850                 855                 860

Ile Leu Asn Leu Arg Tyr Arg Asp Asn Lys Leu Ile Asp Leu Ser Gly
865                 870                 875                 880

Tyr Gly Ala Lys Val Glu Val Tyr Asp Gly Val Lys Leu Asn Asp Lys
                885                 890                 895

Asn Gln Phe Lys Leu Thr Ser Ser Ala Asn Ser Lys Ile Arg Val Thr
                900                 905                 910

Gln Asn Gln Asn Ile Ile Phe Asn Ser Met Phe Leu Asp Phe Ser Val
            915                 920                 925

Ser Phe Trp Ile Arg Ile Pro Lys Tyr Lys Asn Asp Gly Ile Gln Asn
        930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Met Ile Ile Trp Thr Leu Ile
                965                 970                 975

Asp Ile Asn Gly Lys Ile Lys Ser Val Phe Phe Glu Tyr Ser Ile Lys
                980                 985                 990
```

Glu Asp Ile Ser Glu Tyr Ile Asn Arg Trp Phe Phe Val Thr Ile Thr
              995                 1000                1005

Asn Asn Ser Asp Asn Ala Lys Ile Tyr Ile Asn Gly Lys Leu Glu
        1010                1015                1020

Ser His Ile Asp Ile Arg Asp Ile Arg Glu Val Ile Ala Asn Asp
        1025                1030                1035

Glu Ile Ile Phe Lys Leu Asp Gly Asn Ile Asp Arg Thr Gln Phe
        1040                1045                1050

Ile Trp Met Lys Tyr Phe Ser Ile Phe Asn Thr Glu Leu Ser Gln
        1055                1060                1065

Ser Asn Ile Glu Glu Ile Tyr Lys Ile Gln Ser Tyr Ser Glu Tyr
        1070                1075                1080

Leu Lys Asp Phe Trp Gly Asn Pro Leu Met Tyr Asn Lys Glu Tyr
        1085                1090                1095

Tyr Met Phe Asn Ala Gly Asn Lys Asn Ser Tyr Ile Lys Leu Lys
        1100                1105                1110

Lys Asp Ser Ser Val Gly Glu Ile Leu Thr Arg Ser Lys Tyr Asn
        1115                1120                1125

Gln Asn Ser Lys Tyr Ile Asn Tyr Arg Asp Leu Tyr Ile Gly Glu
        1130                1135                1140

Lys Phe Ile Ile Arg Arg Lys Ser Asn Ser Gln Ser Ile Asn Asp
        1145                1150                1155

Asp Ile Val Arg Lys Glu Asp Tyr Ile Tyr Leu Asp Phe Phe Asn
        1160                1165                1170

Leu Asn Gln Glu Trp Arg Val Tyr Met Tyr Lys Tyr Phe Lys Lys
        1175                1180                1185

Glu Glu Glu Lys Leu Phe Leu Ala Pro Ile Ser Asp Ser Asp Glu
        1190                1195                1200

Phe Tyr Asn Thr Ile Gln Ile Lys Glu Tyr Asp Glu Gln Pro Thr
        1205                1210                1215

Tyr Ser Cys Gln Leu Leu Phe Lys Lys Asp Glu Glu Ser Thr Asp
        1220                1225                1230

Glu Ile Gly Leu Ile Gly Ile His Arg Phe Tyr Glu Ser Gly Ile
        1235                1240                1245

Val Phe Lys Glu Tyr Lys Asp Tyr Phe Cys Ile Ser Lys Trp Tyr
        1250                1255                1260

Leu Lys Glu Val Lys Arg Lys Pro Tyr Asn Ser Lys Leu Gly Cys
        1265                1270                1275

Asn Trp Gln Phe Ile Pro Lys Asp Glu Gly Trp Thr Glu
        1280                1285                1290

<210> SEQ ID NO 7
<211> LENGTH: 1291
<212> TYPE: PRT
<213> ORGANISM: Clostridium botulinum
<300> PUBLICATION INFORMATION:
<308> DATABASE ACCESSION NUMBER: CAA73968

<400> SEQUENCE: 7

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Met Gly Arg
            20                  25                  30

Tyr Tyr Lys Ala Phe Lys Ile Thr Asp Arg Ile Trp Ile Ile Pro Glu
        35                  40                  45

```
Arg Tyr Thr Phe Gly Tyr Lys Pro Glu Asp Phe Asn Lys Ser Ser Gly
     50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                 85                  90                  95

Asn Arg Ile Lys Ser Lys Pro Leu Gly Glu Lys Leu Leu Glu Met Ile
             100                 105                 110

Ile Asn Gly Ile Pro Tyr Leu Gly Asp Arg Arg Val Pro Leu Glu Glu
             115                 120                 125

Phe Asn Thr Asn Ile Ala Ser Val Thr Val Asn Lys Leu Ile Ser Asn
130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                 165                 170                 175

Ile Gln Asn His Phe Ala Ser Arg Glu Gly Phe Gly Gly Ile Met Gln
             180                 185                 190

Met Lys Phe Cys Pro Glu Tyr Val Ser Val Phe Asn Asn Val Gln Glu
         195                 200                 205

Asn Lys Gly Ala Ser Ile Phe Asn Arg Arg Gly Tyr Phe Ser Asp Pro
     210                 215                 220

Ala Leu Ile Leu Met His Glu Leu Ile His Val Leu His Gly Leu Tyr
225                 230                 235                 240

Gly Ile Lys Val Asn Asp Leu Pro Ile Val Pro Asn Glu Lys Lys Phe
                 245                 250                 255

Phe Met Gln Ser Thr Asp Ala Ile Gln Ala Glu Glu Leu Tyr Thr Phe
             260                 265                 270

Gly Gly Gln Asp Pro Ser Ile Ile Ser Pro Ser Thr Asp Lys Ser Ile
         275                 280                 285

Tyr Asp Lys Val Leu Gln Asn Phe Arg Gly Ile Val Asp Arg Leu Asn
     290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                 325                 330                 335

Lys Tyr Ser Ile Asp Val Glu Ser Phe Asp Lys Leu Tyr Lys Ser Leu
             340                 345                 350

Met Phe Gly Phe Thr Glu Thr Asn Ile Ala Glu Asn Tyr Lys Ile Lys
         355                 360                 365

Thr Arg Ala Ala Tyr Phe Ser Asp Ser Leu Pro Pro Val Lys Ile Lys
     370                 375                 380

Asn Leu Leu Asp Asn Glu Ile Tyr Thr Ile Glu Glu Gly Phe Asn Ile
385                 390                 395                 400

Ser Asp Lys Asn Met Glu Lys Glu Tyr Arg Gly Gln Asn Lys Ala Ile
                 405                 410                 415

Asn Lys Gln Ala Tyr Glu Glu Ile Ser Lys Glu His Leu Ala Val Tyr
             420                 425                 430

Lys Ile Gln Met Cys Lys Ser Val Lys Ala Pro Gly Ile Cys Ile Asp
         435                 440                 445

Val Asp Asn Glu Asp Leu Phe Phe Ile Ala Asp Lys Asn Ser Phe Ser
450                 455                 460
```

-continued

```
Asp Asp Leu Ser Lys Asn Glu Arg Ile Ala Tyr Asn Thr Gln Asn Asn
465                 470                 475                 480

Tyr Ile Glu Asn Asp Phe Ser Ile Asn Glu Leu Ile Leu Asp Thr Asp
                485                 490                 495

Leu Ile Ser Lys Ile Glu Leu Pro Ser Glu Asn Thr Glu Ser Leu Thr
                500                 505                 510

Asp Phe Asn Val Tyr Val Pro Val Tyr Lys Lys Gln Pro Ala Ile Lys
                515                 520                 525

Lys Ile Phe Thr Asp Glu Asn Thr Ile Phe Gln Tyr Leu Tyr Ser Gln
                530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
                580                 585                 590

Trp Val Lys Gln Ile Val Asp Asp Phe Val Ile Glu Ala Asn Lys Ser
                595                 600                 605

Ser Thr Met Asp Lys Ile Ala Asp Ile Ser Leu Ile Val Pro Tyr Ile
                610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
                660                 665                 670

Asp Asn Lys Asn Lys Ile Ile Glu Thr Ile Asn Ser Ala Leu Thr Lys
                675                 680                 685

Arg Asp Glu Lys Trp Ile Asp Met Tyr Gly Leu Ile Val Ala Gln Trp
                690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Lys Tyr Asn Ile Tyr Ser Glu Lys Glu Arg Ser Asn Ile Asn Ile Asp
                740                 745                 750

Phe Asn Asp Val Asn Ser Lys Leu Asn Glu Gly Ile Asn Gln Ala Ile
                755                 760                 765

Asp Asn Ile Asn Asn Phe Ile Asn Glu Cys Ser Val Ser Tyr Leu Met
                770                 775                 780

Lys Lys Met Ile Pro Leu Ala Val Glu Lys Leu Leu Asp Phe Asp Asn
785                 790                 795                 800

Thr Leu Arg Lys Asn Leu Leu Asn Tyr Ile Asp Glu Asn Lys Leu Tyr
                805                 810                 815

Leu Ile Gly Ser Ala Glu Tyr Glu Lys Ser Lys Val Asp Lys Tyr Leu
                820                 825                 830

Lys Thr Ser Ile Pro Phe Asp Leu Ser Thr Tyr Thr Asn Asn Thr Ile
                835                 840                 845

Leu Ile Glu Ile Phe Asn Lys Tyr Asn Ser Asp Ile Leu Asn Asn Ile
                850                 855                 860

Ile Leu Asn Leu Arg Tyr Arg Asp Asn Lys Leu Ile Asp Leu Ser Gly
865                 870                 875                 880

Tyr Gly Ala Lys Val Glu Val Tyr Asp Gly Val Lys Leu Asn Asp Lys
```

-continued

```
                885                 890                 895
Asn Gln Phe Lys Leu Thr Ser Ser Ala Asn Ser Lys Ile Arg Val Ile
            900                 905                 910
Gln Asn Gln Asn Ile Ile Phe Asn Ser Met Phe Leu Asp Phe Ser Val
            915                 920                 925
Ser Phe Trp Ile Arg Ile Pro Lys Tyr Lys Asn Asp Gly Ile Gln Asn
            930                 935                 940
Tyr Ile His Asn Glu Tyr Thr Ile Ile Asn Cys Met Lys Asn Asn Ser
945                 950                 955                 960
Gly Trp Lys Ile Ser Ile Arg Gly Asn Met Ile Ile Trp Thr Leu Ile
            965                 970                 975
Asp Ile Asn Gly Lys Ile Lys Ser Val Phe Phe Glu Tyr Ser Ile Lys
            980                 985                 990
Glu Asp Ile Ser Glu Tyr Ile Asn Arg Trp Phe Phe Val Thr Ile Thr
            995                 1000                1005
Asn Asn Ser Asp Asn Ala Lys Ile Tyr Ile Asn Gly Lys Leu Glu
            1010                1015                1020
Ser His Ile Asp Ile Arg Asp Ile Arg Glu Val Ile Ala Asn Asp
            1025                1030                1035
Glu Ile Ile Phe Lys Leu Asp Gly Asn Ile Asp Arg Thr Gln Phe
            1040                1045                1050
Ile Trp Met Lys Tyr Phe Ser Ile Phe Asn Thr Glu Leu Ser Gln
            1055                1060                1065
Ser Asn Ile Glu Glu Ile Tyr Lys Ile Gln Ser Tyr Ser Glu Tyr
            1070                1075                1080
Leu Lys Asp Phe Trp Gly Asn Pro Leu Met Tyr Asn Lys Glu Tyr
            1085                1090                1095
Tyr Met Phe Asn Ala Gly Asn Lys Asn Ser Tyr Ile Lys Leu Lys
            1100                1105                1110
Lys Asp Ser Ser Val Gly Glu Ile Leu Thr Arg Ser Lys Tyr Asn
            1115                1120                1125
Gln Asn Ser Lys Tyr Ile Asn Tyr Arg Asp Leu Tyr Ile Gly Glu
            1130                1135                1140
Lys Phe Ile Ile Arg Arg Lys Ser Asn Ser Gln Ser Ile Asn Asp
            1145                1150                1155
Asp Ile Val Arg Lys Glu Asp Tyr Ile Tyr Leu Asp Phe Phe Asn
            1160                1165                1170
Leu Asn Gln Glu Trp Arg Val Tyr Met Tyr Lys Tyr Phe Lys Lys
            1175                1180                1185
Glu Glu Glu Lys Leu Phe Leu Ala Pro Ile Ser Asp Ser Asp Glu
            1190                1195                1200
Phe Tyr Asn Thr Ile Gln Ile Lys Glu Tyr Asp Glu Gln Pro Thr
            1205                1210                1215
Tyr Ser Cys Gln Leu Leu Phe Lys Lys Asp Glu Glu Ser Thr Asp
            1220                1225                1230
Glu Ile Gly Leu Ile Gly Ile His Arg Phe Tyr Glu Ser Gly Ile
            1235                1240                1245
Val Phe Lys Glu Tyr Lys Asp Tyr Phe Cys Ile Ser Lys Trp Tyr
            1250                1255                1260
Leu Lys Glu Val Lys Arg Lys Pro Tyr Asn Ser Lys Leu Gly Cys
            1265                1270                1275
Asn Trp Gln Phe Ile Pro Lys Asp Glu Gly Trp Thr Glu
            1280                1285                1290
```

<210> SEQ ID NO 8
<211> LENGTH: 1291
<212> TYPE: PRT
<213> ORGANISM: Clostridium botulinum
<300> PUBLICATION INFORMATION:
<308> DATABASE ACCESSION NUMBER: AAK97132

<400> SEQUENCE: 8

```
Met Ser Val Thr Ile Asn Asn Phe Asn Tyr Asn Asp Pro Ile Asp Asn
1               5                   10                  15

Asp Asn Ile Ile Met Met Glu Pro Pro Phe Ala Arg Gly Thr Gly Arg
                20                  25                  30

Tyr Tyr Lys Ala Phe Lys Ile Thr Asp Arg Ile Trp Ile Ile Pro Glu
            35                  40                  45

Arg Tyr Thr Phe Gly Tyr Lys Pro Glu Asp Phe Asn Lys Ser Ser Gly
        50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
210                 215                 220

Ala Leu Ile Leu Met His Glu Leu Ile His Val Leu His Gly Leu Tyr
225                 230                 235                 240

Gly Ile Lys Val Asn Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Ser Pro Ser Thr Asp Lys Ser Ile
        275                 280                 285

Tyr Asp Lys Val Leu Gln Asn Phe Arg Gly Ile Val Asp Arg Leu Asn
290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365
```

-continued

Thr Arg Ala Ser Tyr Phe Ser Asp Ser Leu Pro Val Lys Ile Lys
370             375             380

Asn Leu Leu Asp Asn Glu Ile Tyr Thr Ile Glu Glu Gly Phe Asn Ile
385             390             395             400

Ser Asp Lys Asn Met Glu Lys Glu Tyr Arg Gly Gln Asn Lys Ala Ile
        405             410             415

Asn Lys Gln Ala Tyr Glu Glu Ile Ser Lys Glu His Leu Ala Val Tyr
        420             425             430

Lys Ile Gln Met Cys Lys Ser Val Lys Ala Pro Gly Ile Cys Ile Asp
        435             440             445

Val Asp Asn Glu Asp Leu Phe Phe Ile Ala Asp Lys Asn Ser Phe Ser
        450             455             460

Asp Asp Leu Ser Lys Asn Glu Arg Ile Ala Tyr Asn Thr Gln Asn Asn
465             470             475             480

Tyr Ile Asp Asn Asp Phe Ser Ile Asn Glu Leu Ile Leu Asp Thr Asp
            485             490             495

Leu Ile Ser Lys Ile Glu Leu Pro Ser Glu Asn Thr Glu Ser Leu Thr
            500             505             510

Asp Phe Asn Val Tyr Val Pro Glu Tyr Lys Lys Gln Pro Ala Ile Lys
        515             520             525

Lys Ile Phe Thr Asp Glu Asn Thr Ile Phe Gln Tyr Leu Tyr Ser Gln
        530             535             540

Thr Phe Pro Leu Asp Ile Arg Asp Ile Ser Leu Thr Ser Ser Phe Asp
545             550             555             560

Asp Ala Leu Leu Phe Ser Asn Lys Val Tyr Ser Phe Phe Ser Met Asp
            565             570             575

Tyr Ile Lys Thr Ala Asn Lys Val Val Glu Ala Gly Leu Phe Ala Gly
            580             585             590

Trp Val Lys Gln Ile Val Asp Asp Phe Val Ile Glu Ala Asn Lys Ser
            595             600             605

Ser Thr Met Asp Lys Ile Ala Asp Ile Ser Leu Ile Val Pro Tyr Ile
        610             615             620

Gly Leu Ala Leu Asn Val Gly Asn Glu Thr Ala Lys Gly Asn Phe Glu
625             630             635             640

Asn Ala Phe Glu Ile Ala Gly Ala Ser Ile Leu Leu Glu Phe Ile Pro
            645             650             655

Glu Leu Leu Ile Pro Val Val Gly Ala Phe Leu Leu Glu Ser Tyr Ile
            660             665             670

Asp Asn Lys Asn Lys Ile Ile Glu Thr Ile Asn Ser Ala Leu Thr Lys
        675             680             685

Arg Asp Glu Lys Trp Ile Asp Met Tyr Gly Leu Ile Val Ala Gln Trp
690             695             700

Leu Ser Thr Val Asn Thr Gln Phe Tyr Thr Ile Lys Glu Gly Met Tyr
705             710             715             720

Lys Ala Leu Asn Tyr Gln Ala Gln Ala Leu Glu Glu Ile Ile Lys Tyr
            725             730             735

Lys Tyr Asn Ile Tyr Ser Glu Lys Glu Arg Ser Asn Ile Asn Ile Asp
            740             745             750

Phe Asn Asp Val Asn Ser Lys Leu Asn Glu Gly Ile Asn Gln Ala Ile
        755             760             765

Asp Asn Ile Asn Asn Phe Ile Asn Glu Cys Ser Val Ser Tyr Leu Met
        770             775             780

```
Lys Lys Met Ile Pro Leu Ala Val Glu Lys Leu Leu Asp Phe Asp Asn
785                 790                 795                 800

Thr Leu Arg Lys Asn Leu Leu Asn Tyr Ile Asp Glu Asn Lys Leu Tyr
            805                 810                 815

Leu Ile Gly Ser Ala Glu Tyr Glu Lys Ser Lys Val Asp Lys Tyr Leu
                820                 825                 830

Lys Thr Ser Ile Pro Phe Asp Leu Ser Thr Tyr Thr Asn Asn Thr Ile
            835                 840                 845

Leu Ile Glu Ile Phe Asn Lys Tyr Asn Ser Asp Ile Leu Asn Asn Ile
        850                 855                 860

Ile Leu Asn Leu Arg Tyr Arg Asp Asn Lys Leu Ile Asp Leu Ser Gly
865                 870                 875                 880

Tyr Gly Ala Lys Val Glu Val Tyr Asp Gly Val Lys Leu Asn Asp Lys
                885                 890                 895

Asn Gln Phe Lys Leu Thr Ser Ser Ala Asn Ser Lys Ile Arg Val Ile
                900                 905                 910

Gln Asn Gln Asn Ile Ile Phe Asn Ser Met Phe Leu Asp Phe Ser Val
            915                 920                 925

Ser Phe Trp Ile Arg Ile Pro Lys Tyr Lys Asn Asp Gly Ile Gln Asn
        930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Met Ile Ile Trp Thr Leu Ile
                965                 970                 975

Asp Ile Asn Gly Lys Ile Lys Ser Val Phe Phe Glu Tyr Ser Ile Lys
            980                 985                 990

Glu Asp Ile Ser Glu Tyr Ile Asn Arg Trp Phe Phe Val Thr Ile Thr
        995                 1000                1005

Asn Asn Ser Asp Asn Ala Lys Ile Tyr Ile Asn Gly Lys Leu Glu
    1010                1015                1020

Ser His Ile Asp Ile Arg Asp Ile Arg Glu Val Ile Ala Asn Asp
    1025                1030                1035

Glu Ile Ile Phe Lys Leu Asp Gly Asn Ile Asp Arg Thr Gln Phe
    1040                1045                1050

Ile Trp Met Lys Tyr Phe Ser Ile Phe Asn Thr Glu Leu Ser Gln
    1055                1060                1065

Ser Asn Ile Glu Glu Ile Tyr Lys Ile Gln Ser Tyr Ser Glu Tyr
    1070                1075                1080

Leu Lys Asp Phe Trp Gly Asn Pro Leu Met Tyr Asn Lys Glu Tyr
    1085                1090                1095

Tyr Met Phe Asn Ala Gly Asn Lys Asn Ser Tyr Ile Lys Leu Lys
    1100                1105                1110

Lys Asp Ser Pro Val Gly Glu Ile Leu Thr Arg Ser Lys Tyr Asn
    1115                1120                1125

Gln Asn Ser Lys Tyr Ile Asn Tyr Arg Asp Leu Tyr Ile Gly Glu
    1130                1135                1140

Lys Phe Ile Ile Arg Arg Lys Ser Asn Ser Gln Ser Ile Asn Asp
    1145                1150                1155

Asp Ile Val Arg Lys Glu Asp Tyr Ile Tyr Leu Asp Phe Phe Asn
    1160                1165                1170

Leu Asn Gln Glu Trp Arg Val Tyr Ile Tyr Lys Tyr Phe Lys Lys
    1175                1180                1185

Glu Glu Glu Lys Leu Phe Leu Ala Pro Ile Ser Asp Ser Asp Glu
```

```
                        1190              1195              1200

Phe Tyr Asn Thr Ile Gln Ile Lys Glu Tyr Asp Glu Gln Pro Thr
    1205              1210              1215

Tyr Ser Cys Gln Leu Leu Phe Lys Lys Asp Glu Glu Ser Thr Asp
    1220              1225              1230

Glu Ile Gly Leu Ile Gly Ile His Arg Phe Tyr Glu Ser Gly Ile
    1235              1240              1245

Val Phe Lys Glu Tyr Lys Asp Tyr Phe Cys Ile Ser Lys Trp Tyr
    1250              1255              1260

Leu Lys Glu Val Lys Arg Lys Pro Tyr Asn Ser Lys Leu Gly Cys
    1265              1270              1275

Asn Trp Gln Phe Ile Pro Lys Asp Glu Gly Trp Thr Glu
    1280              1285              1290

<210> SEQ ID NO 9
<211> LENGTH: 1291
<212> TYPE: PRT
<213> ORGANISM: Clostridium botulinum
<300> PUBLICATION INFORMATION:
<308> DATABASE ACCESSION NUMBER: A48940
<300> PUBLICATION INFORMATION:
<308> DATABASE ACCESSION NUMBER: AAA23211
<300> PUBLICATION INFORMATION:
<308> DATABASE ACCESSION NUMBER: P10844

<400> SEQUENCE: 9

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240
```

```
Gly Ile Lys Val Asp Asp Leu Pro Ile Val Pro Asn Glu Lys Lys Phe
            245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
            275                 280                 285

Tyr Asp Lys Val Leu Gln Asn Phe Arg Gly Ile Val Asp Arg Leu Asn
            290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
            325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
            355                 360                 365

Thr Arg Ala Ser Tyr Phe Ser Asp Ser Leu Pro Pro Val Lys Ile Lys
            370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
            405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
            435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
            485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
            515                 520                 525

Lys Ile Phe Thr Asp Glu Asn Thr Ile Phe Gln Tyr Leu Tyr Ser Gln
            530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
            565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
            595                 600                 605

Asn Thr Met Asp Lys Ile Ala Asp Ile Ser Leu Ile Val Pro Tyr Ile
            610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
            645                 650                 655

Glu Leu Leu Ile Pro Val Val Gly Ala Phe Leu Leu Glu Ser Tyr Ile
```

```
            660                 665                 670
Asp Asn Lys Asn Lys Ile Ile Lys Thr Ile Asp Asn Ala Leu Thr Lys
            675                 680                 685
Arg Asn Glu Lys Trp Ser Asp Met Tyr Gly Leu Ile Val Ala Gln Trp
            690                 695                 700
Leu Ser Thr Val Asn Thr Gln Phe Tyr Thr Ile Lys Glu Gly Met Tyr
705                 710                 715                 720
Lys Ala Leu Asn Tyr Gln Ala Gln Ala Leu Glu Glu Ile Ile Lys Tyr
                725                 730                 735
Arg Tyr Asn Ile Tyr Ser Glu Lys Glu Lys Ser Asn Ile Asn Ile Asp
                740                 745                 750
Phe Asn Asp Ile Asn Ser Lys Leu Asn Glu Gly Ile Asn Gln Ala Ile
            755                 760                 765
Asp Asn Ile Asn Asn Phe Ile Asn Gly Cys Ser Val Ser Tyr Leu Met
            770                 775                 780
Lys Lys Met Ile Pro Leu Ala Val Glu Lys Leu Leu Asp Phe Asp Asn
785                 790                 795                 800
Thr Leu Lys Lys Asn Leu Leu Asn Tyr Ile Asp Glu Asn Lys Leu Tyr
                805                 810                 815
Leu Ile Gly Ser Ala Glu Tyr Glu Lys Ser Lys Val Asn Lys Tyr Leu
                820                 825                 830
Lys Thr Ile Met Pro Phe Asp Leu Ser Ile Tyr Thr Asn Asp Thr Ile
            835                 840                 845
Leu Ile Glu Met Phe Asn Lys Tyr Asn Ser Glu Ile Leu Asn Asn Ile
850                 855                 860
Ile Leu Asn Leu Arg Tyr Lys Asp Asn Asn Leu Ile Asp Leu Ser Gly
865                 870                 875                 880
Tyr Gly Ala Lys Val Glu Val Tyr Asp Gly Val Glu Leu Asn Asp Lys
                885                 890                 895
Asn Gln Phe Lys Leu Thr Ser Ser Ala Asn Ser Lys Ile Arg Val Thr
            900                 905                 910
Gln Asn Gln Asn Ile Ile Phe Asn Ser Val Phe Leu Asp Phe Ser Val
            915                 920                 925
Ser Phe Trp Ile Arg Ile Pro Lys Tyr Lys Asn Asp Gly Ile Gln Asn
930                 935                 940
Tyr Ile His Asn Glu Tyr Thr Ile Ile Asn Cys Met Lys Asn Asn Ser
945                 950                 955                 960
Gly Trp Lys Ile Ser Ile Arg Gly Asn Arg Ile Ile Trp Thr Leu Ile
                965                 970                 975
Asp Ile Asn Gly Lys Thr Lys Ser Val Phe Phe Glu Tyr Asn Ile Arg
            980                 985                 990
Glu Asp Ile Ser Glu Tyr Ile Asn Arg Trp Phe Phe Val Thr Ile Thr
            995                 1000                1005
Asn Asn Leu Asn Asn Ala Lys Ile Tyr Ile Asn Gly Lys Leu Glu
            1010                1015                1020
Ser Asn Thr Asp Ile Lys Asp Ile Arg Glu Val Ile Ala Asn Gly
            1025                1030                1035
Glu Ile Ile Phe Lys Leu Asp Gly Asp Ile Asp Arg Thr Gln Phe
            1040                1045                1050
Ile Trp Met Lys Tyr Phe Ser Ile Phe Asn Thr Glu Leu Ser Gln
            1055                1060                1065
Ser Asn Ile Glu Glu Arg Tyr Lys Ile Gln Ser Tyr Ser Glu Tyr
            1070                1075                1080
```

-continued

```
Leu Lys Asp Phe Trp Gly Asn Pro Leu Met Tyr Asn Lys Glu Tyr
    1085            1090                1095

Tyr Met Phe Asn Ala Gly Asn Lys Asn Ser Tyr Ile Lys Leu Lys
    1100            1105                1110

Lys Asp Ser Pro Val Gly Glu Ile Leu Thr Arg Ser Lys Tyr Asn
    1115            1120                1125

Gln Asn Ser Lys Tyr Ile Asn Tyr Arg Asp Leu Tyr Ile Gly Glu
    1130            1135                1140

Lys Phe Ile Ile Arg Arg Lys Ser Asn Ser Gln Ser Ile Asn Asp
    1145            1150                1155

Asp Ile Val Arg Lys Glu Asp Tyr Ile Tyr Leu Asp Phe Phe Asn
    1160            1165                1170

Leu Asn Gln Glu Trp Arg Val Tyr Thr Tyr Lys Tyr Phe Lys Lys
    1175            1180                1185

Glu Glu Glu Lys Leu Phe Leu Ala Pro Ile Ser Asp Ser Asp Glu
    1190            1195                1200

Phe Tyr Asn Thr Ile Gln Ile Lys Glu Tyr Asp Glu Gln Pro Thr
    1205            1210                1215

Tyr Ser Cys Gln Leu Leu Phe Lys Lys Asp Glu Glu Ser Thr Asp
    1220            1225                1230

Glu Ile Gly Leu Ile Gly Ile His Arg Phe Tyr Glu Ser Gly Ile
    1235            1240                1245

Val Phe Glu Glu Tyr Lys Asp Tyr Phe Cys Ile Ser Lys Trp Tyr
    1250            1255                1260

Leu Lys Glu Val Lys Arg Lys Pro Tyr Asn Leu Lys Leu Gly Cys
    1265            1270                1275

Asn Trp Gln Phe Ile Pro Lys Asp Glu Gly Trp Thr Glu
    1280            1285                1290

<210> SEQ ID NO 10
<211> LENGTH: 1291
<212> TYPE: PRT
<213> ORGANISM: Clostridium botulinum
<300> PUBLICATION INFORMATION:
<308> DATABASE ACCESSION NUMBER: BAC22064

<400> SEQUENCE: 10

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
                20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140
```

```
Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
            165                 170                 175

Ile Gln Asn His Phe Ala Ser Arg Glu Gly Phe Gly Gly Ile Met Gln
        180                 185                 190

Met Lys Phe Cys Pro Glu Tyr Val Ser Val Phe Asn Asn Val Gln Glu
    195                 200                 205

Asn Lys Gly Ala Ser Ile Phe Asn Arg Arg Gly Tyr Phe Ser Asp Pro
210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
370                 375                 380

Asn Leu Leu Asp Asn Glu Ile Tyr Thr Ile Glu Glu Gly Phe Asn Ile
385                 390                 395                 400

Ser Asp Lys Asn Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Arg Ala Pro Gly Ile Cys Ile Asp
        435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Glu Tyr Asp Thr Gln Ser Asn
465                 470                 475                 480

Tyr Ile Glu Asn Arg Ser Ser Ile Asp Glu Leu Ile Leu Asp Thr Asn
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
530                 535                 540

Thr Phe Pro Leu Asp Ile Arg Asp Ile Ser Leu Thr Ser Ser Phe Asp
545                 550                 555                 560
```

-continued

Asp Ala Leu Leu Phe Ser Asn Lys Val Tyr Ser Phe Ser Met Asp
                        565             570             575

Tyr Ile Lys Thr Ala Asn Lys Val Val Glu Ala Gly Leu Phe Ala Gly
            580             585             590

Trp Val Lys Gln Ile Val Asp Asp Phe Val Ile Glu Ala Asn Lys Ser
        595             600             605

Ser Thr Met Asp Lys Ile Ala Asp Ile Ser Leu Ile Val Pro Tyr Ile
    610             615             620

Gly Leu Ala Leu Asn Val Gly Asn Glu Thr Lys Gly Asn Phe Glu
625             630             635             640

Asn Ala Phe Glu Ile Ala Gly Ser Ile Leu Leu Glu Phe Ile Pro
            645             650             655

Glu Leu Leu Ile Pro Val Val Gly Ala Phe Leu Leu Glu Ser Tyr Ile
        660             665             670

Asp Asn Lys Asn Lys Ile Ile Lys Thr Ile Asp Asn Ala Leu Thr Lys
    675             680             685

Arg Asp Glu Lys Trp Ile Asp Met Tyr Gly Leu Ile Val Ala Gln Trp
690             695             700

Leu Ser Thr Val Asn Thr Gln Phe Tyr Thr Ile Lys Glu Gly Met Tyr
705             710             715             720

Lys Ala Leu Asn Tyr Gln Ala Gln Ala Leu Glu Glu Ile Ile Lys Tyr
            725             730             735

Lys Tyr Asn Ile Tyr Ser Glu Lys Glu Lys Ser Asn Ile Asn Ile Asp
        740             745             750

Phe Asn Asp Ile Asn Ser Lys Leu Asn Glu Gly Ile Asn Gln Ala Val
    755             760             765

Asp Asn Ile Asn Asn Phe Ile Asn Glu Cys Ser Val Ser Tyr Leu Met
770             775             780

Lys Lys Met Ile Pro Leu Ala Val Glu Lys Leu Leu Asp Phe Asp Asn
785             790             795             800

Thr Leu Lys Lys Asn Leu Leu Asn Tyr Ile Asp Glu Asn Lys Leu Tyr
            805             810             815

Leu Ile Gly Ser Ala Glu Tyr Glu Lys Ser Lys Val Asp Lys His Leu
        820             825             830

Lys Thr Ile Ile Pro Phe Asp Leu Ser Met Tyr Thr Asn Asn Thr Ile
    835             840             845

Leu Ile Glu Ile Phe Asn Lys Tyr Asn Ser Glu Ile Leu Asn Asn Ile
850             855             860

Ile Leu Asn Leu Arg Tyr Arg Asp Asn Asn Leu Ile Asp Leu Ser Gly
865             870             875             880

Tyr Gly Ala Asn Val Glu Val Tyr Asp Gly Val Glu Leu Asn Asp Lys
            885             890             895

Asn Gln Phe Lys Leu Thr Ser Ser Thr Asn Ser Glu Ile Arg Val Thr
        900             905             910

Gln Asn Gln Asn Ile Ile Phe Asn Ser Met Phe Leu Asp Phe Ser Val
    915             920             925

Ser Phe Trp Ile Arg Ile Pro Lys Tyr Lys Asn Asp Gly Ile Gln Asn
930             935             940

Tyr Ile His Asn Glu Tyr Thr Ile Ile Asn Cys Ile Lys Asn Asn Ser
945             950             955             960

Gly Trp Lys Ile Ser Ile Arg Gly Asn Arg Ile Ile Trp Thr Leu Thr
            965             970             975

Asp Ile Asn Gly Lys Thr Lys Ser Val Phe Phe Glu Tyr Ser Ile Arg

Glu Asp Ile Ser Asp Tyr Ile Asn Arg Trp Phe Phe Val Thr Ile Thr
            980             985             990

Asn Asn Ser Asp Asn Ala Lys Ile Tyr Ile Asn Gly Lys Leu Glu
        995             1000            1005

Ser Asn Ile Asp Ile Lys Asp Ile Gly Glu Val Ile Ala Asn Gly
    1010            1015            1020

Glu Ile Ile Phe Lys Leu Asp Gly Asp Ile Asp Arg Thr Gln Phe
    1025            1030            1035

Ile Trp Met Lys Tyr Phe Ser Ile Phe Asn Thr Glu Leu Ser Gln
    1040            1045            1050

Ser Asn Ile Lys Glu Ile Tyr Lys Ile Gln Ser Tyr Ser Glu Tyr
    1055            1060            1065

Leu Lys Asp Phe Trp Gly Asn Pro Leu Met Tyr Asn Lys Glu Tyr
    1070            1075            1080

Tyr Met Phe Asn Ala Gly Asn Lys Asn Ser Tyr Ile Lys Leu Lys
    1085            1090            1095

Lys Asp Ser Ser Val Gly Glu Ile Leu Thr Arg Ser Lys Tyr Asn
    1100            1105            1110

Gln Asn Ser Asn Tyr Ile Asn Tyr Arg Asn Leu Tyr Ile Gly Glu
    1115            1120            1125

Lys Phe Ile Ile Arg Arg Lys Ser Asn Ser Gln Ser Ile Asn Asp
    1130            1135            1140

Asp Ile Val Arg Lys Glu Asp Tyr Ile Tyr Leu Asp Phe Phe Asn
    1145            1150            1155

Ser Asn Arg Glu Trp Arg Val Tyr Ala Tyr Lys Asp Phe Lys Glu
    1160            1165            1170

Glu Glu Lys Lys Leu Phe Leu Ala Asn Ile Tyr Asp Ser Asn Glu
    1175            1180            1185

Phe Tyr Lys Thr Ile Gln Ile Lys Glu Tyr Asp Glu Gln Pro Thr
    1190            1195            1200

Tyr Ser Cys Gln Leu Leu Phe Lys Lys Asp Glu Glu Ser Thr Asp
    1205            1210            1215

Glu Ile Gly Leu Ile Gly Ile His Arg Phe Tyr Glu Ser Gly Ile
    1220            1225            1230

Val Leu Lys Asp Tyr Lys Asn Tyr Phe Cys Ile Ser Lys Trp Tyr
    1235            1240            1245

Leu Lys Glu Val Lys Arg Lys Pro Tyr Asn Pro Asn Leu Gly Cys
    1250            1255            1260

Asn Trp Gln Phe Ile Pro Lys Asp Glu Gly Trp Ile Glu
    1265            1270            1275

<210> SEQ ID NO 11
<211> LENGTH: 1291
<212> TYPE: PRT
<213> ORGANISM: Clostridium botulinum
<300> PUBLICATION INFORMATION:
<308> DATABASE ACCESSION NUMBER: CAA50482
<300> PUBLICATION INFORMATION:
<308> DATABASE ACCESSION NUMBER: I40631

<400> SEQUENCE: 11

Met Pro Val Thr Ile Asn Asn Phe Asn Tyr Asn Asp Pro Ile Asp Asn
1               5                   10                  15

Asp Asn Ile Ile Met Met Glu Pro Pro Phe Ala Arg Gly Thr Gly Arg
            20                  25                  30

-continued

```
Tyr Tyr Lys Ala Phe Lys Ile Thr Asp Arg Ile Trp Ile Ile Pro Glu
         35                  40                  45

Arg Tyr Thr Phe Gly Tyr Lys Pro Glu Asp Phe Asn Lys Ser Ser Gly
     50                  55                  60

Ile Phe Asn Arg Asp Val Cys Glu Tyr Tyr Asp Pro Asp Tyr Leu Asn
 65                  70                  75                  80

Thr Asn Asp Lys Lys Asn Ile Phe Phe Gln Thr Leu Ile Lys Leu Phe
                 85                  90                  95

Asn Arg Ile Lys Ser Lys Pro Leu Gly Glu Lys Leu Leu Glu Met Ile
                100                 105                 110

Ile Asn Gly Ile Pro Tyr Leu Gly Asp Arg Arg Val Pro Leu Glu Glu
            115                 120                 125

Phe Asn Thr Asn Ile Ala Ser Val Thr Val Asn Lys Leu Ile Ser Asn
        130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Thr Ile Gln Ala Glu Glu Leu Tyr Thr Phe
        260                 265                 270

Gly Gly Gln Asp Pro Ser Ile Ile Ser Pro Ser Thr Asp Lys Ser Ile
            275                 280                 285

Tyr Asp Lys Val Leu Gln Asn Phe Arg Gly Ile Val Asp Arg Leu Asn
290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asn Lys Leu Tyr Lys Ser Leu
        340                 345                 350

Met Leu Gly Phe Thr Glu Ile Asn Ile Ala Glu Asn Tyr Lys Ile Lys
            355                 360                 365

Thr Arg Ala Ser Tyr Phe Ser Asp Ser Leu Pro Pro Val Lys Ile Lys
370                 375                 380

Asn Leu Leu Asp Asn Glu Ile Tyr Thr Ile Glu Glu Gly Phe Asn Ile
385                 390                 395                 400

Ser Asp Lys Asn Met Gly Lys Glu Tyr Arg Gly Gln Asn Lys Ala Ile
                405                 410                 415

Asn Lys Gln Ala Tyr Glu Glu Ile Ser Lys Glu His Leu Ala Val Tyr
        420                 425                 430

Lys Ile Gln Met Cys Lys Ser Val Lys Val Pro Gly Ile Cys Ile Asp
            435                 440                 445
```

```
Val Asp Asn Glu Asn Leu Phe Phe Ile Ala Asp Lys Asn Ser Phe Ser
450                 455                 460

Asp Asp Leu Ser Lys Asn Glu Arg Val Glu Tyr Asn Thr Gln Asn Asn
465                 470                 475                 480

Tyr Ile Gly Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Val Phe Thr Asp Glu Asn Thr Ile Phe Gln Tyr Leu Tyr Ser Gln
530                 535                 540

Thr Phe Pro Leu Asn Ile Arg Asp Ile Ser Leu Thr Ser Ser Phe Asp
545                 550                 555                 560

Asp Ala Leu Leu Val Ser Ser Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asp Asp Phe Val Ile Glu Ala Asn Lys Ser
        595                 600                 605

Ser Thr Met Asp Lys Ile Ala Asp Ile Ser Leu Ile Val Pro Tyr Ile
610                 615                 620

Gly Leu Ala Leu Asn Val Gly Asp Glu Thr Ala Lys Gly Asn Phe Glu
625                 630                 635                 640

Ser Ala Phe Glu Ile Ala Gly Ser Ser Ile Leu Leu Glu Phe Ile Pro
                645                 650                 655

Glu Leu Leu Ile Pro Val Val Gly Val Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Val Glu Lys Trp Ile Asp Met Tyr Gly Leu Ile Val Ala Gln Trp
690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Lys Tyr Asn Ile Tyr Ser Glu Glu Lys Ser Asn Ile Asn Ile Asn
            740                 745                 750

Phe Asn Asp Ile Asn Ser Lys Leu Asn Asp Gly Ile Asn Gln Ala Met
        755                 760                 765

Asp Asn Ile Asn Asp Phe Ile Asn Glu Cys Ser Val Ser Tyr Leu Met
770                 775                 780

Lys Lys Met Ile Pro Leu Ala Val Lys Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Val Glu Asp Glu Lys Ser Lys Val Asp Lys Tyr Leu
            820                 825                 830

Lys Thr Ile Ile Pro Phe Asp Leu Ser Thr Tyr Ser Asn Ile Glu Ile
        835                 840                 845

Leu Ile Lys Ile Phe Asn Lys Tyr Asn Ser Glu Ile Leu Asn Asn Ile
850                 855                 860

Ile Leu Asn Leu Arg Tyr Arg Asp Asn Asn Leu Ile Asp Leu Ser Gly
```

```
                865                 870                 875                 880
Tyr Gly Ala Lys Val Glu Val Tyr Asp Gly Val Lys Leu Asn Asp Lys
                    885                 890                 895
Asn Gln Phe Lys Leu Thr Ser Ser Ala Asp Ser Lys Ile Arg Val Thr
                    900                 905                 910
Gln Asn Gln Asn Ile Ile Phe Asn Ser Met Phe Leu Asp Phe Ser Val
                    915                 920                 925
Ser Phe Trp Ile Arg Ile Pro Lys Tyr Arg Asn Asp Asp Ile Gln Asn
                    930                 935                 940
Tyr Ile His Asn Glu Tyr Thr Ile Ile Asn Cys Met Lys Asn Asn Ser
945                 950                 955                 960
Gly Trp Lys Ile Ser Ile Arg Gly Asn Arg Ile Ile Trp Thr Leu Ile
                    965                 970                 975
Asp Ile Asn Gly Lys Thr Lys Ser Val Phe Phe Glu Tyr Asn Ile Arg
                    980                 985                 990
Glu Asp Ile Ser Glu Tyr Ile Asn Arg Trp Phe Phe Val Thr Ile Thr
                    995                1000                1005
Asn Asn Leu Asp Asn Ala Lys Ile Tyr Ile Asn Gly Thr Leu Glu
1010                1015                1020
Ser Asn Met Asp Ile Lys Asp Ile Gly Glu Val Ile Val Asn Gly
1025                1030                1035
Glu Ile Thr Phe Lys Leu Asp Gly Asp Val Asp Arg Thr Gln Phe
1040                1045                1050
Ile Trp Met Lys Tyr Phe Ser Ile Phe Asn Thr Gln Leu Asn Gln
1055                1060                1065
Ser Asn Ile Lys Glu Ile Tyr Lys Ile Gln Ser Tyr Ser Glu Tyr
1070                1075                1080
Leu Lys Asp Phe Trp Gly Asn Pro Leu Met Tyr Asn Lys Glu Tyr
1085                1090                1095
Tyr Met Phe Asn Ala Gly Asn Lys Asn Ser Tyr Ile Lys Leu Val
1100                1105                1110
Lys Asp Ser Ser Val Gly Glu Ile Leu Ile Arg Ser Lys Tyr Asn
1115                1120                1125
Gln Asn Ser Asn Tyr Ile Asn Tyr Arg Asn Leu Tyr Ile Gly Glu
1130                1135                1140
Lys Phe Ile Ile Arg Arg Glu Ser Asn Ser Gln Ser Ile Asn Asp
1145                1150                1155
Asp Ile Val Arg Lys Glu Asp Tyr Ile His Leu Asp Leu Val Leu
1160                1165                1170
His His Glu Glu Trp Arg Val Tyr Ala Tyr Lys Tyr Phe Lys Glu
1175                1180                1185
Gln Glu Glu Lys Leu Phe Leu Ser Ile Ile Ser Asp Ser Asn Glu
1190                1195                1200
Phe Tyr Lys Thr Ile Glu Ile Lys Glu Tyr Asp Glu Gln Pro Ser
1205                1210                1215
Tyr Ser Cys Gln Leu Leu Phe Lys Lys Asp Glu Glu Ser Thr Asp
1220                1225                1230
Asp Ile Gly Leu Ile Gly Ile His Arg Phe Tyr Glu Ser Gly Val
1235                1240                1245
Leu Arg Lys Lys Tyr Lys Asp Tyr Phe Cys Ile Ser Lys Trp Tyr
1250                1255                1260
Leu Lys Glu Val Lys Arg Lys Pro Tyr Lys Ser Asn Leu Gly Cys
1265                1270                1275
```

```
Asn Trp Gln Phe Ile Pro Lys Asp Glu Gly Trp Thr Glu
    1280            1285            1290

<210> SEQ ID NO 12
<211> LENGTH: 1291
<212> TYPE: PRT
<213> ORGANISM: Clostridium phage
<300> PUBLICATION INFORMATION:
<308> DATABASE ACCESSION NUMBER: A49777
<300> PUBLICATION INFORMATION:
<308> DATABASE ACCESSION NUMBER: BAA14235
<300> PUBLICATION INFORMATION:
<308> DATABASE ACCESSION NUMBER: CAA51313
<300> PUBLICATION INFORMATION:
<308> DATABASE ACCESSION NUMBER: S46431

<400> SEQUENCE: 12

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320
```

Glu Tyr Lys Gln Lys Leu Ile Arg Lys Tyr Arg Phe Val Val Glu Ser
                    325                 330                 335

Ser Gly Glu Val Thr Val Asn Arg Asn Lys Phe Val Glu Leu Tyr Asn
                340                 345                 350

Glu Leu Thr Gln Ile Phe Thr Glu Phe Asn Tyr Ala Lys Ile Tyr Asn
            355                 360                 365

Val Gln Asn Arg Lys Ile Tyr Leu Ser Asn Val Tyr Thr Pro Val Thr
        370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
                420                 425                 430

Phe Thr Lys Phe Cys His Lys Ala Ile Asp Gly Arg Ser Leu Tyr Asn
            435                 440                 445

Lys Thr Leu Asp Cys Arg Glu Leu Leu Val Lys Asn Thr Asp Leu Pro
        450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
                500                 505                 510

Asp Leu Leu Tyr Pro Ser Ile Asp Ser Glu Ser Glu Ile Leu Pro Gly
            515                 520                 525

Glu Asn Gln Val Phe Tyr Asp Asn Arg Thr Gln Asn Val Asp Tyr Leu
        530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
                580                 585                 590

Val Gln Gly Gly Leu Phe Leu Met Trp Ala Asn Asp Val Val Glu Asp
            595                 600                 605

Phe Thr Thr Asn Ile Leu Arg Lys Asp Thr Leu Asp Lys Ile Ser Asp
        610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
                660                 665                 670

Ala Phe Val Ile Tyr Ser Lys Val Gln Glu Arg Asn Glu Ile Ile Lys
            675                 680                 685

Thr Ile Asp Asn Cys Leu Glu Gln Arg Ile Lys Arg Trp Lys Asp Ser
        690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                725                 730                 735

-continued

Ala Ile Lys Ala Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
            755                 760                 765

Asp Val Lys Ile Ser Glu Ala Met Asn Asn Ile Asn Lys Phe Ile Arg
770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
            805                 810                 815

Leu Ile Asp Ser His Asn Ile Ile Leu Val Gly Glu Val Asp Lys Leu
            820                 825                 830

Lys Ala Lys Val Asn Asn Ser Phe Gln Asn Thr Ile Pro Phe Asn Ile
            835                 840                 845

Phe Ser Tyr Thr Asn Asn Ser Leu Leu Lys Asp Ile Ile Asn Glu Tyr
850                 855                 860

Phe Asn Asn Ile Asn Asp Ser Lys Ile Leu Ser Leu Gln Asn Arg Lys
865                 870                 875                 880

Asn Thr Leu Val Asp Thr Ser Gly Tyr Asn Ala Glu Val Ser Glu Glu
            885                 890                 895

Gly Asp Val Gln Leu Asn Pro Ile Phe Pro Phe Asp Phe Lys Leu Gly
            900                 905                 910

Ser Ser Gly Glu Asp Arg Gly Lys Val Ile Val Thr Gln Asn Glu Asn
            915                 920                 925

Ile Val Tyr Asn Ser Met Tyr Glu Ser Phe Ser Ile Ser Phe Trp Ile
            930                 935                 940

Arg Ile Asn Lys Trp Val Ser Asn Leu Pro Gly Tyr Thr Ile Ile Asp
945                 950                 955                 960

Ser Val Lys Asn Asn Ser Gly Trp Ser Ile Gly Ile Ile Ser Asn Phe
            965                 970                 975

Leu Val Phe Thr Leu Lys Gln Asn Glu Asp Ser Glu Gln Ser Ile Asn
            980                 985                 990

Phe Ser Tyr Asp Ile Ser Asn Asn Ala Pro Gly Tyr Asn Lys Trp Phe
            995                 1000                1005

Phe Val Thr Val Thr Asn Asn Met Met Gly Asn Met Lys Ile Tyr
    1010                1015                1020

Ile Asn Gly Lys Leu Ile Asp Thr Ile Lys Val Lys Glu Leu Thr
    1025                1030                1035

Gly Ile Asn Phe Ser Lys Thr Ile Thr Phe Glu Ile Asn Lys Ile
    1040                1045                1050

Pro Asp Thr Gly Leu Ile Thr Ser Asp Ser Asp Asn Ile Asn Met
    1055                1060                1065

Trp Ile Arg Asp Phe Tyr Ile Phe Ala Lys Glu Leu Asp Gly Lys
    1070                1075                1080

Asp Ile Asn Ile Leu Phe Asn Ser Leu Gln Tyr Thr Asn Val Val
    1085                1090                1095

Lys Asp Tyr Trp Gly Asn Asp Leu Arg Tyr Asn Lys Glu Tyr Tyr
    1100                1105                1110

Met Val Asn Ile Asp Tyr Leu Asn Arg Tyr Met Tyr Ala Asn Ser
    1115                1120                1125

Arg Gln Ile Val Phe Asn Thr Arg Arg Asn Asn Asn Asp Phe Asn
    1130                1135                1140

Glu Gly Tyr Lys Ile Ile Ile Lys Arg Ile Arg Gly Asn Thr Asn

```
                 1145            1150            1155
Asp Thr Arg Val Arg Gly Gly Asp Ile Leu Tyr Phe Asp Met Thr
         1160            1165            1170

Ile Asn Asn Lys Ala Tyr Asn Leu Phe Met Lys Asn Glu Thr Met
         1175            1180            1185

Tyr Ala Asp Asn His Ser Thr Glu Asp Ile Tyr Ala Ile Gly Leu
         1190            1195            1200

Arg Glu Gln Thr Lys Asp Ile Asn Asp Asn Ile Ile Phe Gln Ile
         1205            1210            1215

Gln Pro Met Asn Asn Thr Tyr Tyr Tyr Ala Ser Gln Ile Phe Lys
         1220            1225            1230

Ser Asn Phe Asn Gly Glu Asn Ile Ser Gly Ile Cys Ser Ile Gly
         1235            1240            1245

Thr Tyr Arg Phe Arg Leu Gly Gly Asp Trp Tyr Arg His Asn Tyr
         1250            1255            1260

Leu Val Pro Thr Val Lys Gln Gly Asn Tyr Ala Ser Leu Leu Glu
         1265            1270            1275

Ser Thr Ser Thr His Trp Gly Phe Val Pro Val Ser Glu
         1280            1285            1290

<210> SEQ ID NO 13
<211> LENGTH: 1291
<212> TYPE: PRT
<213> ORGANISM: Clostridium botulinum
<300> PUBLICATION INFORMATION:
<308> DATABASE ACCESSION NUMBER: BAB71749

<400> SEQUENCE: 13

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
```

```
            210                 215                 220
Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                    245                 250                 255

Phe Tyr Ser Gln Tyr Asn Val Lys Leu Glu Tyr Ala Glu Ile Tyr Ala
                260                 265                 270

Phe Gly Gly Pro Thr Ile Asp Leu Ile Pro Lys Ser Ala Arg Lys Tyr
                275                 280                 285

Phe Glu Glu Lys Ala Leu Asp Tyr Tyr Arg Ser Ile Ala Lys Arg Leu
            290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
                340                 345                 350

Glu Leu Thr Gln Ile Phe Thr Glu Phe Asn Tyr Ala Lys Ile Tyr Asn
            355                 360                 365

Val Gln Asn Arg Lys Ile Tyr Leu Ser Asn Val Tyr Thr Pro Val Thr
            370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                    405                 410                 415

Arg Asn Pro Ala Leu Arg Lys Val Asn Pro Glu Asn Met Leu Tyr Leu
                420                 425                 430

Phe Thr Lys Phe Cys His Lys Ala Ile Asp Gly Arg Ser Leu Tyr Asn
            435                 440                 445

Lys Thr Leu Asp Cys Arg Glu Leu Leu Val Lys Asn Thr Asp Leu Pro
            450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                    485                 490                 495

Val Asp Gln Val Ile Leu Ser Lys Asn Thr Ser Glu His Gly Gln Leu
                500                 505                 510

Asp Leu Leu Tyr Pro Ser Ile Asp Ser Glu Ser Glu Ile Leu Pro Gly
            515                 520                 525

Glu Asn Gln Val Phe Tyr Asp Asn Arg Thr Gln Asn Val Asp Tyr Leu
            530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
                580                 585                 590

Val Gln Gly Gly Leu Phe Leu Met Trp Ala Asn Asp Val Val Glu Asp
            595                 600                 605

Phe Thr Thr Asn Ile Leu Arg Lys Asp Thr Leu Asp Lys Ile Ser Asp
            610                 615                 620

Val Ser Ala Ile Ile Pro Tyr Ile Gly Pro Ala Leu Asn Ile Ser Asn
625                 630                 635                 640
```

```
Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
            660                 665                 670

Ala Phe Val Ile Tyr Ser Lys Val Gln Glu Arg Asn Glu Ile Ile Lys
            675                 680                 685

Thr Ile Asp Asn Cys Leu Glu Gln Arg Ile Lys Arg Trp Lys Asp Ser
        690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                725                 730                 735

Ala Ile Lys Ala Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
        755                 760                 765

Asp Val Lys Ile Ser Glu Ala Met Asn Asn Ile Asn Lys Phe Ile Arg
        770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                805                 810                 815

Leu Ile Asp Ser His Asn Ile Ile Leu Val Gly Glu Val Asp Lys Leu
            820                 825                 830

Lys Ala Lys Val Asn Asn Ser Phe Gln Asn Thr Ile Pro Phe Asn Ile
        835                 840                 845

Phe Ser Tyr Thr Asn Asn Ser Leu Leu Lys Asp Ile Ile Asn Glu Tyr
        850                 855                 860

Phe Asn Asn Ile Asn Asp Ser Lys Ile Leu Ser Leu Gln Asn Arg Lys
865                 870                 875                 880

Asn Thr Leu Val Asp Thr Ser Gly Tyr Asn Ala Glu Val Ser Glu Glu
                885                 890                 895

Gly Asp Val Gln Leu Asn Pro Ile Phe Pro Phe Asp Phe Lys Leu Gly
            900                 905                 910

Ser Ser Gly Glu Asp Arg Gly Lys Val Ile Val Thr Gln Asn Glu Asn
        915                 920                 925

Ile Val Tyr Asn Ser Met Tyr Glu Ser Phe Ser Ile Ser Phe Trp Ile
        930                 935                 940

Arg Ile Asn Lys Trp Val Ser Asn Leu Pro Gly Tyr Thr Ile Ile Asp
945                 950                 955                 960

Ser Val Lys Asn Asn Ser Gly Trp Ser Ile Gly Ile Ile Ser Asn Phe
                965                 970                 975

Leu Val Phe Thr Leu Lys Gln Asn Glu Asp Ser Glu Gln Ser Ile Asn
            980                 985                 990

Phe Ser Tyr Asp Ile Ser Asn Asn Ala Pro Gly Tyr Asn Lys Trp Phe
        995                 1000                1005

Phe Val Thr Val Thr Asn Asn Met Met Gly Asn Met Lys Ile Tyr
        1010                1015                1020

Ile Asn Gly Lys Leu Ile Asp Thr Ile Lys Val Lys Glu Leu Thr
        1025                1030                1035

Gly Ile Asn Phe Ser Lys Thr Ile Thr Phe Glu Ile Asn Lys Ile
        1040                1045                1050
```

Pro Asp Thr Gly Leu Ile Thr Ser Asp Ser Asp Asn Ile Asn Met
    1055                1060                1065

Trp Ile Arg Asp Phe Tyr Ile Phe Ala Lys Glu Leu Asp Gly Lys
    1070                1075                1080

Asp Ile Asn Ile Leu Phe Asn Ser Leu Gln Tyr Thr Asn Val Val
    1085                1090                1095

Lys Asp Tyr Trp Gly Asn Asp Leu Arg Tyr Asn Lys Glu Tyr Tyr
    1100                1105                1110

Met Val Asn Ile Asp Tyr Leu Asn Arg Tyr Met Tyr Ala Asn Ser
    1115                1120                1125

Arg Gln Ile Val Phe Asn Thr Arg Arg Asn Asn Asn Asp Phe Asn
    1130                1135                1140

Glu Gly Tyr Lys Ile Ile Ile Lys Arg Ile Arg Gly Asn Thr Asn
    1145                1150                1155

Asp Thr Arg Val Arg Gly Gly Asp Ile Leu Tyr Phe Asp Met Thr
    1160                1165                1170

Ile Asn Asn Lys Ala Tyr Asn Leu Phe Met Lys Asn Glu Thr Met
    1175                1180                1185

Tyr Ala Asp Asn His Ser Thr Glu Asp Ile Tyr Ala Ile Gly Leu
    1190                1195                1200

Arg Glu Gln Thr Lys Asp Ile Asn Asp Asn Ile Ile Phe Gln Ile
    1205                1210                1215

Gln Pro Met Asn Asn Thr Tyr Tyr Tyr Ala Ser Gln Ile Phe Lys
    1220                1225                1230

Ser Asn Phe Asn Gly Glu Asn Ile Ser Gly Ile Cys Ser Ile Gly
    1235                1240                1245

Thr Tyr Arg Phe Arg Leu Gly Gly Asp Trp Tyr Arg His Asn Tyr
    1250                1255                1260

Leu Val Pro Thr Val Lys Gln Gly Asn Tyr Ala Ser Leu Leu Glu
    1265                1270                1275

Ser Thr Ser Thr His Trp Gly Phe Val Pro Val Ser Glu
    1280                1285                1290

<210> SEQ ID NO 14
<211> LENGTH: 1291
<212> TYPE: PRT
<213> ORGANISM: Clostridium botulinum

<400> SEQUENCE: 14

Met Pro Ile Thr Ile Asn Asn Phe Asn Tyr Ser Asp Pro Val Asp
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
            35                  40                  45

Arg Phe Ser Arg Asn Ser Asn Pro Asn Leu Asn Lys Pro Pro Arg Val
        50                  55                  60

Thr Ser Pro Lys Ser Gly Tyr Tyr Asp Pro Asn Tyr Leu Ser Thr Asp
65                  70                  75                  80

Ser Asp Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
            115                 120                 125

```
Phe Asp Val Asp Phe Asn Ser Val Asp Val Lys Thr Arg Gln Gly Asn
    130                 135                 140
Asn Trp Val Lys Thr Gly Ser Ile Asn Pro Ser Val Ile Ile Thr Gly
145                 150                 155                 160
Pro Arg Glu Asn Ile Ile Asp Pro Glu Thr Ser Thr Phe Lys Leu Thr
                165                 170                 175
Asn Asn Thr Phe Ala Ala Gln Glu Gly Phe Gly Ala Leu Ser Ile Ile
                180                 185                 190
Ser Ile Ser Pro Arg Phe Met Leu Thr Tyr Ser Asn Ala Thr Asn Asp
        195                 200                 205
Val Gly Glu Gly Arg Phe Ser Lys Ser Glu Phe Cys Met Asp Pro Ile
    210                 215                 220
Leu Ile Leu Met His Glu Leu Asn His Ala Met His Asn Leu Tyr Gly
225                 230                 235                 240
Ile Ala Ile Pro Asn Asp Gln Thr Ile Ser Ser Val Thr Ser Asn Ile
                245                 250                 255
Phe Tyr Ser Gln Tyr Asn Val Lys Leu Glu Tyr Ala Glu Ile Tyr Ala
        260                 265                 270
Phe Gly Gly Pro Thr Ile Asp Leu Ile Pro Lys Ser Ala Arg Lys Tyr
    275                 280                 285
Phe Glu Glu Lys Ala Leu Asp Tyr Tyr Arg Ser Ile Ala Lys Arg Leu
290                 295                 300
Asn Ser Ile Thr Thr Ala Asn Pro Ser Ser Phe Asn Lys Tyr Ile Gly
305                 310                 315                 320
Glu Tyr Lys Gln Lys Leu Ile Arg Lys Tyr Arg Phe Val Val Glu Ser
                325                 330                 335
Ser Gly Glu Val Thr Val Asn Arg Asn Lys Phe Val Glu Leu Tyr Asn
        340                 345                 350
Glu Leu Thr Gln Ile Phe Thr Glu Phe Asn Tyr Ala Lys Ile Tyr Asn
    355                 360                 365
Val Gln Asn Arg Lys Ile Tyr Leu Ser Asn Val Tyr Thr Pro Val Thr
370                 375                 380
Ala Asn Ile Leu Asp Asp Asn Val Tyr Asp Ile Gln Asn Gly Phe Asn
385                 390                 395                 400
Ile Pro Lys Ser Asn Leu Asn Val Leu Phe Met Gly Gln Asn Leu Ser
                405                 410                 415
Arg Asn Pro Ala Leu Arg Lys Val Asn Pro Glu Asn Met Leu Tyr Leu
        420                 425                 430
Phe Thr Lys Phe Cys His Lys Ala Ile Asp Gly Arg Ser Leu Tyr Asn
    435                 440                 445
Lys Thr Leu Asp Cys Arg Glu Leu Leu Val Lys Asn Thr Asp Leu Pro
450                 455                 460
Phe Ile Gly Asp Ile Ser Asp Val Lys Thr Asp Ile Phe Leu Arg Lys
465                 470                 475                 480
Asp Ile Asn Glu Glu Thr Glu Val Ile Tyr Tyr Pro Asp Asn Val Ser
                485                 490                 495
Val Asp Gln Val Ile Leu Ser Lys Asn Thr Ser Glu His Gly Gln Leu
        500                 505                 510
Asp Leu Leu Tyr Pro Ser Ile Asp Ser Glu Ser Glu Ile Leu Pro Gly
    515                 520                 525
Glu Asn Gln Val Phe Tyr Asp Asn Arg Thr Gln Asn Val Asp Tyr Leu
530                 535                 540
```

```
Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
            565                 570                 575

Lys Val Tyr Thr Tyr Phe Pro Thr Leu Ala Asn Lys Val Asn Ala Gly
                580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
    610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
            645                 650                 655

Thr Ile Leu Leu Glu Ala Phe Pro Glu Phe Thr Ile Pro Ala Leu Gly
                660                 665                 670

Ala Phe Val Ile Tyr Ser Lys Val Gln Glu Arg Asn Glu Ile Ile Lys
        675                 680                 685

Thr Ile Asp Asn Cys Leu Glu Gln Arg Ile Lys Arg Trp Lys Asp Ser
    690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
            725                 730                 735

Ala Ile Lys Ala Lys Ile Asp Leu Glu Tyr Lys Lys Tyr Ser Gly Ser
        740                 745                 750

Asp Lys Glu Asn Ile Lys Ser Gln Val Glu Asn Leu Lys Asn Ser Leu
    755                 760                 765

Asp Val Lys Ile Ser Glu Ala Met Asn Asn Ile Asn Lys Phe Ile Arg
    770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
            805                 810                 815

Leu Ile Asp Ser His Asn Ile Ile Leu Val Gly Glu Val Asp Lys Leu
                820                 825                 830

Lys Ala Lys Val Asn Asn Ser Phe Gln Asn Thr Ile Pro Phe Asn Ile
        835                 840                 845

Phe Ser Tyr Thr Asn Asn Ser Leu Leu Lys Asp Ile Ile Asn Glu Tyr
    850                 855                 860

Phe Asn Asn Ile Asn Asp Ser Lys Ile Leu Ser Leu Gln Asn Arg Lys
865                 870                 875                 880

Asn Thr Leu Val Asp Thr Ser Gly Tyr Asn Ala Glu Val Ser Glu Glu
            885                 890                 895

Gly Asp Val Gln Leu Asn Pro Ile Phe Pro Phe Asp Phe Lys Leu Gly
                900                 905                 910

Ser Ser Gly Glu Asp Arg Gly Lys Val Ile Val Thr Gln Asn Glu Asn
        915                 920                 925

Ile Val Tyr Asn Ser Met Tyr Glu Ser Phe Ser Ile Ser Phe Trp Ile
    930                 935                 940

Arg Ile Asn Lys Trp Val Ser Asn Leu Pro Gly Tyr Thr Ile Ile Asp
945                 950                 955                 960

Ser Val Lys Asn Asn Ser Gly Trp Ser Ile Gly Ile Ile Ser Asn Phe
```

-continued

```
                  965                 970                 975
Leu Val Phe Thr Leu Lys Gln Asn Glu Asp Ser Glu Gln Ser Ile Asn
                    980                 985                 990
Phe Ser Tyr Asp Ile Ser Asn Asn Ala Pro Gly Tyr Asn Lys Trp Phe
            995                1000                1005
Phe Val Thr Val Thr Asn Asn Met Met Gly Asn Met Lys Ile Tyr
       1010                1015                1020
Ile Asn Gly Lys Leu Ile Asp Thr Ile Lys Val Lys Glu Leu Thr
       1025                1030                1035
Gly Ile Asn Phe Ser Lys Thr Ile Thr Phe Glu Ile Asn Lys Ile
       1040                1045                1050
Pro Asp Thr Gly Leu Ile Thr Ser Asp Ser Asp Asn Ile Asn Met
       1055                1060                1065
Trp Ile Arg Asp Phe Tyr Ile Phe Ala Lys Glu Leu Asp Gly Lys
       1070                1075                1080
Asp Ile Asn Ile Leu Phe Asn Ser Leu Gln Tyr Thr Asn Val Val
       1085                1090                1095
Lys Asp Tyr Trp Gly Asn Asp Leu Arg Tyr Asn Lys Glu Tyr Tyr
       1100                1105                1110
Met Val Asn Ile Asp Tyr Leu Asn Arg Tyr Met Tyr Ala Asn Ser
       1115                1120                1125
Arg Gln Ile Val Phe Asn Thr Arg Arg Asn Asn Asn Asp Phe Asn
       1130                1135                1140
Glu Gly Tyr Lys Ile Ile Ile Lys Arg Ile Arg Gly Asn Thr Asn
       1145                1150                1155
Asp Thr Arg Val Arg Gly Gly Asp Ile Leu Tyr Phe Asp Met Thr
       1160                1165                1170
Ile Asn Asn Lys Ala Tyr Asn Leu Phe Met Lys Asn Glu Thr Met
       1175                1180                1185
Tyr Ala Asp Asn His Ser Thr Glu Asp Ile Tyr Ala Ile Gly Leu
       1190                1195                1200
Arg Glu Gln Thr Lys Asp Ile Asn Asp Asn Ile Ile Phe Gln Ile
       1205                1210                1215
Gln Pro Met Asn Asn Thr Tyr Tyr Tyr Ala Ser Gln Ile Phe Lys
       1220                1225                1230
Ser Asn Phe Asn Gly Glu Asn Ile Ser Gly Ile Cys Ser Ile Gly
       1235                1240                1245
Thr Tyr Arg Phe Arg Leu Gly Gly Asp Trp Tyr Arg His Asn Tyr
       1250                1255                1260
Leu Val Pro Thr Val Lys Gln Gly Asn Tyr Ala Ser Leu Leu Glu
       1265                1270                1275
Ser Thr Ser Thr His Trp Gly Phe Val Pro Val Ser Glu
       1280                1285                1290
```

<210> SEQ ID NO 15
<211> LENGTH: 1280
<212> TYPE: PRT
<213> ORGANISM: Clostridium botulinum
<300> PUBLICATION INFORMATION:
<308> DATABASE ACCESSION NUMBER: BAA08418

<400> SEQUENCE: 15

```
Met Pro Ile Thr Ile Asn Asn Phe Asn Tyr Ser Asp Pro Val Asp Asn
1               5                  10                  15

Lys Asn Ile Leu Tyr Leu Asp Thr His Leu Asn Thr Leu Ala Asn Glu
```

-continued

```
            20                  25                  30
Pro Glu Lys Ala Phe Arg Ile Ile Gly Asn Ile Trp Val Ile Pro Asp
            35                  40                  45
Arg Phe Ser Arg Asp Ser Asn Pro Asn Leu Asn Lys Pro Pro Arg Val
 50                  55                  60
Thr Ser Pro Lys Ser Gly Tyr Tyr Asp Pro Asn Tyr Leu Ser Thr Asp
 65                  70                  75                  80
Ser Glu Lys Asp Thr Phe Leu Lys Glu Ile Lys Leu Phe Lys Arg
                 85                  90                  95
Ile Asn Ser Arg Glu Ile Gly Glu Leu Ile Tyr Arg Leu Ala Thr
                100                 105                 110
Asp Ile Pro Phe Pro Gly Asn Asn Thr Pro Ile Asn Thr Phe Asp
                115                 120                 125
Phe Asp Val Asp Phe Asn Ser Val Asp Val Lys Thr Arg Gln Gly Asn
                130                 135                 140
Asn Trp Val Lys Thr Gly Ser Ile Asn Pro Ser Val Ile Thr Gly
145                 150                 155                 160
Pro Arg Glu Asn Ile Ile Asp Pro Glu Thr Ser Thr Phe Lys Leu Thr
                165                 170                 175
Asn Asn Thr Phe Ala Ala Gln Glu Gly Phe Gly Ala Leu Ser Ile Ile
                180                 185                 190
Ser Ile Ser Pro Arg Phe Met Leu Thr Tyr Ser Asn Ala Thr Asn Asn
                195                 200                 205
Val Gly Glu Gly Arg Phe Ser Lys Ser Glu Phe Cys Met Asp Pro Ile
                210                 215                 220
Leu Ile Leu Met His Glu Leu Asn His Thr Met His Asn Leu Tyr Gly
225                 230                 235                 240
Ile Ala Ile Pro Asn Asp Gln Arg Ile Ser Ser Val Thr Ser Asn Ile
                245                 250                 255
Phe Tyr Ser Gln Tyr Lys Val Lys Leu Glu Tyr Ala Glu Ile Tyr Ala
                260                 265                 270
Phe Gly Gly Pro Thr Ile Asp Leu Ile Pro Lys Ser Gly Arg Lys Tyr
                275                 280                 285
Phe Glu Glu Lys Ala Leu Asp Tyr Tyr Arg Ser Ile Ala Lys Arg Leu
                290                 295                 300
Asn Ser Ile Thr Thr Ala Asn Pro Ser Ser Phe Asn Lys Tyr Ile Gly
305                 310                 315                 320
Glu Tyr Lys Gln Lys Leu Ile Arg Lys Tyr Arg Phe Val Val Glu Ser
                325                 330                 335
Ser Gly Glu Val Ala Val Asp Arg Asn Lys Phe Ala Glu Leu Tyr Lys
                340                 345                 350
Glu Leu Thr Gln Ile Phe Thr Glu Phe Asn Tyr Ala Lys Ile Tyr Asn
                355                 360                 365
Val Gln Asn Arg Lys Ile Tyr Leu Ser Asn Val Tyr Thr Pro Val Thr
                370                 375                 380
Ala Asn Ile Leu Asp Asp Asn Val Tyr Asp Ile Gln Asn Gly Phe Asn
385                 390                 395                 400
Ile Pro Lys Ser Asn Leu Asn Val Leu Phe Met Gly Gln Asn Leu Ser
                405                 410                 415
Arg Asn Pro Ala Leu Arg Lys Val Asn Pro Glu Asn Met Leu Tyr Leu
                420                 425                 430
Phe Thr Lys Phe Cys His Lys Ala Ile Asp Gly Arg Ser Leu Tyr Asn
                435                 440                 445
```

```
Lys Thr Leu Asp Cys Arg Glu Leu Leu Val Lys Asn Thr Asp Leu Pro
    450                 455                 460
Phe Ile Gly Asp Ile Ser Asp Ile Lys Thr Asp Ile Phe Leu Ser Lys
465                 470                 475                 480
Asp Ile Asn Val Glu Thr Glu Val Ile Asp Tyr Pro Asp Asn Val Ser
                485                 490                 495
Val Asp Gln Val Ile Leu Ser Lys Asn Thr Ser Glu His Gly Gln Leu
            500                 505                 510
Asp Leu Leu Tyr Pro Ile Ile Glu Gly Ser Gln Val Leu Pro Gly
        515                 520                 525
Glu Asn Gln Val Phe Tyr Asp Asn Arg Thr Gln Asn Val Asp Tyr Leu
    530                 535                 540
Asn Ser Tyr Tyr Leu Glu Ser Gln Lys Leu Ser Asp Asn Val Glu
545                 550                 555                 560
Asp Phe Thr Phe Thr Thr Ser Ile Glu Glu Ala Leu Asp Asn Ser Gly
                565                 570                 575
Lys Val Tyr Thr Tyr Phe Pro Lys Leu Ala Asp Lys Val Asn Thr Gly
            580                 585                 590
Val Gln Gly Gly Leu Phe Leu Met Trp Ala Asn Asp Val Val Glu Asp
        595                 600                 605
Phe Thr Thr Asn Ile Leu Arg Lys Asp Thr Leu Asp Lys Ile Ser Asp
    610                 615                 620
Val Ser Ala Ile Ile Pro Tyr Ile Gly Pro Ala Leu Asn Ile Ser Asn
625                 630                 635                 640
Ser Val Arg Arg Glu Asn Phe Thr Glu Ala Phe Ala Val Thr Gly Val
                645                 650                 655
Thr Ile Leu Leu Glu Ala Phe Gln Glu Phe Thr Ile Pro Ala Leu Gly
            660                 665                 670
Ala Phe Val Ile Tyr Ser Lys Val Gln Glu Arg Asn Glu Ile Ile Lys
        675                 680                 685
Thr Ile Asp Asn Cys Leu Glu Gln Arg Ile Lys Arg Trp Lys Asp Ser
    690                 695                 700
Tyr Glu Trp Met Ile Gly Thr Trp Leu Ser Arg Ile Thr Thr Gln Phe
705                 710                 715                 720
Asn Asn Ile Ser Tyr Gln Met Tyr Asp Ser Leu Asn Tyr Gln Ala Asp
                725                 730                 735
Ala Ile Lys Asp Lys Ile Asp Leu Glu Tyr Lys Lys Tyr Ser Gly Ser
            740                 745                 750
Asp Lys Glu Asn Ile Lys Ser Gln Val Glu Asn Leu Lys Asn Ser Leu
        755                 760                 765
Asp Ile Lys Ile Ser Glu Ala Met Asn Asn Ile Asn Lys Phe Ile Arg
    770                 775                 780
Glu Cys Ser Val Thr Tyr Leu Phe Lys Asn Met Leu Pro Lys Val Ile
785                 790                 795                 800
Asp Glu Leu Asn Lys Phe Asp Leu Lys Thr Lys Thr Glu Leu Ile Asn
                805                 810                 815
Leu Ile Asp Ser His Asn Ile Ile Leu Val Gly Glu Val Asp Arg Leu
            820                 825                 830
Lys Ala Lys Val Asn Glu Ser Phe Glu Asn Thr Ile Pro Phe Asn Ile
        835                 840                 845
Phe Ser Tyr Thr Asn Asn Ser Leu Leu Lys Asp Ile Ile Asn Glu Tyr
    850                 855                 860
```

```
Phe Asn Ser Ile Asn Asp Ser Lys Ile Leu Ser Leu Gln Asn Lys Lys
865                 870                 875                 880

Asn Ala Leu Val Asp Thr Ser Gly Tyr Asn Ala Glu Val Arg Leu Glu
            885                 890                 895

Gly Asp Val Gln Val Asn Thr Ile Tyr Thr Asn Asp Phe Lys Leu Ser
        900                 905                 910

Ser Ser Gly Asp Lys Ile Ile Val Asn Leu Asn Asn Asn Ile Leu Tyr
            915                 920                 925

Ser Ala Ile Tyr Glu Asn Ser Ser Val Ser Phe Trp Ile Lys Ile Ser
    930                 935                 940

Lys Asp Leu Thr Asn Ser His Asn Glu Tyr Thr Ile Ile Asn Ser Ile
945                 950                 955                 960

Lys Gln Asn Ser Gly Trp Lys Leu Cys Ile Arg Asn Gly Asn Ile Glu
            965                 970                 975

Trp Ile Leu Gln Asp Ile Asn Arg Lys Tyr Lys Ser Leu Ile Phe Asp
        980                 985                 990

Tyr Ser Glu Ser Leu Ser His Thr Gly Tyr Thr Asn Lys Trp Phe Phe
        995                 1000                1005

Val Thr Ile Thr Asn Asn Ile Met Gly Tyr Met Lys Leu Tyr Ile
    1010                1015                1020

Asn Gly Glu Leu Lys Gln Ser Glu Arg Ile Glu Asp Leu Asn Glu
    1025                1030                1035

Val Lys Leu Asp Lys Thr Ile Val Phe Gly Ile Asp Glu Asn Ile
    1040                1045                1050

Asp Glu Asn Gln Met Leu Trp Ile Arg Asp Phe Asn Ile Phe Ser
    1055                1060                1065

Lys Glu Leu Ser Asn Glu Asp Ile Asn Ile Val Tyr Glu Gly Gln
    1070                1075                1080

Ile Leu Arg Asn Val Ile Lys Asp Tyr Trp Gly Asn Pro Leu Lys
    1085                1090                1095

Phe Asp Thr Glu Tyr Tyr Ile Ile Asn Asp Asn Tyr Ile Asp Arg
    1100                1105                1110

Tyr Ile Ala Pro Lys Ser Asn Ile Leu Val Leu Val Gln Tyr Pro
    1115                1120                1125

Asp Arg Ser Lys Leu Tyr Thr Gly Asn Pro Ile Thr Ile Lys Ser
    1130                1135                1140

Val Ser Asp Lys Asn Pro Tyr Ser Arg Ile Leu Asn Gly Asp Asn
    1145                1150                1155

Ile Met Phe His Met Leu Tyr Asn Ser Gly Lys Tyr Met Ile Ile
    1160                1165                1170

Arg Asp Thr Asp Thr Ile Tyr Ala Ile Glu Gly Arg Glu Cys Ser
    1175                1180                1185

Lys Asn Cys Val Tyr Ala Leu Lys Leu Gln Ser Asn Leu Gly Asn
    1190                1195                1200

Tyr Gly Ile Gly Ile Phe Ser Ile Lys Asn Ile Val Ser Gln Asn
    1205                1210                1215

Lys Tyr Cys Ser Gln Ile Phe Ser Ser Phe Met Lys Asn Thr Met
    1220                1225                1230

Leu Leu Ala Asp Ile Tyr Lys Pro Trp Arg Phe Ser Phe Glu Asn
    1235                1240                1245

Ala Tyr Thr Pro Val Ala Val Thr Asn Tyr Glu Thr Lys Leu Leu
    1250                1255                1260

Ser Thr Ser Ser Phe Trp Lys Phe Ile Ser Arg Asp Pro Gly Trp
```

Val Glu
    1280

<210> SEQ ID NO 16
<211> LENGTH: 1280
<212> TYPE: PRT
<213> ORGANISM: Clostridium botulinum
<300> PUBLICATION INFORMATION:
<308> DATABASE ACCESSION NUMBER: BAA89713

<400> SEQUENCE: 16

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Gly Asn Ile Trp Val Ile Pro Asp
        35                  40                  45

Arg Phe Ser Arg Asp Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Glu Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ala Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asn
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Arg Ile Ser Ser Val Thr Ser Asn Ile
                245                 250                 255

Phe Tyr Ser Gln Tyr Lys Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Ala Val Asp Arg Asn Lys Phe Ala Glu Leu Tyr Lys

```
                340                 345                 350
Glu Leu Thr Gln Ile Phe Thr Glu Phe Asn Tyr Ala Lys Ile Tyr Asn
            355                 360                 365
Val Gln Asn Arg Lys Ile Tyr Leu Ser Asn Val Tyr Thr Pro Val Thr
        370                 375                 380
Ala Asn Ile Leu Asp Asp Asn Val Tyr Asp Ile Gln Asn Gly Phe Asn
385                 390                 395                 400
Ile Pro Lys Ser Asn Leu Asn Val Leu Phe Met Gly Gln Asn Leu Ser
                405                 410                 415
Arg Asn Pro Ala Leu Arg Lys Val Asn Pro Glu Asn Met Leu Tyr Leu
            420                 425                 430
Phe Thr Lys Phe Cys His Lys Ala Ile Asp Gly Arg Ser Leu Tyr Asn
        435                 440                 445
Lys Thr Leu Asp Cys Arg Glu Leu Leu Val Lys Asn Thr Asp Leu Pro
450                 455                 460
Phe Ile Gly Asp Ile Ser Asp Ile Lys Thr Asp Ile Phe Leu Ser Lys
465                 470                 475                 480
Asp Ile Asn Glu Glu Thr Glu Val Ile Asp Tyr Pro Asp Asn Val Ser
                485                 490                 495
Val Asp Gln Val Ile Leu Ser Lys Asn Thr Ser Glu His Gly Gln Leu
            500                 505                 510
Asp Leu Leu Tyr Pro Ile Ile Glu Gly Glu Ser Gln Val Leu Pro Gly
        515                 520                 525
Glu Asn Gln Val Phe Tyr Asp Asn Arg Thr Gln Asn Val Asp Tyr Leu
530                 535                 540
Asn Ser Tyr Tyr Tyr Leu Glu Ser Gln Lys Leu Ser Asp Asn Val Glu
545                 550                 555                 560
Asp Phe Thr Phe Thr Thr Ser Ile Glu Glu Ala Leu Asp Asn Ser Gly
                565                 570                 575
Lys Val Tyr Thr Tyr Phe Pro Lys Leu Ala Asp Lys Val Asn Thr Gly
            580                 585                 590
Val Gln Gly Gly Leu Phe Leu Met Trp Ala Asn Asp Val Val Glu Asp
        595                 600                 605
Phe Thr Thr Asn Ile Leu Arg Lys Asp Thr Leu Asp Lys Ile Ser Asp
610                 615                 620
Val Ser Ala Ile Ile Pro Tyr Ile Gly Pro Ala Leu Asn Ile Ser Asn
625                 630                 635                 640
Ser Val Arg Arg Gly Asn Phe Thr Glu Ala Phe Ala Val Thr Gly Val
                645                 650                 655
Thr Ile Leu Leu Glu Ala Phe Gln Glu Phe Thr Ile Pro Ala Leu Gly
            660                 665                 670
Ala Phe Val Ile Tyr Ser Lys Val Gln Glu Arg Asn Glu Ile Ile Lys
        675                 680                 685
Thr Ile Asp Asn Cys Leu Glu Gln Arg Ile Lys Arg Trp Lys Asp Ser
690                 695                 700
Tyr Glu Trp Met Ile Gly Thr Trp Leu Ser Arg Ile Thr Thr Gln Phe
705                 710                 715                 720
Asn Asn Ile Ser Tyr Gln Met Tyr Asp Ser Leu Asn Tyr Gln Ala Asp
                725                 730                 735
Ala Ile Lys Asp Lys Ile Asp Leu Glu Tyr Lys Lys Tyr Ser Gly Ser
            740                 745                 750
Asp Lys Glu Asn Ile Lys Ser Gln Val Glu Asn Leu Lys Asn Ser Leu
        755                 760                 765
```

-continued

```
Asp Ile Lys Ile Ser Glu Ala Met Asn Asn Ile Asn Lys Phe Ile Arg
        770                 775                 780

Glu Cys Ser Val Thr Tyr Leu Phe Lys Asn Met Leu Pro Lys Val Ile
785                 790                 795                 800

Asp Glu Leu Asn Lys Phe Asp Leu Lys Thr Lys Thr Glu Leu Ile Asn
                805                 810                 815

Leu Ile Asp Ser His Asn Ile Ile Leu Val Gly Glu Val Asp Arg Leu
                820                 825                 830

Lys Ala Lys Val Asn Glu Ser Phe Glu Asn Thr Ile Pro Phe Asn Ile
                835                 840                 845

Phe Ser Tyr Thr Asn Asn Ser Leu Leu Lys Asp Ile Ile Asn Glu Tyr
850                 855                 860

Phe Asn Ser Ile Asn Asp Ser Lys Ile Leu Ser Leu Gln Asn Lys Lys
865                 870                 875                 880

Asn Ala Leu Val Asp Thr Ser Gly Tyr Asn Ala Glu Val Arg Leu Glu
                885                 890                 895

Gly Asp Val Gln Val Asn Thr Ile Tyr Thr Asn Asp Phe Lys Leu Ser
                900                 905                 910

Ser Ser Gly Asp Lys Ile Ile Val Asn Leu Asn Asn Asn Ile Leu Tyr
                915                 920                 925

Ser Ala Ile Tyr Glu Asn Ser Ser Val Ser Phe Trp Ile Lys Ile Ser
930                 935                 940

Lys Asp Leu Thr Asn Ser His Asn Glu Tyr Thr Ile Ile Asn Ser Ile
945                 950                 955                 960

Lys Gln Asn Ser Gly Trp Lys Leu Cys Ile Arg Asn Gly Asn Ile Glu
                965                 970                 975

Trp Ile Leu Gln Asp Ile Asn Arg Lys Tyr Lys Ser Leu Ile Phe Asp
                980                 985                 990

Tyr Ser Glu Ser Leu Ser His Thr Gly Tyr Thr Asn Lys Trp Phe Phe
            995                 1000                1005

Val Thr Ile Thr Asn Asn Ile Met Gly Tyr Met Lys Leu Tyr Ile
    1010                1015                1020

Asn Gly Glu Leu Lys Gln Ser Glu Arg Ile Glu Asp Leu Asn Glu
    1025                1030                1035

Val Lys Leu Asp Lys Thr Ile Val Phe Gly Ile Asp Glu Asn Ile
    1040                1045                1050

Asp Glu Asn Gln Met Leu Trp Ile Arg Asp Phe Asn Ile Phe Ser
    1055                1060                1065

Lys Glu Leu Ser Asn Glu Asp Ile Asn Ile Val Tyr Glu Gly Gln
    1070                1075                1080

Ile Leu Arg Asn Val Ile Lys Asp Tyr Trp Gly Asn Pro Leu Lys
    1085                1090                1095

Phe Asp Thr Glu Tyr Tyr Ile Ile Asn Asp Asn Tyr Ile Asp Arg
    1100                1105                1110

Tyr Ile Ala Pro Lys Ser Asn Ile Leu Val Leu Val Gln Tyr Pro
    1115                1120                1125

Asp Arg Ser Lys Leu Tyr Thr Gly Asn Pro Ile Thr Ile Lys Ser
    1130                1135                1140

Val Ser Asp Lys Asn Pro Tyr Ser Arg Ile Leu Asn Gly Asp Asn
    1145                1150                1155

Ile Met Phe His Met Leu Tyr Asn Ser Gly Lys Tyr Met Ile Ile
    1160                1165                1170
```

```
Arg Asp Thr Asp Thr Ile Tyr Ala Ile Glu Gly Arg Glu Cys Ser
    1175                1180                1185

Lys Asn Cys Val Tyr Ala Leu Lys Leu Gln Ser Asn Leu Gly Asn
    1190                1195                1200

Tyr Gly Ile Gly Ile Phe Ser Ile Lys Asn Ile Val Ser Gln Asn
    1205                1210                1215

Lys Tyr Cys Ser Gln Ile Phe Ser Ser Phe Met Lys Asn Thr Met
    1220                1225                1230

Leu Leu Ala Asp Ile Tyr Lys Pro Trp Arg Phe Ser Phe Glu Asn
    1235                1240                1245

Ala Tyr Thr Pro Val Ala Val Thr Asn Tyr Glu Thr Lys Leu Leu
    1250                1255                1260

Ser Thr Ser Ser Phe Trp Lys Phe Ile Ser Arg Asp Pro Gly Trp
    1265                1270                1275

Val Glu
    1280

<210> SEQ ID NO 17
<211> LENGTH: 1276
<212> TYPE: PRT
<213> ORGANISM: Clostridium botulinum
<300> PUBLICATION INFORMATION:
<308> DATABASE ACCESSION NUMBER: CAA38175
<300> PUBLICATION INFORMATION:
<308> DATABASE ACCESSION NUMBER: P19321
<300> PUBLICATION INFORMATION:
<308> DATABASE ACCESSION NUMBER: S11455

<400> SEQUENCE: 17

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
                20                  25                  30

Pro Val Lys Ala Phe Met Ile Thr Gln Asn Ile Trp Val Ile Pro Glu
            35                  40                  45

Arg Phe Ser Ser Asp Thr Asn Pro Ser Leu Ser Lys Pro Pro Arg Pro
        50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220
```

```
Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
            245                 250                 255

Phe Phe Ser Gln Asp Gly Pro Asn Val Gln Phe Glu Glu Leu Tyr Thr
        260                 265                 270

Phe Gly Gly Leu Asp Val Glu Ile Ile Pro Gln Ile Glu Arg Ser Gln
    275                 280                 285

Leu Arg Glu Lys Ala Leu Gly His Tyr Lys Asp Ile Ala Lys Arg Leu
290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
            325                 330                 335

Thr Gly Asn Phe Val Val Asn Ile Asp Lys Phe Asn Ser Leu Tyr Ser
        340                 345                 350

Asp Leu Thr Asn Val Met Ser Glu Val Val Tyr Ser Ser Gln Tyr Asn
    355                 360                 365

Val Lys Asn Arg Thr His Tyr Phe Ser Arg His Tyr Leu Pro Val Phe
370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
            405                 410                 415

Arg Asn Pro Ala Leu Gln Lys Leu Ser Ser Glu Ser Val Val Asp Leu
        420                 425                 430

Phe Thr Lys Val Cys Leu Arg Leu Thr Lys Asn Ser Arg Asp Asp Ser
    435                 440                 445

Thr Cys Ile Lys Val Lys Asn Asn Arg Leu Pro Tyr Val Ala Asp Lys
450                 455                 460

Asp Ser Ile Ser Gln Glu Ile Phe Glu Asn Lys Ile Ile Thr Asp Glu
465                 470                 475                 480

Thr Asn Val Gln Asn Tyr Ser Asp Lys Phe Ser Leu Asp Glu Ser Ile
            485                 490                 495

Leu Asp Gly Gln Val Pro Ile Asn Pro Glu Ile Val Asp Pro Leu Leu
        500                 505                 510

Pro Asn Val Asn Met Glu Pro Leu Asn Leu Pro Gly Glu Glu Ile Val
    515                 520                 525

Phe Tyr Asp Asp Ile Thr Lys Tyr Val Asp Tyr Leu Asn Ser Tyr Tyr
530                 535                 540

Tyr Leu Glu Ser Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
            565                 570                 575

Phe Leu Pro Ser Leu Ala Glu Lys Val Asn Lys Gly Val Gln Ala Gly
        580                 585                 590

Leu Phe Leu Asn Trp Ala Asn Glu Val Val Glu Asp Phe Thr Thr Asn
    595                 600                 605

Ile Met Lys Lys Asp Thr Leu Asp Lys Ile Ser Asp Val Ser Val Ile
610                 615                 620

Ile Pro Tyr Ile Gly Pro Ala Leu Asn Ile Gly Asn Ser Ala Leu Arg
625                 630                 635                 640
```

-continued

Gly Asn Phe Asn Gln Ala Phe Ala Thr Ala Gly Val Ala Phe Leu Leu
             645                 650                 655

Glu Gly Phe Pro Glu Phe Thr Ile Pro Ala Leu Gly Val Phe Thr Phe
         660                 665                 670

Tyr Ser Ser Ile Gln Glu Arg Glu Lys Ile Ile Lys Thr Ile Glu Asn
             675                 680                 685

Cys Leu Glu Gln Arg Val Lys Arg Trp Lys Asp Ser Tyr Gln Trp Met
    690                 695                 700

Val Ser Asn Trp Leu Ser Arg Ile Thr Thr Gln Phe Asn His Ile Asn
705                 710                 715                 720

Tyr Gln Met Tyr Asp Ser Leu Ser Tyr Gln Ala Asp Ala Ile Lys Ala
                725                 730                 735

Lys Ile Asp Leu Glu Tyr Lys Lys Tyr Ser Gly Ser Asp Lys Glu Asn
            740                 745                 750

Ile Lys Ser Gln Val Glu Asn Leu Lys Asn Ser Leu Asp Val Lys Ile
        755                 760                 765

Ser Glu Ala Met Asn Asn Ile Asn Lys Phe Ile Arg Glu Cys Ser Val
770                 775                 780

Thr Tyr Leu Phe Lys Asn Met Leu Pro Lys Val Ile Asp Glu Leu Asn
785                 790                 795                 800

Lys Phe Asp Leu Arg Thr Lys Thr Glu Leu Ile Asn Leu Ile Asp Ser
                805                 810                 815

His Asn Ile Ile Leu Val Gly Glu Val Asp Arg Leu Lys Ala Lys Val
            820                 825                 830

Asn Glu Ser Phe Glu Asn Thr Met Pro Phe Asn Ile Phe Ser Tyr Thr
    835                 840                 845

Asn Asn Ser Leu Leu Lys Asp Ile Ile Asn Glu Tyr Phe Asn Ser Ile
850                 855                 860

Asn Asp Ser Lys Ile Leu Ser Leu Gln Asn Lys Lys Asn Ala Leu Val
865                 870                 875                 880

Asp Thr Ser Gly Tyr Asn Ala Glu Val Arg Val Gly Asp Asn Val Gln
                885                 890                 895

Leu Asn Thr Ile Tyr Thr Asn Asp Phe Lys Leu Ser Ser Ser Gly Asp
            900                 905                 910

Lys Ile Ile Val Asn Leu Asn Asn Asn Ile Leu Tyr Ser Ala Ile Tyr
    915                 920                 925

Glu Asn Ser Ser Val Ser Phe Trp Ile Lys Ile Ser Lys Asp Leu Thr
    930                 935                 940

Asn Ser His Asn Glu Tyr Thr Ile Ile Asn Ser Ile Glu Gln Asn Ser
945                 950                 955                 960

Gly Trp Lys Leu Cys Ile Arg Asn Gly Asn Ile Glu Trp Ile Leu Gln
                965                 970                 975

Asp Val Asn Arg Lys Tyr Lys Ser Leu Ile Phe Asp Tyr Ser Glu Ser
            980                 985                 990

Leu Ser His Thr Gly Tyr Thr Asn Lys Trp Phe Phe Val Thr Ile Thr
        995                 1000                1005

Asn Asn Ile Met Gly Tyr Met Lys Leu Tyr Ile Asn Gly Glu Leu
    1010                1015                1020

Lys Gln Ser Gln Lys Ile Glu Asp Leu Asp Glu Val Lys Leu Asp
    1025                1030                1035

Lys Thr Ile Val Phe Gly Ile Asp Glu Asn Ile Asp Glu Asn Gln
    1040                1045                1050

Met Leu Trp Ile Arg Asp Phe Asn Ile Phe Ser Lys Glu Leu Ser

|      |      |      |
|------|------|------|
| 1055 | 1060 | 1065 |

Asn Glu Asp Ile Asn Ile Val Tyr Glu Gly Gln Ile Leu Arg Asn
    1070                1075                1080

Val Ile Lys Asp Tyr Trp Gly Asn Pro Leu Lys Phe Asp Thr Glu
    1085                1090                1095

Tyr Tyr Ile Ile Asn Asp Asn Tyr Ile Asp Arg Tyr Ile Ala Pro
    1100                1105                1110

Glu Ser Asn Val Leu Val Leu Val Gln Tyr Pro Asp Arg Ser Lys
    1115                1120                1125

Leu Tyr Thr Gly Asn Pro Ile Thr Ile Lys Ser Val Ser Asp Lys
    1130                1135                1140

Asn Pro Tyr Ser Arg Ile Leu Asn Gly Asp Asn Ile Ile Leu His
    1145                1150                1155

Met Leu Tyr Asn Ser Arg Lys Tyr Met Ile Ile Arg Asp Thr Asp
    1160                1165                1170

Thr Ile Tyr Ala Thr Gln Gly Gly Glu Cys Ser Gln Asn Cys Val
    1175                1180                1185

Tyr Ala Leu Lys Leu Gln Ser Asn Leu Gly Asn Tyr Gly Ile Gly
    1190                1195                1200

Ile Phe Ser Ile Lys Asn Ile Val Ser Lys Asn Lys Tyr Cys Ser
    1205                1210                1215

Gln Ile Phe Ser Ser Phe Arg Glu Asn Thr Met Leu Leu Ala Asp
    1220                1225                1230

Ile Tyr Lys Pro Trp Arg Phe Ser Phe Lys Asn Ala Tyr Thr Pro
    1235                1240                1245

Val Ala Val Thr Asn Tyr Glu Thr Lys Leu Leu Ser Thr Ser Ser
    1250                1255                1260

Phe Trp Lys Phe Ile Ser Arg Asp Pro Gly Trp Val Glu
    1265                1270                1275

<210> SEQ ID NO 18
<211> LENGTH: 1276
<212> TYPE: PRT
<213> ORGANISM: Clostridium phage
<300> PUBLICATION INFORMATION:
<308> DATABASE ACCESSION NUMBER: AAB24244

<400> SEQUENCE: 18

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly

-continued

```
            130                 135                 140
Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Pro Gln Ile Glu Arg Ser Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
        355                 360                 365

Val Lys Asn Arg Thr His Tyr Phe Ser Arg His Tyr Leu Pro Val Phe
    370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Leu Arg Leu Thr Lys Asn Ser Arg Asp Asp Ser
        435                 440                 445

Thr Cys Ile Lys Val Lys Asn Asn Arg Leu Pro Tyr Val Ala Asp Lys
    450                 455                 460

Asp Ser Ile Ser Gln Glu Ile Phe Glu Asn Lys Ile Ile Thr Asp Glu
465                 470                 475                 480

Thr Asn Val Gln Asn Tyr Ser Asp Asn Phe Ser Leu Asp Glu Ser Ile
                485                 490                 495

Leu Asp Gly Gln Val Pro Ile Asn Pro Glu Ile Val Asp Pro Leu Leu
            500                 505                 510

Pro Asn Val Asn Met Glu Pro Leu Asn Leu Pro Gly Glu Glu Ile Val
        515                 520                 525

Phe Tyr Asp Asp Ile Thr Lys Tyr Val Asp Tyr Leu Asn Ser Tyr Tyr
    530                 535                 540

Tyr Leu Glu Ser Gln Lys Leu Ser Asn Asn Val Glu Asn Ile Thr Leu
545                 550                 555                 560
```

```
Thr Thr Ser Val Glu Glu Ala Leu Gly Tyr Ser Asn Lys Ile Tyr Thr
                565                 570                 575

Phe Leu Pro Ser Leu Ala Glu Lys Val Asn Lys Gly Val Gln Ala Gly
            580                 585                 590

Leu Phe Leu Asn Trp Ala Asn Glu Val Val Glu Asp Phe Thr Thr Asn
        595                 600                 605

Ile Met Lys Lys Asp Thr Leu Asp Lys Ile Ser Asp Val Ser Val Ile
    610                 615                 620

Ile Pro Tyr Ile Gly Pro Ala Leu Asn Ile Gly Asn Ser Ala Leu Arg
625                 630                 635                 640

Gly Asn Phe Lys Gln Ala Phe Ala Thr Ala Gly Val Ala Phe Leu Leu
                645                 650                 655

Glu Gly Phe Pro Glu Phe Thr Ile Pro Ala Leu Gly Val Phe Thr Phe
            660                 665                 670

Tyr Ser Ser Ile Gln Glu Arg Glu Lys Ile Ile Lys Thr Ile Glu Asn
        675                 680                 685

Cys Leu Glu Gln Arg Val Lys Arg Trp Lys Asp Ser Tyr Gln Trp Met
    690                 695                 700

Val Ser Asn Trp Leu Ser Arg Ile Thr Thr Gln Phe Asn His Ile Asn
705                 710                 715                 720

Tyr Gln Met Tyr Asp Ser Leu Ser Tyr Gln Ala Asp Ala Ile Lys Ala
                725                 730                 735

Lys Ile Asp Leu Glu Tyr Lys Lys Tyr Ser Gly Ser Asp Lys Glu Asn
            740                 745                 750

Ile Lys Ser Gln Val Glu Asn Leu Lys Asn Ser Leu Asp Val Lys Ile
        755                 760                 765

Ser Glu Ala Met Asn Asn Ile Asn Lys Phe Ile Arg Glu Cys Ser Val
    770                 775                 780

Thr Tyr Leu Phe Lys Asn Met Leu Pro Lys Val Ile Asp Glu Leu Asn
785                 790                 795                 800

Lys Phe Asp Leu Arg Thr Lys Thr Glu Leu Ile Asn Leu Ile Asp Ser
                805                 810                 815

His Asn Ile Ile Leu Val Gly Glu Val Asp Arg Leu Lys Ala Lys Val
            820                 825                 830

Asn Glu Ser Phe Glu Asn Thr Met Pro Phe Asn Ile Phe Ser Tyr Thr
        835                 840                 845

Asn Asn Ser Leu Leu Lys Asp Ile Ile Asn Glu Tyr Phe Asn Ser Ile
    850                 855                 860

Asn Asp Ser Lys Ile Leu Ser Leu Gln Asn Lys Lys Asn Ala Leu Val
865                 870                 875                 880

Asp Thr Ser Gly Tyr Asn Ala Glu Val Arg Val Gly Asp Asn Val Gln
                885                 890                 895

Leu Asn Thr Ile Tyr Thr Asn Asp Phe Lys Leu Ser Ser Ser Gly Asp
            900                 905                 910

Lys Ile Ile Val Asn Leu Asn Asn Ile Leu Tyr Ser Ala Ile Tyr
        915                 920                 925

Glu Asn Ser Ser Val Ser Phe Trp Ile Lys Ile Ser Lys Asp Leu Thr
    930                 935                 940

Asn Ser His Asn Glu Tyr Thr Ile Ile Asn Ser Ile Glu Gln Asn Ser
945                 950                 955                 960

Gly Trp Lys Leu Cys Ile Arg Asn Gly Asn Ile Glu Trp Ile Leu Gln
                965                 970                 975
```

```
Asp Val Asn Arg Lys Tyr Lys Ser Leu Ile Phe Asp Tyr Ser Glu Ser
            980                 985                 990

Leu Ser His Thr Gly Tyr Thr Asn Lys Trp Phe Phe Val Thr Ile Thr
        995                1000                1005

Asn Asn Ile Met Gly Tyr Met Lys Leu Tyr Ile Asn Gly Glu Leu
   1010                1015                1020

Lys Gln Ser Gln Lys Ile Glu Asp Leu Asp Glu Val Lys Leu Asp
   1025                1030                1035

Lys Thr Ile Val Phe Gly Ile Asp Glu Asn Ile Asp Glu Asn Gln
   1040                1045                1050

Met Leu Trp Ile Arg Asp Phe Asn Ile Phe Ser Lys Glu Leu Ser
   1055                1060                1065

Asn Glu Asp Ile Asn Ile Val Tyr Glu Gly Gln Ile Leu Arg Asn
   1070                1075                1080

Val Ile Lys Asp Tyr Trp Gly Asn Pro Leu Lys Phe Asp Thr Glu
   1085                1090                1095

Tyr Tyr Ile Ile Asn Asp Asn Tyr Ile Asp Arg Tyr Ile Ala Pro
   1100                1105                1110

Glu Ser Asn Val Leu Val Leu Val Arg Tyr Pro Asp Arg Ser Lys
   1115                1120                1125

Leu Tyr Thr Gly Asn Pro Ile Thr Ile Lys Ser Val Ser Asp Lys
   1130                1135                1140

Asn Pro Tyr Ser Arg Ile Leu Asn Gly Asp Asn Ile Ile Leu His
   1145                1150                1155

Met Leu Tyr Asn Ser Arg Lys Tyr Met Ile Ile Arg Asp Thr Asp
   1160                1165                1170

Thr Ile Tyr Ala Thr Gln Gly Gly Glu Cys Ser Gln Asn Cys Val
   1175                1180                1185

Tyr Ala Leu Lys Leu Gln Ser Asn Leu Gly Asn Tyr Gly Ile Gly
   1190                1195                1200

Ile Phe Ser Ile Lys Asn Ile Val Ser Lys Asn Lys Tyr Cys Ser
   1205                1210                1215

Gln Ile Phe Ser Ser Phe Arg Glu Asn Thr Met Leu Leu Ala Asp
   1220                1225                1230

Ile Tyr Lys Pro Trp Arg Phe Ser Phe Lys Asn Ala Tyr Thr Pro
   1235                1240                1245

Val Ala Val Thr Asn Tyr Glu Thr Lys Leu Leu Ser Thr Ser Ser
   1250                1255                1260

Phe Trp Lys Phe Ile Ser Arg Asp Pro Gly Trp Val Glu
   1265                1270                1275

<210> SEQ ID NO 19
<211> LENGTH: 1285
<212> TYPE: PRT
<213> ORGANISM: Clostridium botulinum
<300> PUBLICATION INFORMATION:
<308> DATABASE ACCESSION NUMBER: BAA07477
<300> PUBLICATION INFORMATION:
<308> DATABASE ACCESSION NUMBER: S70582

<400> SEQUENCE: 19

Met Thr Trp Pro Val Lys Asp Phe Asn Tyr Ser Asp Pro Val Asn Asp
1               5                  10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
```

```
                35                  40                  45
Arg Phe Ser Ser Asp Thr Asn Pro Ser Leu Ser Lys Pro Pro Arg Pro
 50                  55                  60

Thr Ser Lys Tyr Gln Ser Tyr Asp Pro Ser Tyr Leu Ser Thr Asp
 65                  70                  75                  80

Glu Gln Lys Asp Thr Phe Leu Lys Gly Ile Lys Leu Phe Lys Arg
                 85                  90                  95

Ile Asn Glu Arg Asp Ile Gly Lys Lys Leu Ile Asn Tyr Leu Val Val
                100                 105                 110

Gly Ser Pro Phe Met Gly Asp Ser Ser Thr Pro Glu Asp Thr Phe Asp
                115                 120                 125

Phe Thr Arg His Thr Thr Asn Ile Ala Val Glu Lys Phe Glu Asn Gly
                130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
                180                 185                 190

Lys Val Ala Pro Glu Phe Leu Leu Thr Phe Ser Asp Val Thr Ser Asn
                195                 200                 205

Gln Ser Ser Ala Val Leu Gly Lys Ser Ile Phe Cys Met Asp Pro Val
210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
                260                 265                 270

Phe Gly Gly Ser Asp Val Glu Ile Ile Pro Gln Ile Glu Arg Leu Gln
                275                 280                 285

Leu Arg Glu Lys Ala Leu Gly His Tyr Lys Asp Ile Ala Lys Arg Leu
290                 295                 300

Asn Asn Ile Asn Lys Thr Ile Pro Ser Ser Trp Ser Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Leu Val Asn Ile Asp Lys Phe Asn Ser Leu Tyr Ser
                340                 345                 350

Asp Leu Thr Asn Val Met Ser Glu Val Ile Tyr Ser Ser Gln Tyr Asn
                355                 360                 365

Val Lys Asn Arg Thr His Tyr Phe Ser Lys His Tyr Leu Pro Val Phe
                370                 375                 380

Ala Asn Ile Leu Asp Asp Asn Ile Tyr Thr Ile Ile Asn Gly Phe Asn
385                 390                 395                 400

Leu Thr Thr Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
                420                 425                 430

Phe Thr Lys Val Cys Leu Arg Leu Thr Arg Asn Ser Arg Asp Asp Ser
                435                 440                 445

Thr Cys Ile Gln Val Lys Asn Asn Thr Leu Pro Tyr Val Ala Asp Lys
450                 455                 460
```

```
Asp Ser Ile Ser Gln Glu Ile Phe Glu Ser Gln Ile Thr Asp Glu
465                 470                 475                 480

Thr Asn Val Glu Asn Tyr Ser Asp Asn Phe Ser Leu Asp Glu Ser Ile
        485                 490                 495

Leu Asp Ala Lys Val Pro Thr Asn Pro Glu Ala Val Asp Pro Leu Leu
            500                 505                 510

Pro Asn Val Asn Met Glu Pro Leu Asn Val Pro Gly Glu Glu Glu Val
        515                 520                 525

Phe Tyr Asp Asp Ile Thr Lys Asp Val Asp Tyr Leu Asn Ser Tyr Tyr
    530                 535                 540

Tyr Leu Glu Ala Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
                565                 570                 575

Phe Leu Pro Ser Leu Ala Glu Lys Val Asn Lys Gly Val Gln Ala Gly
            580                 585                 590

Leu Phe Leu Asn Trp Ala Asn Glu Val Val Glu Asp Phe Thr Thr Asn
        595                 600                 605

Ile Met Lys Lys Asp Thr Leu Asp Lys Ile Ser Asp Val Ser Ala Ile
        610                 615                 620

Ile Pro Tyr Ile Gly Pro Ala Leu Asn Ile Gly Asn Ser Ala Leu Arg
625                 630                 635                 640

Gly Asn Phe Lys Gln Ala Phe Ala Thr Ala Gly Val Ala Phe Leu Leu
                645                 650                 655

Glu Gly Phe Pro Glu Phe Thr Ile Pro Ala Leu Gly Val Phe Thr Phe
            660                 665                 670

Tyr Ser Ser Ile Gln Glu Arg Glu Lys Ile Ile Lys Thr Ile Glu Asn
        675                 680                 685

Cys Leu Glu Gln Arg Val Lys Arg Trp Lys Asp Ser Tyr Gln Trp Met
        690                 695                 700

Val Ser Asn Trp Leu Ser Arg Ile Thr Thr Gln Phe Asn His Ile Ser
705                 710                 715                 720

Tyr Gln Met Tyr Asp Ser Leu Ser Tyr Gln Ala Asp Ala Ile Lys Ala
                725                 730                 735

Lys Ile Asp Leu Glu Tyr Lys Lys Tyr Ser Gly Ser Asp Lys Glu Asn
            740                 745                 750

Ile Lys Ser Gln Val Glu Asn Leu Lys Asn Ser Leu Asp Val Lys Ile
        755                 760                 765

Ser Glu Ala Met Asn Asn Ile Asn Lys Phe Ile Arg Glu Cys Ser Val
        770                 775                 780

Thr Tyr Leu Phe Lys Asn Met Leu Pro Lys Val Ile Asp Glu Leu Asn
785                 790                 795                 800

Lys Phe Asp Leu Lys Thr Lys Thr Glu Leu Ile Asn Leu Ile Asp Ser
                805                 810                 815

His Asn Ile Ile Leu Val Gly Glu Val Asp Arg Leu Lys Ala Lys Val
            820                 825                 830

Asn Glu Ser Phe Glu Asn Thr Ile Pro Phe Asn Ile Phe Ser Tyr Thr
        835                 840                 845

Asn Asn Ser Leu Leu Lys Asp Met Ile Asn Glu Tyr Phe Asn Ser Ile
        850                 855                 860

Asn Asp Ser Lys Ile Leu Ser Leu Gln Asn Lys Lys Asn Thr Leu Met
865                 870                 875                 880
```

```
Asp Thr Ser Gly Tyr Asn Ala Glu Val Arg Val Glu Gly Asn Val Gln
                885                 890                 895

Leu Asn Pro Ile Phe Pro Phe Asp Phe Lys Leu Gly Ser Ser Gly Asp
        900                 905                 910

Asp Arg Gly Lys Ile Ile Val Thr Gln Asn Glu Asn Ile Val Tyr Asn
        915                 920                 925

Ala Met Tyr Glu Ser Phe Ser Ile Ser Phe Trp Ile Arg Ile Asn Lys
        930                 935                 940

Trp Val Ser Asn Leu Pro Gly Tyr Thr Ile Ile Asp Ser Val Lys Asn
945                 950                 955                 960

Asn Ser Gly Trp Ser Ile Gly Ile Ile Ser Asn Phe Leu Val Phe Thr
                965                 970                 975

Leu Lys Gln Asn Glu Asn Ser Glu Gln Asp Ile Asn Phe Ser Tyr Asp
        980                 985                 990

Ile Ser Lys Asn Ala Ala Gly Tyr Asn Lys Trp Phe Phe Val Thr Ile
        995                 1000                1005

Thr Thr Asn Met Met Gly Asn Met Met Ile Tyr Ile Asn Gly Lys
    1010                1015                1020

Leu Ile Asp Thr Ile Lys Val Lys Glu Leu Thr Gly Ile Asn Phe
    1025                1030                1035

Ser Lys Thr Ile Thr Phe Gln Met Asn Lys Ile Pro Asn Thr Gly
    1040                1045                1050

Leu Ile Thr Ser Asp Ser Asp Asn Ile Asn Met Trp Ile Arg Asp
    1055                1060                1065

Phe Tyr Ile Phe Ala Lys Glu Leu Asp Asp Lys Asp Ile Asn Ile
    1070                1075                1080

Leu Phe Asn Ser Leu Gln Tyr Thr Asn Val Val Lys Asp Tyr Trp
    1085                1090                1095

Gly Asn Asp Leu Arg Tyr Asp Lys Glu Tyr Tyr Met Ile Asn Val
    1100                1105                1110

Asn Tyr Met Asn Arg Tyr Met Ser Lys Lys Gly Asn Gly Ile Val
    1115                1120                1125

Phe Asn Thr Arg Lys Asn Asn Asn Asp Phe Asn Glu Gly Tyr Lys
    1130                1135                1140

Ile Ile Ile Lys Arg Ile Arg Gly Asn Thr Asn Asp Thr Arg Val
    1145                1150                1155

Arg Gly Glu Asn Val Leu Tyr Phe Asn Thr Thr Ile Asp Asn Lys
    1160                1165                1170

Gln Tyr Ser Leu Gly Met Tyr Lys Pro Ser Arg Asn Leu Gly Thr
    1175                1180                1185

Asp Leu Val Pro Leu Gly Ala Leu Asp Gln Pro Met Asp Glu Ile
    1190                1195                1200

Arg Lys Tyr Gly Ser Phe Ile Ile Gln Pro Cys Asn Thr Phe Asp
    1205                1210                1215

Tyr Tyr Ala Ser Gln Leu Phe Leu Ser Ser Asn Ala Thr Thr Asn
    1220                1225                1230

Arg Leu Gly Ile Leu Ser Ile Gly Ser Tyr Ser Phe Lys Leu Gly
    1235                1240                1245

Asp Asp Tyr Trp Phe Asn His Glu Tyr Leu Ile Pro Val Ile Lys
    1250                1255                1260

Ile Glu His Tyr Ala Ser Leu Leu Glu Ser Thr Ser Thr His Trp
    1265                1270                1275

Val Phe Val Pro Ala Ser Glu
```

```
                1280                    1285

<210> SEQ ID NO 20
<211> LENGTH: 1285
<212> TYPE: PRT
<213> ORGANISM: Clostridium botulinum
<300> PUBLICATION INFORMATION:
<308> DATABASE ACCESSION NUMBER: BAA90661

<400> SEQUENCE: 20

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Ser Asp Val Glu Ile Ile Pro Gln Ile Glu Arg Leu Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ser Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
```

```
              355                 360                 365
Val Lys Asn Arg Thr His Tyr Phe Ser Lys His Tyr Leu Pro Val Phe
370                 375                 380
Ala Asn Ile Leu Asp Asp Asn Ile Tyr Thr Ile Ile Asn Gly Phe Asn
385                 390                 395                 400
Leu Thr Thr Lys Gly Phe Asn Ile Glu Asn Ser Gly Gln Asn Ile Glu
                405                 410                 415
Arg Asn Pro Ala Leu Gln Lys Leu Ser Ser Glu Ser Val Val Asp Leu
            420                 425                 430
Phe Thr Lys Val Cys Leu Arg Leu Thr Arg Asn Ser Arg Asp Asp Ser
        435                 440                 445
Thr Cys Ile Gln Val Lys Asn Asn Thr Leu Pro Tyr Val Ala Asp Lys
    450                 455                 460
Asp Ser Ile Ser Gln Glu Ile Phe Glu Ser Gln Ile Ile Thr Asp Glu
465                 470                 475                 480
Thr Asn Val Glu Asn Tyr Ser Asp Asn Phe Ser Leu Asp Glu Ser Ile
                485                 490                 495
Leu Asp Ala Lys Val Pro Thr Asn Pro Glu Ala Val Asp Pro Leu Leu
            500                 505                 510
Pro Asn Val Asn Met Glu Pro Leu Asn Val Pro Gly Glu Glu Val
        515                 520                 525
Phe Tyr Asp Asp Ile Thr Lys Asp Val Asp Tyr Leu Asn Ser Tyr Tyr
    530                 535                 540
Tyr Leu Glu Ala Gln Lys Leu Ser Asn Asn Val Glu Asn Ile Thr Leu
545                 550                 555                 560
Thr Thr Ser Val Glu Glu Ala Leu Gly Tyr Ser Asn Lys Ile Tyr Thr
                565                 570                 575
Phe Leu Pro Ser Leu Ala Glu Lys Val Asn Lys Gly Val Gln Ala Gly
            580                 585                 590
Leu Phe Leu Asn Trp Ala Asn Glu Val Val Glu Asp Phe Thr Thr Asn
        595                 600                 605
Ile Met Lys Lys Asp Thr Leu Asp Lys Ile Ser Asp Val Ser Ala Ile
    610                 615                 620
Ile Pro Tyr Ile Gly Pro Ala Leu Asn Ile Gly Asn Ser Ala Leu Arg
625                 630                 635                 640
Gly Asn Phe Lys Gln Ala Phe Ala Thr Ala Gly Val Ala Phe Leu Leu
                645                 650                 655
Glu Gly Phe Pro Glu Phe Thr Ile Pro Ala Leu Gly Val Phe Thr Phe
            660                 665                 670
Tyr Ser Ser Ile Gln Glu Arg Glu Lys Ile Ile Lys Thr Ile Glu Asn
        675                 680                 685
Cys Leu Glu Gln Arg Val Lys Arg Trp Lys Asp Ser Tyr Gln Trp Met
    690                 695                 700
Val Ser Asn Trp Leu Ser Arg Ile Thr Thr Arg Phe Asn His Ile Ser
705                 710                 715                 720
Tyr Gln Met Tyr Asp Ser Leu Ser Tyr Gln Ala Asp Ala Ile Lys Ala
                725                 730                 735
Lys Ile Asp Leu Glu Tyr Lys Lys Tyr Ser Gly Ser Asp Lys Glu Asn
            740                 745                 750
Ile Lys Ser Gln Val Glu Asn Leu Lys Asn Ser Leu Asp Val Lys Ile
        755                 760                 765
Ser Glu Ala Met Asn Asn Ile Asn Lys Phe Ile Arg Glu Cys Ser Val
    770                 775                 780
```

-continued

Thr Tyr Leu Phe Lys Asn Met Leu Pro Lys Val Ile Asp Glu Leu Asn
785                 790                 795                 800

Lys Phe Asp Leu Lys Thr Lys Thr Glu Leu Ile Asn Leu Ile Asp Ser
                805                 810                 815

His Asn Ile Ile Leu Val Gly Glu Val Asp Arg Leu Lys Ala Lys Val
            820                 825                 830

Asn Glu Ser Phe Glu Asn Thr Ile Pro Phe Asn Ile Phe Ser Tyr Thr
        835                 840                 845

Asn Asn Ser Leu Leu Lys Asp Met Ile Asn Glu Tyr Phe Asn Ser Ile
850                 855                 860

Asn Asp Ser Lys Ile Leu Ser Leu Gln Asn Lys Lys Asn Thr Leu Met
865                 870                 875                 880

Asp Thr Ser Gly Tyr Asn Ala Glu Val Arg Val Glu Gly Asn Val Gln
                885                 890                 895

Leu Asn Pro Ile Phe Pro Phe Asp Phe Lys Leu Gly Ser Ser Gly Asp
                900                 905                 910

Asp Arg Gly Lys Val Ile Val Thr Gln Asn Glu Asn Ile Val Tyr Asn
            915                 920                 925

Ala Met Tyr Glu Ser Phe Ser Ile Ser Phe Trp Ile Arg Ile Asn Lys
930                 935                 940

Trp Val Ser Asn Leu Pro Gly Tyr Thr Ile Ile Asp Ser Val Lys Asn
945                 950                 955                 960

Asn Ser Gly Trp Ser Ile Gly Ile Ile Ser Asn Phe Leu Val Phe Thr
                965                 970                 975

Leu Lys Gln Asn Glu Asn Ser Glu Gln Asp Ile Asn Phe Ser Tyr Asp
                980                 985                 990

Ile Ser Lys Asn Ala Ala Gly Tyr Asn Lys Trp Phe Phe Val Thr Ile
            995                 1000                1005

Thr Thr Asn Met Met Gly Asn Met Met Ile Tyr Ile Asn Gly Lys
        1010                1015                1020

Leu Ile Asp Thr Ile Lys Val Lys Glu Leu Thr Gly Ile Asn Phe
        1025                1030                1035

Ser Lys Thr Ile Thr Phe Gln Met Asn Lys Ile Pro Asn Thr Gly
        1040                1045                1050

Leu Ile Thr Ser Asp Ser Asp Asn Ile Asn Met Trp Ile Arg Asp
        1055                1060                1065

Phe Tyr Ile Phe Ala Lys Glu Leu Asp Asp Lys Asp Ile Asn Ile
        1070                1075                1080

Leu Phe Asn Ser Leu Gln Tyr Thr Asn Val Val Lys Asp Tyr Trp
        1085                1090                1095

Gly Asn Asp Leu Arg Tyr Asp Lys Glu Tyr Tyr Met Ile Asn Val
        1100                1105                1110

Asn Tyr Met Asn Arg Tyr Met Ser Lys Lys Gly Asn Gly Ile Val
        1115                1120                1125

Phe Asn Thr Arg Lys Asn Asn Asn Asp Phe Asn Glu Gly Tyr Lys
        1130                1135                1140

Ile Ile Ile Lys Arg Ile Arg Gly Asn Thr Asn Asp Thr Arg Val
        1145                1150                1155

Arg Gly Glu Asn Val Leu Tyr Phe Asn Thr Thr Ile Asp Asn Lys
        1160                1165                1170

Gln Tyr Ser Leu Gly Met Tyr Lys Pro Ser Arg Asn Leu Gly Thr
        1175                1180                1185

```
Asp Leu Val Pro Leu Gly Ala Leu Asp Gln Pro Met Asp Glu Ile
    1190            1195                1200

Arg Lys Tyr Gly Ser Phe Ile Ile Gln Pro Cys Asn Thr Phe Asp
    1205            1210                1215

Tyr Tyr Ala Ser Gln Leu Phe Leu Ser Ser Asn Ala Thr Thr Asn
    1220            1225                1230

Arg Leu Gly Ile Leu Ser Ile Gly Ser Tyr Ser Phe Lys Leu Gly
    1235            1240                1245

Asp Asp Tyr Trp Phe Asn His Glu Tyr Leu Ile Pro Val Ile Lys
    1250            1255                1260

Ile Glu His Tyr Ala Ser Leu Leu Glu Ser Thr Ser Thr His Trp
    1265            1270                1275

Val Phe Val Pro Ala Ser Glu
    1280            1285

<210> SEQ ID NO 21
<211> LENGTH: 1252
<212> TYPE: PRT
<213> ORGANISM: Clostridium botulinum
<300> PUBLICATION INFORMATION:
<308> DATABASE ACCESSION NUMBER: BAB86845
<300> PUBLICATION INFORMATION:
<308> DATABASE ACCESSION NUMBER: CAA44558
<300> PUBLICATION INFORMATION:
<308> DATABASE ACCESSION NUMBER: S21178

<400> SEQUENCE: 21

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
                20                  25                  30

Phe Asn Ile Met Lys Asn Ile Trp Ile Ile Pro Glu Arg Asn Val Ile
            35                  40                  45

Gly Thr Thr Pro Gln Asp Phe His Pro Pro Thr Ser Leu Lys Asn Gly
        50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240
```

-continued

```
Ile Thr Asn Ile Arg Gly Thr Asn Ile Glu Glu Phe Leu Thr Phe Gly
                245                 250                 255
Gly Thr Asp Leu Asn Ile Ile Thr Ser Ala Gln Ser Asn Asp Ile Tyr
                260                 265                 270
Thr Asn Leu Leu Ala Asp Tyr Lys Lys Ile Ala Ser Lys Leu Ser Lys
            275                 280                 285
Val Gln Val Ser Asn Pro Leu Leu Asn Pro Tyr Lys Asp Val Phe Glu
        290                 295                 300
Ala Lys Tyr Gly Leu Asp Lys Asp Ala Ser Gly Ile Tyr Ser Val Asn
305                 310                 315                 320
Ile Asn Lys Phe Asn Asp Ile Phe Lys Lys Leu Tyr Ser Phe Thr Glu
                325                 330                 335
Phe Asp Leu Ala Thr Lys Phe Gln Val Lys Cys Arg Gln Thr Tyr Ile
            340                 345                 350
Gly Gln Tyr Lys Tyr Phe Lys Leu Ser Asn Leu Leu Asn Asp Ser Ile
        355                 360                 365
Tyr Asn Ile Ser Glu Gly Tyr Asn Ile Asn Asn Leu Lys Val Asn Phe
    370                 375                 380
Arg Gly Gln Asn Ala Asn Leu Asn Pro Arg Ile Ile Thr Pro Ile Thr
385                 390                 395                 400
Gly Arg Gly Leu Val Lys Lys Ile Ile Arg Phe Cys Lys Asn Ile Val
                405                 410                 415
Ser Val Lys Gly Ile Arg Lys Ser Ile Cys Ile Glu Ile Asn Asn Gly
            420                 425                 430
Glu Leu Phe Phe Val Ala Ser Glu Asn Ser Tyr Asn Asp Asp Asn Ile
        435                 440                 445
Asn Thr Pro Lys Glu Ile Asp Asp Thr Val Thr Ser Asn Asn Asn Tyr
    450                 455                 460
Glu Asn Asp Leu Asp Gln Val Ile Leu Asn Phe Asn Ser Glu Ser Ala
465                 470                 475                 480
Pro Gly Leu Ser Asp Glu Lys Leu Asn Leu Thr Ile Gln Asn Asp Ala
                485                 490                 495
Tyr Ile Pro Lys Tyr Asp Ser Asn Gly Thr Ser Asp Ile Glu Gln His
            500                 505                 510
Asp Val Asn Glu Leu Asn Val Phe Phe Tyr Leu Asp Ala Gln Lys Val
        515                 520                 525
Pro Glu Gly Glu Asn Asn Val Asn Leu Thr Ser Ser Ile Asp Thr Ala
    530                 535                 540
Leu Leu Glu Gln Pro Lys Ile Tyr Thr Phe Phe Ser Ser Glu Phe Ile
545                 550                 555                 560
Asn Asn Val Asn Lys Pro Val Gln Ala Ala Leu Phe Val Ser Trp Ile
                565                 570                 575
Gln Gln Val Leu Val Asp Phe Thr Thr Glu Ala Asn Gln Lys Ser Thr
            580                 585                 590
Val Asp Lys Ile Ala Asp Ile Ser Ile Val Val Pro Tyr Ile Gly Leu
        595                 600                 605
Ala Leu Asn Ile Gly Asn Glu Ala Gln Lys Gly Asn Phe Lys Asp Ala
    610                 615                 620
Leu Glu Leu Leu Gly Ala Gly Ile Leu Leu Glu Phe Glu Pro Glu Leu
625                 630                 635                 640
Leu Ile Pro Thr Ile Leu Val Phe Thr Ile Lys Ser Phe Leu Gly Ser
                645                 650                 655
```

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
            725                 730                 735

Lys Tyr Asp Ile Lys Gln Ile Glu Asn Glu Leu Asn Gln Lys Val Ser
        740                 745                 750

Ile Ala Met Asn Asn Ile Asp Arg Phe Leu Thr Glu Ser Ser Ile Ser
            755                 760                 765

Tyr Leu Met Lys Leu Ile Asn Glu Val Lys Ile Asn Lys Leu Arg Glu
770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
            805                 810                 815

Asp Thr Leu Asn Asn Ser Ile Pro Phe Lys Leu Ser Ser Tyr Thr Asp
        820                 825                 830

Asp Lys Ile Leu Ile Ser Tyr Phe Asn Lys Phe Phe Lys Arg Ile Lys
            835                 840                 845

Ser Ser Ser Val Leu Asn Met Arg Tyr Lys Asn Asp Lys Tyr Val Asp
850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
            885                 890                 895

Glu Val Asn Ile Ser Gln Asn Asp Tyr Ile Ile Tyr Asp Asn Lys Tyr
        900                 905                 910

Lys Asn Phe Ser Ile Ser Phe Trp Val Arg Ile Pro Asn Tyr Asp Asn
            915                 920                 925

Lys Ile Val Asn Val Asn Asn Glu Tyr Thr Ile Ile Asn Cys Met Arg
930                 935                 940

Asp Asn Asn Ser Gly Trp Lys Val Ser Leu Asn His Asn Glu Ile Ile
945                 950                 955                 960

Trp Thr Leu Gln Asp Asn Ala Gly Ile Asn Gln Lys Leu Ala Phe Asn
            965                 970                 975

Tyr Gly Asn Ala Asn Gly Ile Ser Asp Tyr Ile Asn Lys Trp Ile Phe
        980                 985                 990

Val Thr Ile Thr Asn Asp Arg Leu Gly Asp Ser Lys Leu Tyr Ile Asn
        995                 1000                 1005

Gly Asn Leu Ile Asp Gln Lys Ser Ile Leu Asn Leu Gly Asn Ile
    1010                1015                1020

His Val Ser Asp Asn Ile Leu Phe Lys Ile Val Asn Cys Ser Tyr
    1025                1030                1035

Thr Arg Tyr Ile Gly Ile Arg Tyr Phe Asn Ile Phe Asp Lys Glu
    1040                1045                1050

Leu Asp Glu Thr Glu Ile Gln Thr Leu Tyr Ser Asn Glu Pro Asn
    1055                1060                1065

Thr Asn Ile Leu Lys Asp Phe Trp Gly Asn Tyr Leu Leu Tyr Asp

```
                         1070                1075                1080
Lys Glu Tyr Tyr Leu Leu Asn Val Leu Lys Pro Asn Asn Phe Ile
        1085                1090                1095

Asp Arg Arg Lys Asp Ser Thr Leu Ser Ile Asn Asn Ile Arg Ser
    1100                1105                1110

Thr Ile Leu Leu Ala Asn Arg Leu Tyr Ser Gly Ile Lys Val Lys
        1115                1120                1125

Ile Gln Arg Val Asn Ser Ser Thr Asn Asp Asn Leu Val Arg
    1130                1135                1140

Lys Asn Asp Gln Val Tyr Ile Asn Phe Val Ala Ser Lys Thr His
1145                1150                1155

Leu Phe Pro Leu Tyr Ala Asp Thr Ala Thr Thr Asn Lys Glu Lys
    1160                1165                1170

Thr Ile Lys Ile Ser Ser Ser Gly Asn Arg Phe Asn Gln Val Val
        1175                1180                1185

Val Met Asn Ser Val Gly Asn Asn Cys Thr Met Asn Phe Lys Asn
    1190                1195                1200

Asn Asn Gly Asn Asn Ile Gly Leu Leu Gly Phe Lys Ala Asp Thr
        1205                1210                1215

Val Val Ala Ser Thr Trp Tyr Tyr Thr His Met Arg Asp His Thr
    1220                1225                1230

Asn Ser Asn Gly Cys Phe Trp Asn Phe Ile Ser Glu Glu His Gly
    1235                1240                1245

Trp Gln Glu Lys
    1250

<210> SEQ ID NO 22
<211> LENGTH: 1251
<212> TYPE: PRT
<213> ORGANISM: Clostridium botulinum
<300> PUBLICATION INFORMATION:
<308> DATABASE ACCESSION NUMBER: CAA43999
<300> PUBLICATION INFORMATION:
<308> DATABASE ACCESSION NUMBER: Q00496

<400> SEQUENCE: 22

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160
```

-continued

```
Asn Ser Ser Asn Ile Ser Leu Arg Asn Asn Tyr Met Pro Ser Asn His
                165                 170                 175
Arg Phe Gly Ser Ile Ala Ile Val Thr Phe Ser Pro Glu Tyr Ser Phe
            180                 185                 190
Arg Phe Asn Asp Asn Cys Met Asn Glu Phe Ile Gln Asp Pro Ala Leu
        195                 200                 205
Thr Leu Met His Glu Leu Ile His Ser Leu His Gly Leu Tyr Gly Ala
    210                 215                 220
Lys Gly Ile Thr Thr Lys Tyr Thr Ile Thr Gln Lys Gln Asn Pro Leu
225                 230                 235                 240
Ile Thr Asn Ile Arg Gly Thr Asn Ile Glu Glu Phe Leu Thr Phe Gly
                245                 250                 255
Gly Thr Asp Leu Asn Ile Ile Thr Ser Ala Gln Ser Asn Asp Ile Tyr
            260                 265                 270
Thr Asn Leu Leu Ala Asp Tyr Lys Lys Ile Ala Ser Lys Leu Ser Lys
        275                 280                 285
Val Gln Val Ser Asn Pro Leu Leu Asn Pro Tyr Lys Asp Val Phe Glu
    290                 295                 300
Ala Lys Tyr Gly Leu Asp Lys Asp Ala Ser Gly Ile Tyr Ser Val Asn
305                 310                 315                 320
Ile Asn Lys Phe Asn Asp Ile Phe Lys Lys Leu Tyr Ser Phe Thr Glu
                325                 330                 335
Phe Asp Leu Arg Thr Lys Phe Gln Val Lys Cys Arg Gln Thr Tyr Ile
            340                 345                 350
Gly Gln Tyr Lys Tyr Phe Lys Leu Ser Asn Leu Leu Asn Asp Ser Ile
        355                 360                 365
Tyr Asn Ile Ser Glu Gly Tyr Asn Ile Asn Asn Leu Lys Val Asn Phe
    370                 375                 380
Arg Gly Gln Asn Ala Asn Leu Asn Pro Arg Ile Ile Thr Pro Ile Thr
385                 390                 395                 400
Gly Arg Gly Leu Val Lys Lys Ile Ile Arg Phe Cys Lys Asn Ile Val
                405                 410                 415
Ser Val Lys Gly Ile Arg Lys Ser Ile Cys Ile Glu Ile Asn Asn Gly
            420                 425                 430
Glu Leu Phe Phe Val Ala Ser Glu Asn Ser Tyr Asn Asp Asp Asn Ile
        435                 440                 445
Asn Thr Pro Lys Glu Ile Asp Asp Thr Val Thr Ser Asn Asn Asn Tyr
    450                 455                 460
Glu Asn Asp Leu Asp Gln Val Ile Leu Asn Phe Asn Ser Glu Ser Ala
465                 470                 475                 480
Pro Gly Leu Ser Asp Glu Lys Leu Asn Leu Thr Ile Gln Asn Asp Ala
                485                 490                 495
Tyr Ile Pro Lys Tyr Asp Ser Asn Gly Thr Ser Asp Ile Glu Gln His
            500                 505                 510
Asp Val Asn Glu Leu Asn Val Phe Phe Tyr Leu Asp Ala Gln Lys Val
        515                 520                 525
Pro Glu Gly Glu Asn Asn Val Asn Leu Thr Ser Ser Ile Asp Thr Ala
    530                 535                 540
Leu Leu Glu Gln Pro Lys Ile Tyr Thr Phe Phe Ser Ser Glu Phe Ile
545                 550                 555                 560
Asn Asn Val Asn Lys Pro Val Gln Ala Ala Leu Phe Val Ser Trp Ile
                565                 570                 575
```

```
Gln Gln Val Leu Val Asp Phe Thr Thr Glu Ala Asn Gln Lys Ser Thr
                580                 585                 590

Val Asp Lys Ile Ala Asp Ile Ser Ile Val Pro Tyr Ile Gly Leu
            595                 600             605

Ala Leu Asn Ile Gly Asn Glu Ala Gln Lys Gly Asn Phe Lys Asp Ala
            610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
            675                 680                 685

Trp Met Thr Lys Ile Asn Thr Gln Phe Asn Lys Arg Lys Glu Gln Met
        690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
            755                 760                 765

Tyr Leu Met Lys Ile Ile Asn Glu Val Lys Ile Asn Lys Leu Arg Glu
        770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
            835                 840                 845

Ser Ser Ser Val Leu Asn Met Arg Tyr Lys Asn Asp Lys Tyr Val Asp
850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
            915                 920                 925

Lys Ile Val Asn Val Asn Asn Glu Tyr Thr Ile Ile Asn Cys Met Arg
        930                 935                 940

Asp Asn Asn Ser Gly Trp Lys Val Ser Leu Asn His Asn Glu Ile Ile
945                 950                 955                 960

Trp Thr Phe Glu Asp Asn Arg Gly Ile Asn Gln Lys Leu Ala Phe Asn
                965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu  Gly Asp Ser Lys Leu  Tyr Ile Asn
```

Gly Asn Leu Ile Asp Gln Lys Ser Ile Leu Asn Leu Gly Asn Ile
             995                 1000                1005

His Val Ser Asp Asn Ile Leu Phe Lys Ile Val Asn Cys Ser Tyr
    1010                1015                1020

Thr Arg Tyr Ile Gly Ile Arg Tyr Phe Asn Ile Phe Asp Lys Glu
    1025                1030                1035

Leu Asp Glu Thr Glu Ile Gln Thr Leu Tyr Ser Asn Glu Pro Asn
    1040                1045                1050

Thr Asn Ile Leu Lys Asp Phe Trp Gly Asn Tyr Leu Leu Tyr Asp
    1055                1060                1065

Lys Glu Tyr Tyr Leu Leu Asn Val Leu Lys Pro Asn Asn Phe Ile
    1070                1075                1080

Asp Arg Arg Lys Asp Ser Thr Leu Ser Ile Asn Asn Ile Arg Ser
    1085                1090                1095

Thr Ile Leu Leu Ala Asn Arg Leu Tyr Ser Gly Ile Lys Val Lys
    1100                1105                1110

Ile Gln Arg Val Asn Asn Ser Ser Thr Asn Asp Asn Leu Val Arg
    1115                1120                1125

Lys Asn Asp Gln Val Tyr Ile Asn Phe Val Ala Ser Lys Thr His
    1130                1135                1140

Leu Phe Pro Leu Tyr Ala Asp Thr Ala Thr Thr Asn Lys Glu Lys
    1145                1150                1155

Thr Ile Lys Ile Ser Ser Ser Gly Asn Arg Phe Asn Gln Val Val
    1160                1165                1170

Val Met Asn Ser Val Gly Asn Cys Thr Met Asn Phe Lys Asn Asn
    1175                1180                1185

Asn Gly Asn Asn Ile Gly Leu Leu Gly Phe Lys Ala Asp Thr Val
    1190                1195                1200

Val Ala Ser Thr Trp Tyr Tyr Thr His Met Arg Asp His Thr Asn
    1205                1210                1215

Ser Asn Gly Cys Phe Trp Asn Phe Ile Ser Glu Glu His Gly Trp
    1220                1225                1230

Gln Glu Lys
    1235                1240                1245

Gln Glu Lys
    1250

<210> SEQ ID NO 23
<211> LENGTH: 1251
<212> TYPE: PRT
<213> ORGANISM: Clostridium butyricum
<300> PUBLICATION INFORMATION:
<308> DATABASE ACCESSION NUMBER: CAA43998
<300> PUBLICATION INFORMATION:
<308> DATABASE ACCESSION NUMBER: JH0256
<300> PUBLICATION INFORMATION:
<308> DATABASE ACCESSION NUMBER: P30995

<400> SEQUENCE: 23

Met Pro Thr Ile Asn Ser Phe Asn Tyr Asn Asp Pro Val Asn Asn Arg
1               5                   10                  15

Thr Ile Leu Tyr Ile Lys Pro Gly Gly Cys Gln Gln Phe Tyr Lys Ser
            20                  25                  30

Phe Asn Ile Met Lys Asn Ile Trp Ile Ile Pro Glu Arg Asn Val Ile
        35                  40                  45

Gly Thr Ile Pro Gln Asp Phe Leu Pro Pro Thr Ser Leu Lys Asn Gly
    50                  55                  60

```
Asp Ser Ser Tyr Tyr Asp Pro Asn Tyr Leu Gln Ser Asp Gln Glu Lys
 65                  70                  75                  80

Asp Lys Phe Leu Lys Ile Val Thr Lys Ile Phe Asn Arg Ile Asn Asp
                 85                  90                  95

Asn Leu Ser Gly Arg Ile Leu Leu Glu Glu Leu Ser Lys Ala Asn Pro
            100                 105                 110

Tyr Leu Gly Asn Asp Asn Thr Pro Asp Gly Asp Phe Ile Ile Asn Asp
        115                 120                 125

Ala Ser Ala Val Pro Ile Gln Phe Ser Asn Gly Ser Gln Ser Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Lys Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
    450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
```

```
                485                 490                 495
Tyr Ile Pro Lys Tyr Asp Ser Asn Gly Thr Ser Asp Ile Glu Gln His
            500                 505                 510
Asp Val Asn Glu Leu Asn Val Phe Phe Tyr Leu Asp Ala Gln Lys Val
            515                 520                 525
Pro Glu Gly Glu Asn Asn Val Asn Leu Thr Ser Ser Ile Asp Thr Ala
            530                 535                 540
Leu Leu Glu Gln Pro Lys Ile Tyr Thr Phe Phe Ser Ser Glu Phe Ile
545                 550                 555                 560
Asn Asn Val Asn Lys Pro Val Gln Ala Ala Leu Phe Val Gly Trp Ile
                565                 570                 575
Gln Gln Val Leu Val Asp Phe Thr Thr Glu Ala Asn Gln Lys Ser Thr
            580                 585                 590
Val Asp Lys Ile Ala Asp Ile Ser Ile Val Val Pro Tyr Ile Gly Leu
            595                 600                 605
Ala Leu Asn Ile Gly Asn Glu Ala Gln Lys Gly Asn Phe Lys Asp Ala
            610                 615                 620
Leu Glu Leu Leu Gly Ala Gly Ile Leu Leu Glu Phe Glu Pro Glu Leu
625                 630                 635                 640
Leu Ile Pro Thr Ile Leu Val Phe Thr Ile Lys Ser Phe Leu Gly Ser
                645                 650                 655
Ser Asp Asn Lys Asn Lys Val Ile Lys Ala Ile Asn Asn Ala Leu Lys
            660                 665                 670
Glu Arg Asp Glu Lys Trp Lys Glu Val Tyr Ser Phe Ile Val Ser Asn
            675                 680                 685
Trp Met Thr Lys Ile Asn Thr Gln Phe Asn Lys Arg Lys Glu Gln Met
            690                 695                 700
Tyr Gln Ala Leu Gln Asn Gln Val Asn Ala Leu Lys Ala Ile Ile Glu
705                 710                 715                 720
Ser Lys Tyr Asn Ser Tyr Thr Leu Glu Glu Lys Asn Glu Leu Thr Asn
            725                 730                 735
Lys Tyr Asp Ile Glu Gln Ile Glu Asn Glu Leu Asn Gln Lys Val Ser
            740                 745                 750
Ile Ala Met Asn Asn Ile Asp Arg Phe Leu Thr Glu Ser Ser Ile Ser
            755                 760                 765
Tyr Leu Met Lys Leu Ile Asn Glu Val Lys Ile Asn Lys Leu Arg Glu
            770                 775                 780
Tyr Asp Glu Asn Val Lys Thr Tyr Leu Leu Asp Tyr Ile Ile Lys His
785                 790                 795                 800
Gly Ser Ile Leu Gly Glu Ser Gln Gln Glu Leu Asn Ser Met Val Ile
            805                 810                 815
Asp Thr Leu Asn Asn Ser Ile Pro Phe Lys Leu Ser Ser Tyr Thr Asp
            820                 825                 830
Asp Lys Ile Leu Ile Ser Tyr Phe Asn Lys Phe Phe Lys Arg Ile Lys
            835                 840                 845
Ser Ser Ser Val Leu Asn Met Arg Tyr Lys Asn Asp Lys Tyr Val Asp
            850                 855                 860
Thr Ser Gly Tyr Asp Ser Asn Ile Asn Ile Asn Gly Asp Val Tyr Lys
865                 870                 875                 880
Tyr Pro Thr Asn Lys Asn Gln Phe Gly Ile Tyr Asn Asp Lys Leu Ser
            885                 890                 895
Glu Val Asn Ile Ser Gln Asn Asp Tyr Ile Ile Tyr Asp Asn Lys Tyr
            900                 905                 910
```

```
Lys Asn Phe Ser Ile Ser Phe Trp Val Arg Ile Pro Asn Tyr Asp Asn
        915                 920                 925

Lys Ile Val Asn Val Asn Asn Glu Tyr Thr Ile Ile Asn Cys Met Arg
930                 935                 940

Asp Asn Asn Ser Gly Trp Lys Val Ser Leu Asn His Asn Glu Ile Ile
945                 950                 955                 960

Trp Thr Leu Gln Asp Asn Ser Gly Ile Asn Gln Lys Leu Ala Phe Asn
        965                 970                 975

Tyr Gly Asn Ala Asn Gly Ile Ser Asp Tyr Ile Asn Lys Trp Ile Phe
        980                 985                 990

Val Thr Ile Thr Asn Asp Arg Leu  Gly Asp Ser Lys Leu  Tyr Ile Asn
        995                 1000                1005

Gly Asn  Leu Ile Asp Lys Lys  Ser Ile Leu Asn Leu  Gly Asn Ile
    1010                1015                1020

His Val  Ser Asp Asn Ile Leu  Phe Lys Ile Val Asn  Cys Ser Tyr
    1025                1030                1035

Thr Arg  Tyr Ile Gly Ile Arg  Tyr Phe Asn Ile Phe  Asp Lys Glu
    1040                1045                1050

Leu Asp  Glu Thr Glu Ile Gln  Thr Leu Tyr Asn Asn  Glu Pro Asn
    1055                1060                1065

Ala Asn  Ile Leu Lys Asp Phe  Trp Gly Asn Tyr Leu  Leu Tyr Asp
    1070                1075                1080

Lys Glu  Tyr Tyr Leu Leu Asn  Val Leu Lys Pro Asn  Asn Phe Ile
    1085                1090                1095

Asn Arg  Arg Thr Asp Ser Thr  Leu Ser Ile Asn Asn  Ile Arg Ser
    1100                1105                1110

Thr Ile  Leu Leu Ala Asn Arg  Leu Tyr Ser Gly Ile  Lys Val Lys
    1115                1120                1125

Ile Gln  Arg Val Asn Asn Ser  Ser Thr Asn Asp Asn  Leu Val Arg
    1130                1135                1140

Lys Asn  Asp Gln Val Tyr Ile  Asn Phe Val Ala Ser  Lys Thr His
    1145                1150                1155

Leu Leu  Pro Leu Tyr Ala Asp  Thr Ala Thr Thr Asn  Lys Glu Lys
    1160                1165                1170

Thr Ile  Lys Ile Ser Ser Ser  Gly Asn Arg Phe Asn  Gln Val Val
    1175                1180                1185

Val Met  Asn Ser Val Gly Asn  Cys Thr Met Asn Phe  Lys Asn Asn
    1190                1195                1200

Asn Gly  Asn Asn Ile Gly Leu  Leu Gly Phe Lys Ala  Asp Thr Val
    1205                1210                1215

Val Ala  Ser Thr Trp Tyr Tyr  Thr His Met Arg Asp  Asn Thr Asn
    1220                1225                1230

Ser Asn  Gly Phe Phe Trp Asn  Phe Ile Ser Glu Glu  His Gly Trp
    1235                1240                1245

Gln Glu  Lys
    1250

<210> SEQ ID NO 24
<211> LENGTH: 1274
<212> TYPE: PRT
<213> ORGANISM: Clostridium botulinum
<300> PUBLICATION INFORMATION:
<308> DATABASE ACCESSION NUMBER: 1904210A
<300> PUBLICATION INFORMATION:
<308> DATABASE ACCESSION NUMBER: AAA23263
```

<300> PUBLICATION INFORMATION:
<308> DATABASE ACCESSION NUMBER: I40813
<300> PUBLICATION INFORMATION:
<308> DATABASE ACCESSION NUMBER: P30996

<400> SEQUENCE: 24

```
Met Pro Val Ala Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asn Pro Ser Asp Phe Asp Pro Pro Ala Ser
    50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Lys Val Leu Leu Gln Glu Ile Ser
            100                 105                 110

Tyr Ala Lys Pro Tyr Leu Gly Asn Asp His Thr Pro Ile Asp Glu Phe
        115                 120                 125

Ser Pro Val Thr Arg Thr Thr Ser Val Asn Ile Lys Leu Ser Thr Asn
130                 135                 140

Val Glu Ser Ser Met Leu Leu Asn Leu Leu Val Leu Gly Ala Gly Pro
145                 150                 155                 160

Asp Ile Phe Glu Ser Cys Cys Tyr Pro Val Arg Lys Leu Ile Asp Pro
                165                 170                 175

Asp Val Val Tyr Asp Pro Ser Asn Tyr Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly His Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Glu Glu Thr Ile Glu Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Glu Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ser Asp Leu Ala Asn Lys Phe Lys Val Lys Cys Arg Asn Thr Tyr
        355                 360                 365

Phe Ile Lys Tyr Glu Phe Leu Lys Val Pro Asn Leu Leu Asp Asp Asp
    370                 375                 380
```

```
Ile Tyr Thr Val Ser Glu Gly Phe Asn Ile Gly Asn Leu Ala Val Asn
385                 390                 395                 400

Asn Arg Gly Gln Ser Ile Lys Leu Asn Pro Lys Ile Ile Asp Ser Ile
            405                 410                 415

Pro Asp Lys Gly Leu Val Glu Lys Ile Val Lys Phe Cys Lys Ser Val
            420                 425                 430

Ile Pro Arg Lys Gly Thr Lys Ala Pro Pro Arg Leu Cys Ile Arg Val
            435                 440                 445

Asn Asn Ser Glu Leu Phe Phe Val Ala Ser Glu Ser Ser Tyr Asn Glu
            450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
            485                 490                 495

Gln Thr Ile Pro Gln Ile Ser Asn Arg Thr Leu Asn Thr Leu Val Gln
            500                 505                 510

Asp Asn Ser Tyr Val Pro Arg Tyr Asp Ser Asn Gly Thr Ser Glu Ile
            515                 520                 525

Glu Glu Tyr Asp Val Val Asp Phe Asn Val Phe Phe Tyr Leu His Ala
            530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Asp Ile Phe Phe Ser Ser Glu
            565                 570                 575

Phe Ile Asp Thr Ile Asn Lys Pro Val Asn Ala Ala Leu Phe Ile Asp
            580                 585                 590

Trp Ile Ser Lys Val Ile Arg Asp Phe Thr Thr Glu Ala Thr Gln Lys
            595                 600                 605

Ser Thr Val Asp Lys Ile Ala Asp Ile Ser Leu Ile Val Pro Tyr Val
            610                 615                 620

Gly Leu Ala Leu Asn Ile Ile Ile Glu Ala Lys Gly Asn Phe Glu
625                 630                 635                 640

Glu Ala Phe Glu Leu Leu Gly Val Gly Ile Leu Leu Glu Phe Val Pro
            645                 650                 655

Glu Leu Thr Ile Pro Val Ile Leu Val Phe Thr Ile Lys Ser Tyr Ile
            660                 665                 670

Asp Ser Tyr Glu Asn Lys Asn Lys Ala Ile Lys Ala Ile Asn Asn Ser
            675                 680                 685

Leu Ile Glu Arg Glu Ala Lys Trp Lys Glu Ile Tyr Ser Trp Ile Val
            690                 695                 700

Ser Asn Trp Leu Thr Arg Ile Asn Thr Gln Phe Asn Lys Arg Lys Glu
705                 710                 715                 720

Gln Met Tyr Gln Ala Leu Gln Asn Gln Val Asp Ala Ile Lys Thr Ala
            725                 730                 735

Ile Glu Tyr Lys Tyr Asn Asn Tyr Thr Ser Asp Glu Lys Asn Arg Leu
            740                 745                 750

Glu Ser Glu Tyr Asn Ile Asn Asn Ile Glu Glu Glu Leu Asn Lys Lys
            755                 760                 765

Val Ser Leu Ala Met Lys Asn Ile Glu Arg Phe Met Thr Glu Ser Ser
            770                 775                 780

Ile Ser Tyr Leu Met Lys Leu Ile Asn Glu Ala Lys Val Gly Lys Leu
785                 790                 795                 800

Lys Lys Tyr Asp Asn His Val Lys Ser Asp Leu Leu Asn Tyr Ile Leu
```

-continued

```
                805                 810                 815
Asp His Arg Ser Ile Leu Gly Glu Gln Thr Asn Glu Leu Ser Asp Leu
            820                 825                 830
Val Thr Ser Thr Leu Asn Ser Ser Ile Pro Phe Glu Leu Ser Ser Tyr
            835                 840                 845
Thr Asn Asp Lys Ile Leu Ile Ile Tyr Phe Asn Arg Leu Tyr Lys Lys
        850                 855                 860
Ile Lys Asp Ser Ser Ile Leu Asp Met Arg Tyr Glu Asn Asn Lys Phe
865                 870                 875                 880
Ile Asp Ile Ser Gly Tyr Gly Ser Asn Ile Ser Ile Asn Gly Asn Val
                885                 890                 895
Tyr Ile Tyr Ser Thr Asn Arg Asn Gln Phe Gly Ile Tyr Asn Ser Arg
                900                 905                 910
Leu Ser Glu Val Asn Ile Ala Gln Asn Asn Asp Ile Ile Tyr Asn Ser
            915                 920                 925
Arg Tyr Gln Asn Phe Ser Ile Ser Phe Trp Val Arg Ile Pro Lys His
        930                 935                 940
Tyr Lys Pro Met Asn His Asn Arg Glu Tyr Thr Ile Ile Asn Cys Met
945                 950                 955                 960
Gly Asn Asn Asn Ser Gly Trp Lys Ile Ser Leu Arg Thr Val Arg Asp
                965                 970                 975
Cys Glu Ile Ile Trp Thr Leu Gln Asp Thr Ser Gly Asn Lys Glu Asn
            980                 985                 990
Leu Ile Phe Arg Tyr Glu Glu Leu Asn Arg Ile Ser Asn Tyr Ile Asn
        995                 1000                1005
Lys Trp Ile Phe Val Thr Ile Thr Asn Asn Arg Leu Gly Asn Ser
    1010                1015                1020
Arg Ile Tyr Ile Asn Gly Asn Leu Ile Val Glu Lys Ser Ile Ser
    1025                1030                1035
Asn Leu Gly Asp Ile His Val Ser Asp Asn Ile Leu Phe Lys Ile
    1040                1045                1050
Val Gly Cys Asp Asp Glu Thr Tyr Val Gly Ile Arg Tyr Phe Lys
    1055                1060                1065
Val Phe Asn Thr Glu Leu Asp Lys Thr Glu Ile Glu Thr Leu Tyr
    1070                1075                1080
Ser Asn Glu Pro Asp Pro Ser Ile Leu Lys Asn Tyr Trp Gly Asn
    1085                1090                1095
Tyr Leu Leu Tyr Asn Lys Lys Tyr Tyr Leu Phe Asn Leu Leu Arg
    1100                1105                1110
Lys Asp Lys Tyr Ile Thr Leu Asn Ser Gly Ile Leu Asn Ile Asn
    1115                1120                1125
Gln Gln Arg Gly Val Thr Glu Gly Ser Val Phe Leu Asn Tyr Lys
    1130                1135                1140
Leu Tyr Glu Gly Val Glu Val Ile Ile Arg Lys Asn Gly Pro Ile
    1145                1150                1155
Asp Ile Ser Asn Thr Asp Asn Phe Val Arg Lys Asn Asp Leu Ala
    1160                1165                1170
Tyr Ile Asn Val Val Asp Arg Gly Val Glu Tyr Arg Leu Tyr Ala
    1175                1180                1185
Asp Thr Lys Ser Glu Lys Glu Lys Ile Ile Arg Thr Ser Asn Leu
    1190                1195                1200
Asn Asp Ser Leu Gly Gln Ile Ile Val Met Asp Ser Ile Gly Asn
    1205                1210                1215
```

```
Asn Cys Thr Met Asn Phe Gln Asn Asn Asn Gly Ser Asn Ile Gly
    1220            1225                1230

Leu Leu Gly Phe His Ser Asn Asn Leu Val Ala Ser Ser Trp Tyr
    1235            1240                1245

Tyr Asn Asn Ile Arg Arg Asn Thr Ser Ser Asn Gly Cys Phe Trp
    1250            1255                1260

Ser Ser Ile Ser Lys Glu Asn Gly Trp Lys Glu
    1265            1270

<210> SEQ ID NO 25
<211> LENGTH: 1280
<212> TYPE: PRT
<213> ORGANISM: Clostridium botulinum
<300> PUBLICATION INFORMATION:
<308> DATABASE ACCESSION NUMBER: CAA73972

<400> SEQUENCE: 25

Met Pro Val Val Ile Asn Ser Phe Asn Tyr Asn Asp Pro Val Asn Asp
1               5                   10                  15

Glu Thr Ile Leu Tyr Met Gln Lys Pro Tyr Glu Glu Arg Ser Arg Lys
                20                  25                  30

Tyr Tyr Lys Ala Phe Glu Ile Met Pro Asn Val Trp Ile Met Pro Glu
            35                  40                  45

Arg Asp Thr Ile Gly Thr Lys Pro Asp Glu Phe Gln Val Pro Asp Ser
        50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Met Ile Lys Leu Phe Asn
                85                  90                  95

Arg Ile Asn Ser Asn Pro Thr Gly Lys Val Leu Leu Glu Glu Val Ser
            100                 105                 110

Asn Ala Arg Pro Tyr Leu Gly Asp Asp Asp Thr Leu Ile Asn Glu Phe
        115                 120                 125

Leu Pro Val Asn Val Thr Thr Ser Val Asn Ile Lys Phe Ser Thr Asp
130                 135                 140

Val Glu Ser Ser Ile Ile Ser Asn Leu Leu Val Leu Gly Ala Gly Pro
145                 150                 155                 160

Asp Ile Phe Lys Ala Tyr Cys Thr Pro Leu Val Arg Phe Asn Lys Ser
                165                 170                 175

Asp Lys Leu Ile Glu Pro Ser Asn His Gly Phe Gly Ser Ile Asn Ile
            180                 185                 190

Leu Thr Phe Ser Pro Glu Tyr Glu His Ile Phe Asn Asp Ile Ser Gly
        195                 200                 205

Gly Asn His Asn Ser Thr Glu Ser Phe Ile Ala Asp Pro Ala Ile Ser
    210                 215                 220

Leu Ala His Glu Leu Ile His Ala Leu His Gly Leu Tyr Gly Ala Lys
225                 230                 235                 240

Ala Val Thr His Lys Glu Ser Leu Val Ala Glu Arg Gly Pro Leu Met
                245                 250                 255

Ile Ala Glu Lys Pro Ile Arg Leu Glu Glu Phe Leu Thr Phe Gly Gly
            260                 265                 270

Glu Asp Leu Asn Ile Ile Pro Ser Ala Met Lys Glu Lys Ile Tyr Asn
        275                 280                 285

Asp Leu Leu Ala Asn Tyr Glu Lys Ile Ala Thr Arg Leu Arg Glu Val
    290                 295                 300
```

```
Asn Thr Ala Pro Pro Gly Tyr Asp Ile Asn Glu Tyr Lys Asp Tyr Phe
305                 310                 315                 320

Gln Trp Lys Tyr Gly Leu Asp Arg Asn Ala Asp Gly Ser Tyr Thr Val
            325                 330                 335

Asn Arg Asn Lys Phe Asn Glu Ile Tyr Lys Lys Leu Tyr Ser Phe Thr
        340                 345                 350

Glu Ile Asp Leu Ala Asn Lys Phe Lys Val Lys Cys Arg Asn Thr Tyr
    355                 360                 365

Phe Ile Lys Tyr Gly Phe Val Lys Val Pro Asn Leu Leu Asp Asp Asp
370                 375                 380

Ile Tyr Thr Val Ser Glu Gly Phe Asn Ile Gly Asn Leu Ala Val Asn
385                 390                 395                 400

Asn Arg Gly Gln Asn Ile Asn Leu Asn Pro Lys Ile Ile Asp Ser Ile
            405                 410                 415

Pro Asp Lys Gly Leu Val Glu Lys Ile Ile Lys Phe Cys Lys Ser Ile
        420                 425                 430

Ile Pro Arg Lys Gly Thr Lys Gln Ser Pro Ser Leu Cys Ile Arg Val
    435                 440                 445

Asn Asn Arg Glu Leu Phe Phe Val Ala Ser Glu Ser Ser Tyr Asn Glu
450                 455                 460

Ser Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
            485                 490                 495

Glu Thr Ile Pro Gln Ile Ser Asn Arg Thr Leu Asn Thr Leu Val Gln
        500                 505                 510

Asp Asn Ser Tyr Val Pro Arg Tyr Asp Ser Asn Gly Thr Ser Glu Ile
    515                 520                 525

Glu Glu Tyr Asp Val Val Asp Phe Asn Val Phe Phe Tyr Leu His Ala
530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Val Tyr Thr Phe Phe Ser Ser
            565                 570                 575

Glu Phe Ile Asp Thr Ile Asn Lys Pro Val Asn Ala Ala Leu Phe Ile
        580                 585                 590

Asp Trp Ile Ser Lys Val Ile Arg Asp Phe Thr Thr Glu Ala Thr Gln
    595                 600                 605

Lys Ser Thr Val Asp Lys Ile Ala Asp Ile Ser Leu Ile Val Pro Tyr
610                 615                 620

Val Gly Leu Ala Leu Asn Ile Val Ile Glu Ala Glu Lys Gly Asn Phe
625                 630                 635                 640

Glu Glu Ala Phe Glu Leu Leu Gly Ala Gly Ile Leu Leu Glu Phe Val
            645                 650                 655

Pro Glu Leu Thr Ile Pro Val Ile Leu Val Phe Thr Ile Lys Ser Tyr
        660                 665                 670

Ile Asp Ser Tyr Glu Asn Lys Asn Lys Ala Ile Lys Ala Ile Asn Asn
    675                 680                 685

Ser Leu Ile Glu Arg Glu Ala Lys Trp Lys Glu Ile Tyr Ser Trp Ile
690                 695                 700

Val Ser Asn Trp Leu Thr Arg Ile Asn Thr Gln Phe Asn Lys Arg Lys
705                 710                 715                 720
```

-continued

```
Glu Gln Met Tyr Gln Ala Leu Gln Asn Gln Val Asp Ala Ile Lys Thr
            725                 730                 735
Ala Ile Glu Tyr Lys Tyr Asn Asn Tyr Thr Ser Asp Glu Lys Asn Arg
            740                 745                 750
Leu Glu Ser Lys Tyr Asn Ile Asn Asn Ile Glu Glu Glu Leu Asn Lys
            755                 760                 765
Lys Val Ser Leu Ala Met Lys Asn Ile Glu Arg Phe Met Thr Glu Ser
            770                 775                 780
Ser Ile Ser Tyr Leu Met Lys Leu Ile Asn Glu Ala Glu Val Gly Lys
785                 790                 795                 800
Leu Lys Glu Tyr Asp Lys His Val Lys Ser Asp Leu Leu Asp Tyr Ile
                805                 810                 815
Leu Tyr His Lys Leu Ile Leu Gly Glu Gln Thr Lys Glu Leu Ile Asp
            820                 825                 830
Leu Val Thr Ser Thr Leu Asn Ser Ser Ile Pro Phe Glu Leu Ser Ser
            835                 840                 845
Tyr Thr Asn Asp Lys Ile Leu Ile Ile Tyr Phe Asn Arg Leu Tyr Lys
            850                 855                 860
Lys Ile Lys Asp Ser Ser Ile Leu Asp Met Arg Tyr Glu Asn Asn Lys
865                 870                 875                 880
Phe Ile Asp Ile Ser Gly Tyr Gly Ser Asn Ile Ser Ile Asn Gly Asn
                885                 890                 895
Val Tyr Ile Tyr Ser Thr Asn Arg Asn Gln Phe Gly Ile Tyr Ser Gly
                900                 905                 910
Arg Leu Ser Glu Val Asn Ile Ala Gln Asn Asn Asp Ile Ile Tyr Asn
            915                 920                 925
Ser Arg Tyr Gln Asn Phe Ser Ile Ser Phe Trp Val Thr Ile Pro Lys
930                 935                 940
His Tyr Arg Pro Met Asn Arg Asn Arg Glu Tyr Thr Ile Ile Asn Cys
945                 950                 955                 960
Met Gly Asn Asn Asn Ser Gly Trp Lys Ile Ser Leu Arg Thr Ile Arg
                965                 970                 975
Asp Cys Glu Ile Ile Trp Thr Leu Gln Asp Thr Ser Gly Asn Lys Glu
            980                 985                 990
Lys Leu Ile Phe Arg Tyr Glu Glu Leu Ala Ser Ile Ser Asp Tyr Ile
            995                 1000                1005
Asn Lys Trp Ile Phe Val Thr Ile Thr Asn Asn Arg Leu Gly Asn
        1010                1015                1020
Ser Arg Ile Tyr Ile Asn Gly Asn Leu Ile Val Glu Lys Ser Ile
        1025                1030                1035
Ser Asn Leu Gly Asp Ile His Val Ser Asp Asn Ile Leu Phe Lys
        1040                1045                1050
Ile Val Gly Cys Asp Asp Glu Thr Tyr Val Gly Ile Arg Tyr Phe
        1055                1060                1065
Lys Val Phe Asn Thr Glu Leu Asp Lys Thr Glu Ile Glu Thr Leu
        1070                1075                1080
Tyr Ser Asn Glu Pro Asp Pro Ser Ile Leu Lys Asp Tyr Trp Gly
        1085                1090                1095
Asn Tyr Leu Leu Tyr Asn Lys Lys Tyr Tyr Leu Phe Asn Leu Leu
        1100                1105                1110
Arg Lys Asp Lys Tyr Ile Thr Arg Asn Ser Gly Ile Leu Asn Ile
        1115                1120                1125
Asn Gln Gln Arg Gly Val Thr Gly Gly Ile Ser Val Phe Leu Asn
```

```
                            1130                1135                1140

Tyr Lys Leu Tyr Glu Gly Val Glu Val Ile Ile Arg Lys Asn Ala
    1145                1150                1155

Pro Ile Asp Ile Ser Asn Thr Asp Asn Phe Val Arg Lys Asn Asp
    1160                1165                1170

Leu Ala Tyr Ile Asn Val Val Asp His Gly Val Glu Tyr Arg Leu
    1175                1180                1185

Tyr Ala Asp Ile Ser Ile Thr Lys Ser Glu Lys Ile Ile Lys Leu
    1190                1195                1200

Ile Arg Thr Ser Asn Pro Asn Asp Ser Leu Gly Gln Ile Ile Val
    1205                1210                1215

Met Asp Ser Ile Gly Asn Asn Cys Thr Met Asn Phe Gln Asn Asn
    1220                1225                1230

Asp Gly Ser Asn Ile Gly Leu Leu Gly Phe His Ser Asp Asp Leu
    1235                1240                1245

Val Ala Ser Ser Trp Tyr Tyr Asn His Ile Arg Arg Asn Thr Ser
    1250                1255                1260

Ser Asn Gly Cys Phe Trp Ser Phe Ile Ser Lys Glu His Gly Trp
    1265                1270                1275

Lys Glu
    1280

<210> SEQ ID NO 26
<211> LENGTH: 1278
<212> TYPE: PRT
<213> ORGANISM: Clostridium botulinum
<300> PUBLICATION INFORMATION:
<308> DATABASE ACCESSION NUMBER: AAA23210
<300> PUBLICATION INFORMATION:
<308> DATABASE ACCESSION NUMBER: CAA57358

<400> SEQUENCE: 26

Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
                20                  25                  30

Tyr Tyr Lys Ala Phe Glu Ile Met Arg Asn Val Trp Ile Ile Pro Glu
            35                  40                  45

Arg Asn Thr Ile Gly Thr Asp Pro Ser Asp Phe Asp Pro Pro Ala Ser
        50                  55                  60

Leu Glu Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Val Thr Arg Thr Thr Ser Val Asn Ile Lys Ser Ser Thr Asn
    130                 135                 140

Val Lys Ser Ser Ile Ile Leu Asn Leu Leu Val Leu Gly Ala Gly Pro
145                 150                 155                 160

Asp Ile Phe Glu Asn Ser Ser Tyr Pro Val Arg Lys Leu Met Asp Ser
                165                 170                 175

Gly Gly Val Tyr Asp Pro Ser Asn Asp Gly Phe Gly Ser Ile Asn Ile
            180                 185                 190
```

-continued

Val Thr Phe Ser Pro Glu Tyr Glu Tyr Thr Phe Asn Asp Ile Ser Gly
        195                 200                 205

Gly Tyr Asn Ser Ser Thr Glu Ser Phe Ile Ala Asp Pro Ala Ile Ser
        210                 215                 220

Leu Ala His Glu Leu Ile His Ala Leu His Gly Leu Tyr Gly Ala Arg
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
                260                 265                 270

Gln Asp Leu Asn Ile Ile Thr Ser Ala Met Lys Glu Lys Ile Tyr Asn
                275                 280                 285

Asn Leu Leu Ala Asn Tyr Glu Lys Ile Ala Thr Arg Leu Ser Arg Val
        290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
        340                 345                 350

Glu Ile Asp Leu Ala Asn Lys Phe Lys Val Lys Cys Arg Asn Thr Tyr
        355                 360                 365

Phe Ile Lys Tyr Gly Phe Leu Lys Val Pro Asn Leu Leu Asp Asp Asp
        370                 375                 380

Ile Tyr Thr Val Ser Glu Gly Phe Asn Ile Gly Asn Leu Ala Val Asn
385                 390                 395                 400

Asn Arg Gly Gln Asn Ile Lys Leu Asn Pro Lys Ile Ile Asp Ser Ile
                405                 410                 415

Pro Asp Lys Gly Leu Val Glu Lys Ile Val Lys Phe Cys Lys Ser Val
                420                 425                 430

Ile Pro Arg Lys Gly Thr Lys Ala Pro Pro Arg Leu Cys Ile Arg Val
        435                 440                 445

Asn Asn Arg Glu Leu Phe Val Ala Ser Glu Ser Tyr Asn Glu
        450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Glu Thr Ile Pro Gln Ile Ser Asn Gln Thr Leu Asn Thr Leu Val Gln
                500                 505                 510

Asp Asp Ser Tyr Val Pro Arg Tyr Asp Ser Asn Gly Thr Ser Glu Ile
                515                 520                 525

Glu Glu His Asn Val Val Asp Leu Asn Val Phe Phe Tyr Leu His Ala
530                 535                 540

Gln Lys Val Pro Glu Gly Glu Thr Asn Ile Ser Leu Thr Ser Ser Ile
545                 550                 555                 560

Asp Thr Ala Leu Ser Glu Glu Ser Gln Val Tyr Thr Phe Phe Ser Ser
                565                 570                 575

Glu Phe Ile Asn Thr Ile Asn Lys Pro Val His Ala Ala Leu Phe Ile
                580                 585                 590

Ser Trp Ile Asn Gln Val Ile Arg Asp Phe Thr Thr Glu Ala Thr Gln
                595                 600                 605

```
Lys Ser Thr Phe Asp Lys Ile Ala Asp Ile Ser Leu Val Val Pro Tyr
    610                 615                 620

Val Gly Leu Ala Leu Asn Ile Gly Asn Glu Val Gln Lys Glu Asn Phe
625                 630                 635                 640

Lys Glu Ala Phe Glu Leu Leu Gly Ala Gly Ile Leu Glu Phe Val
                645                 650                 655

Pro Glu Leu Leu Ile Pro Thr Ile Leu Val Phe Thr Ile Lys Ser Phe
                660                 665                 670

Ile Gly Ser Ser Glu Asn Lys Asn Lys Ile Ile Lys Ala Ile Asn Asn
        675                 680                 685

Ser Leu Met Glu Arg Glu Thr Lys Trp Lys Glu Ile Tyr Ser Trp Ile
    690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
                725                 730                 735

Val Ile Glu Tyr Lys Tyr Asn Asn Tyr Thr Ser Asp Glu Arg Asn Arg
                740                 745                 750

Leu Glu Ser Glu Tyr Asn Ile Asn Asn Ile Arg Glu Glu Leu Asn Lys
        755                 760                 765

Lys Val Ser Leu Ala Met Glu Asn Ile Glu Arg Phe Ile Thr Glu Ser
770                 775                 780

Ser Ile Phe Tyr Leu Met Lys Leu Ile Asn Glu Ala Lys Val Ser Lys
785                 790                 795                 800

Leu Arg Glu Tyr Asp Glu Gly Val Lys Glu Tyr Leu Leu Asp Tyr Ile
                805                 810                 815

Ser Glu His Arg Ser Ile Leu Gly Asn Ser Val Gln Glu Leu Asn Asp
                820                 825                 830

Leu Val Thr Ser Thr Leu Asn Asn Ser Ile Pro Phe Glu Leu Ser Ser
        835                 840                 845

Tyr Thr Asn Asp Lys Ile Leu Ile Leu Tyr Phe Asn Lys Leu Tyr Lys
    850                 855                 860

Lys Ile Lys Asp Asn Ser Ile Leu Asp Met Arg Tyr Glu Asn Asn Lys
865                 870                 875                 880

Phe Ile Asp Ile Ser Gly Tyr Gly Ser Asn Ile Ser Ile Asn Gly Asp
                885                 890                 895

Val Tyr Ile Tyr Ser Thr Asn Arg Asn Gln Phe Gly Ile Tyr Ser Ser
                900                 905                 910

Lys Pro Ser Glu Val Asn Ile Ala Gln Asn Asn Asp Ile Ile Tyr Asn
        915                 920                 925

Gly Arg Tyr Gln Asn Phe Ser Ile Ser Phe Trp Val Arg Ile Pro Lys
    930                 935                 940

Tyr Phe Asn Lys Val Asn Leu Asn Asn Glu Tyr Thr Ile Ile Asp Cys
945                 950                 955                 960

Ile Arg Asn Asn Asn Ser Gly Trp Lys Ile Ser Leu Asn Tyr Asn Lys
                965                 970                 975

Ile Ile Trp Thr Leu Gln Asp Thr Ala Gly Asn Asn Gln Lys Leu Val
                980                 985                 990

Phe Asn Tyr Thr Gln Met Ile Ser  Ile Ser Asp Tyr Ile  Asn Lys Trp
                995                 1000                1005

Ile Phe  Val Thr Ile Thr Asn  Asn Arg Leu Gly Asn  Ser Arg Ile
     1010                1015                1020

Tyr Ile  Asn Gly Asn Leu Ile  Asp Glu Lys Ser Ile  Ser Asn Leu
```

```
                  1025                1030                1035

Gly Asp Ile His Val Ser Asp Asn Ile Leu Phe Lys Ile Val Gly
        1040                1045                1050

Cys Asn Asp Thr Arg Tyr Val Gly Ile Arg Tyr Phe Lys Val Phe
        1055                1060                1065

Asp Thr Glu Leu Gly Lys Thr Glu Ile Glu Thr Leu Tyr Ser Asp
        1070                1075                1080

Glu Pro Asp Pro Ser Ile Leu Lys Asp Phe Trp Gly Asn Tyr Leu
        1085                1090                1095

Leu Tyr Asn Lys Arg Tyr Tyr Leu Leu Asn Leu Leu Arg Thr Asp
        1100                1105                1110

Lys Ser Ile Thr Gln Asn Ser Asn Phe Leu Asn Ile Asn Gln Gln
        1115                1120                1125

Arg Gly Val Tyr Gln Lys Pro Asn Ile Phe Ser Asn Thr Arg Leu
        1130                1135                1140

Tyr Thr Gly Val Glu Val Ile Ile Arg Lys Asn Gly Ser Thr Asp
        1145                1150                1155

Ile Ser Asn Thr Asp Asn Phe Val Arg Lys Asn Asp Leu Ala Tyr
        1160                1165                1170

Ile Asn Val Val Asp Arg Asp Val Glu Tyr Arg Leu Tyr Ala Asp
        1175                1180                1185

Ile Ser Ile Ala Lys Pro Glu Lys Ile Ile Lys Leu Ile Arg Thr
        1190                1195                1200

Ser Asn Ser Asn Asn Ser Leu Gly Gln Ile Ile Val Met Asp Ser
        1205                1210                1215

Ile Gly Asn Asn Cys Thr Met Asn Phe Gln Asn Asn Asn Gly Gly
        1220                1225                1230

Asn Ile Gly Leu Leu Gly Phe His Ser Asn Asn Leu Val Ala Ser
        1235                1240                1245

Ser Trp Tyr Tyr Asn Asn Ile Arg Lys Asn Thr Ser Ser Asn Gly
        1250                1255                1260

Cys Phe Trp Ser Phe Ile Ser Lys Glu His Gly Trp Gln Glu Asn
        1265                1270                1275

<210> SEQ ID NO 27
<211> LENGTH: 1268
<212> TYPE: PRT
<213> ORGANISM: Clostridium baratii
<300> PUBLICATION INFORMATION:
<308> DATABASE ACCESSION NUMBER: CAA48329
<300> PUBLICATION INFORMATION:
<308> DATABASE ACCESSION NUMBER: S33411

<400> SEQUENCE: 27

Met Pro Val Asn Ile Asn Asn Phe Asn Tyr Asn Asp Pro Ile Asn Asn
1               5                   10                  15

Thr Thr Ile Leu Tyr Met Lys Met Pro Tyr Tyr Glu Asp Ser Asn Lys
            20                  25                  30

Tyr Tyr Lys Ala Phe Glu Ile Met Asp Asn Val Trp Ile Ile Pro Glu
        35                  40                  45

Arg Asn Ile Ile Gly Lys Lys Pro Ser Asp Phe Tyr Pro Pro Ile Ser
    50                  55                  60

Leu Asp Ser Gly Ser Ser Ala Tyr Tyr Asp Pro Asn Tyr Leu Thr Thr
65                  70                  75                  80

Asp Ala Glu Lys Asp Arg Phe Leu Lys Thr Val Ile Lys Leu Phe Asn
                85                  90                  95
```

```
Arg Ile Asn Ser Asn Pro Ala Gly Gln Val Leu Leu Glu Glu Ile Lys
            100                 105                 110

Asn Gly Lys Pro Tyr Leu Gly Asn Asp His Thr Ala Val Asn Glu Phe
            115                 120                 125

Cys Ala Asn Asn Arg Ser Thr Ser Val Glu Ile Lys Glu Ser Asn Gly
        130                 135                 140

Thr Thr Asp Ser Met Leu Leu Asn Leu Val Ile Leu Gly Pro Gly Pro
145                 150                 155                 160

Asn Ile Leu Glu Cys Ser Thr Phe Pro Val Arg Ile Phe Pro Asn Asn
                165                 170                 175

Ile Ala Tyr Asp Pro Ser Glu Lys Gly Phe Gly Ser Ile Gln Leu Met
            180                 185                 190

Ser Phe Ser Thr Glu Tyr Glu Tyr Ala Phe Asn Asp Asn Thr Asp Leu
            195                 200                 205

Phe Ile Ala Asp Pro Ala Ile Ser Leu Ala His Glu Leu Ile His Val
            210                 215                 220

Leu His Gly Leu Tyr Gly Ala Lys Gly Val Thr Asn Lys Lys Val Ile
225                 230                 235                 240

Glu Val Asp Gln Gly Ala Leu Met Ala Ala Glu Lys Asp Ile Lys Ile
                245                 250                 255

Glu Glu Phe Ile Thr Phe Gly Gly Gln Asp Leu Asn Ile Ile Thr Asn
            260                 265                 270

Ser Thr Asn Gln Lys Ile Tyr Val Ile Leu Leu Ser Asn Tyr Thr Ala
            275                 280                 285

Ile Ala Ser Arg Leu Ser Gln Val Asn Arg Asn Asn Ser Ala Leu Asn
            290                 295                 300

Thr Thr Tyr Tyr Lys Asn Phe Phe Gln Trp Lys Tyr Gly Leu Asp Gln
305                 310                 315                 320

Asp Ser Asn Gly Asn Tyr Thr Val Asn Ile Ser Lys Phe Asn Ala Ile
                325                 330                 335

Tyr Lys Lys Leu Phe Ser Phe Thr Glu Cys Asp Leu Ala Gln Lys Phe
            340                 345                 350

Gln Val Lys Asn Arg Ser Asn Tyr Leu Phe His Phe Lys Pro Phe Arg
            355                 360                 365

Leu Leu Asp Leu Leu Asp Asp Asn Ile Tyr Ser Ile Ser Glu Gly Phe
370                 375                 380

Asn Ile Gly Ser Leu Arg Val Asn Asn Asn Gly Gln Asn Ile Asn Leu
385                 390                 395                 400

Asn Ser Arg Ile Val Gly Pro Ile Pro Asp Asn Gly Leu Val Glu Arg
                405                 410                 415

Phe Val Gly Leu Cys Lys Ser Ile Val Ser Lys Lys Gly Thr Lys Asn
            420                 425                 430

Ser Leu Cys Ile Lys Val Asn Asn Arg Asp Leu Phe Phe Val Ala Ser
        435                 440                 445

Glu Ser Ser Tyr Asn Glu Asn Gly Ile Asn Ser Pro Lys Glu Ile Asp
            450                 455                 460

Asp Thr Thr Ile Thr Asn Asn Tyr Lys Lys Asn Leu Asp Glu Val
465                 470                 475                 480

Ile Leu Asp Tyr Asn Ser Asp Ala Ile Pro Asn Leu Ser Ser Arg Leu
                485                 490                 495

Leu Asn Thr Thr Ala Gln Asn Asp Ser Tyr Val Pro Lys Tyr Asp Ser
            500                 505                 510
```

-continued

```
Asn Gly Thr Ser Glu Ile Lys Glu Tyr Thr Val Asp Lys Leu Asn Val
            515                 520                 525
Phe Phe Tyr Leu Tyr Ala Gln Lys Ala Pro Glu Gly Glu Ser Ala Ile
        530                 535                 540
Ser Leu Thr Ser Ser Val Asn Thr Ala Leu Leu Asp Ala Ser Lys Val
545                 550                 555                 560
Tyr Thr Phe Phe Ser Ser Asp Phe Ile Asn Thr Val Asn Lys Pro Val
                565                 570                 575
Gln Ala Ala Leu Phe Ile Ser Trp Ile Gln Val Ile Asn Asp Phe
                580                 585                 590
Thr Thr Glu Ala Thr Gln Lys Ser Thr Ile Asp Lys Ile Ala Asp Ile
            595                 600                 605
Ser Leu Ile Val Pro Tyr Val Gly Leu Ala Leu Asn Ile Gly Asn Glu
610                 615                 620
Val Gln Lys Gly Asn Phe Lys Glu Ala Ile Glu Leu Leu Gly Ala Gly
625                 630                 635                 640
Ile Leu Leu Glu Phe Val Pro Glu Leu Leu Ile Pro Thr Ile Leu Val
                645                 650                 655
Phe Thr Ile Lys Ser Phe Ile Asn Ser Asp Asp Ser Lys Asn Lys Ile
                660                 665                 670
Ile Lys Ala Ile Asn Asn Ala Leu Arg Glu Arg Glu Leu Lys Trp Lys
            675                 680                 685
Glu Val Tyr Ser Trp Ile Val Ser Asn Trp Leu Thr Arg Ile Asn Thr
            690                 695                 700
Gln Phe Asn Lys Arg Lys Glu Gln Met Tyr Gln Ala Leu Gln Asn Gln
705                 710                 715                 720
Val Asp Gly Ile Lys Lys Ile Glu Tyr Lys Tyr Asn Asn Tyr Thr
                725                 730                 735
Leu Asp Glu Lys Asn Arg Leu Arg Ala Glu Tyr Asn Ile Tyr Ser Ile
            740                 745                 750
Lys Glu Glu Leu Asn Lys Lys Val Ser Leu Ala Met Gln Asn Ile Asp
            755                 760                 765
Arg Phe Leu Thr Glu Ser Ser Ile Ser Tyr Leu Met Lys Leu Ile Asn
770                 775                 780
Glu Ala Lys Ile Asn Lys Leu Ser Glu Tyr Asp Lys Arg Val Asn Gln
785                 790                 795                 800
Tyr Leu Leu Asn Tyr Ile Leu Glu Asn Ser Ser Thr Leu Gly Thr Ser
                805                 810                 815
Ser Val Pro Glu Leu Asn Asn Leu Val Ser Asn Thr Leu Asn Asn Ser
                820                 825                 830
Ile Pro Phe Glu Leu Ser Glu Tyr Thr Asn Asp Lys Ile Leu Ile His
            835                 840                 845
Ile Leu Ile Arg Phe Tyr Lys Arg Ile Ile Asp Ser Ser Ile Leu Asn
850                 855                 860
Met Lys Tyr Glu Asn Asn Arg Phe Ile Asp Ser Ser Gly Tyr Gly Ser
865                 870                 875                 880
Asn Ile Ser Ile Asn Gly Asp Ile Tyr Ile Tyr Ser Thr Asn Arg Asn
                885                 890                 895
Gln Phe Gly Ile Tyr Ser Ser Arg Leu Ser Glu Val Asn Ile Thr Gln
                900                 905                 910
Asn Asn Thr Ile Ile Tyr Asn Ser Arg Tyr Gln Asn Phe Ser Val Ser
            915                 920                 925
Phe Trp Val Arg Ile Pro Lys Tyr Asn Asn Leu Lys Asn Leu Asn Asn
```

```
                930             935             940
Glu Tyr Thr Ile Ile Asn Cys Met Arg Asn Asn Ser Gly Trp Lys
945             950             955             960

Ile Ser Leu Asn Tyr Asn Asn Ile Ile Trp Thr Leu Gln Asp Thr Thr
            965             970             975

Gly Asn Asn Gln Lys Leu Val Phe Asn Tyr Thr Gln Met Ile Asp Ile
        980             985             990

Ser Asp Tyr Ile Asn Lys Trp Thr Phe Val Thr Ile Thr Asn Asn Arg
        995             1000            1005

Leu Gly His Ser Lys Leu Tyr Ile Asn Gly Asn Leu Thr Asp Gln
    1010            1015            1020

Lys Ser Ile Leu Asn Leu Gly Asn Ile His Val Asp Asp Asn Ile
    1025            1030            1035

Leu Phe Lys Ile Val Gly Cys Asn Asp Thr Arg Tyr Val Gly Ile
    1040            1045            1050

Arg Tyr Phe Lys Ile Phe Asn Met Glu Leu Asp Lys Thr Glu Ile
    1055            1060            1065

Glu Thr Leu Tyr His Ser Glu Pro Asp Ser Thr Ile Leu Lys Asp
    1070            1075            1080

Phe Trp Gly Asn Tyr Leu Leu Tyr Asn Lys Lys Tyr Tyr Leu Leu
    1085            1090            1095

Asn Leu Leu Lys Pro Asn Met Ser Val Thr Lys Asn Ser Asp Ile
    1100            1105            1110

Leu Asn Ile Asn Arg Gln Arg Gly Ile Tyr Ser Lys Thr Asn Ile
    1115            1120            1125

Phe Ser Asn Ala Arg Leu Tyr Thr Gly Val Glu Val Ile Ile Arg
    1130            1135            1140

Lys Val Gly Ser Thr Asp Thr Ser Asn Thr Asp Asn Phe Val Arg
    1145            1150            1155

Lys Asn Asp Thr Val Tyr Ile Asn Val Val Asp Gly Asn Ser Glu
    1160            1165            1170

Tyr Gln Leu Tyr Ala Asp Val Ser Thr Ser Ala Val Glu Lys Thr
    1175            1180            1185

Ile Lys Leu Arg Arg Ile Ser Asn Ser Asn Tyr Asn Ser Asn Gln
    1190            1195            1200

Met Ile Ile Met Asp Ser Ile Gly Asp Asn Cys Thr Met Asn Phe
    1205            1210            1215

Lys Thr Asn Asn Gly Asn Asp Ile Gly Leu Leu Gly Phe His Leu
    1220            1225            1230

Asn Asn Leu Val Ala Ser Ser Trp Tyr Tyr Lys Asn Ile Arg Asn
    1235            1240            1245

Asn Thr Arg Asn Asn Gly Cys Phe Trp Ser Phe Ile Ser Lys Glu
    1250            1255            1260

His Gly Trp Gln Glu
    1265

<210> SEQ ID NO 28
<211> LENGTH: 1297
<212> TYPE: PRT
<213> ORGANISM: Clostridium botulinum
<220> FEATURE:
<221> NAME/KEY: MOD_RES
<222> LOCATION: (7)..(7)
<223> OTHER INFORMATION: Any amino acid
<300> PUBLICATION INFORMATION:
<308> DATABASE ACCESSION NUMBER: CAA52275
```

<300> PUBLICATION INFORMATION:
<308> DATABASE ACCESSION NUMBER: Q60393

<400> SEQUENCE: 28

Met Pro Val Asn Ile Lys Xaa Phe Asn Tyr Asn Asp Pro Ile Asn Asn
1               5                   10                  15

Asp Asp Ile Ile Met Met Glu Pro Phe Asn Asp Pro Gly Pro Gly Thr
            20                  25                  30

Tyr Tyr Lys Ala Phe Arg Ile Ile Asp Arg Ile Trp Ile Val Pro Glu
        35                  40                  45

Arg Phe Thr Tyr Gly Phe Gln Pro Asp Gln Phe Asn Ala Ser Thr Gly
    50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
        275                 280                 285

Tyr Asn Lys Ala Leu Gln Asn Phe Gln Asp Ile Ala Asn Arg Leu Asn
290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr
        355                 360                 365

Arg Tyr Ser Tyr Phe Ser Glu Tyr Leu Pro Pro Ile Lys Thr Glu Lys
370                 375                 380

Leu Leu Asp Asn Thr Ile Tyr Thr Gln Asn Glu Gly Phe Asn Ile Ala
385                 390                 395                 400

```
Ser Lys Asn Leu Lys Thr Glu Phe Asn Gly Gln Asn Lys Ala Val Asn
                405                 410                 415

Lys Glu Ala Tyr Glu Ile Ser Leu Glu His Leu Val Ile Tyr Arg
            420                 425                 430

Ile Ala Met Cys Lys Pro Val Met Tyr Lys Asn Thr Gly Lys Ser Glu
                435                 440                 445

Gln Cys Ile Ile Val Asn Asn Glu Asp Leu Phe Phe Ile Ala Asn Lys
450                 455                 460

Asp Ser Phe Ser Lys Asp Leu Ala Lys Ala Glu Thr Ile Ala Tyr Asn
465                 470                 475                 480

Thr Gln Asn Asn Thr Ile Glu Asn Asn Phe Ser Ile Asp Gln Leu Ile
                485                 490                 495

Leu Asp Asn Asp Leu Ser Ser Gly Ile Asp Leu Pro Asn Glu Asn Thr
                500                 505                 510

Glu Pro Phe Thr Asn Phe Asp Asp Ile Asp Ile Pro Val Tyr Ile Lys
                515                 520                 525

Gln Ser Ala Leu Lys Lys Ile Phe Val Asp Gly Asp Ser Leu Phe Glu
530                 535                 540

Tyr Leu His Ala Gln Thr Phe Pro Ser Asn Ile Glu Asn Leu Gln Leu
545                 550                 555                 560

Thr Asn Ser Leu Asn Asp Ala Leu Arg Asn Asn Asn Lys Val Tyr Thr
                565                 570                 575

Phe Phe Ser Thr Asn Leu Val Glu Lys Ala Asn Thr Val Val Gly Ala
                580                 585                 590

Ser Leu Phe Val Asn Trp Val Lys Gly Val Ile Asp Asp Phe Thr Ser
                595                 600                 605

Glu Ser Thr Gln Lys Ser Thr Ile Asp Lys Val Ser Asp Val Ser Ile
610                 615                 620

Ile Ile Pro Tyr Ile Gly Pro Ala Leu Asn Val Gly Asn Glu Thr Ala
625                 630                 635                 640

Lys Glu Asn Phe Lys Asn Ala Phe Glu Ile Gly Gly Ala Ala Ile Leu
                645                 650                 655

Met Glu Phe Ile Pro Glu Leu Ile Val Pro Ile Val Gly Phe Phe Thr
                660                 665                 670

Leu Glu Ser Tyr Val Gly Asn Lys Gly His Ile Ile Met Thr Ile Ser
                675                 680                 685

Asn Ala Leu Lys Lys Arg Asp Gln Lys Trp Thr Asp Met Tyr Gly Leu
690                 695                 700

Ile Val Ser Gln Trp Leu Ser Thr Val Asn Thr Gln Phe Tyr Thr Ile
705                 710                 715                 720

Lys Glu Arg Met Tyr Asn Ala Leu Asn Asn Gln Ser Gln Ala Ile Glu
                725                 730                 735

Lys Ile Ile Glu Asp Gln Tyr Asn Arg Tyr Ser Glu Glu Asp Lys Met
                740                 745                 750

Asn Ile Asn Ile Asp Phe Asn Asp Ile Asp Phe Lys Leu Asn Gln Ser
                755                 760                 765

Ile Asn Leu Ala Ile Asn Asn Ile Asp Asp Phe Ile Asn Gln Cys Ser
                770                 775                 780

Ile Ser Tyr Leu Met Asn Arg Met Ile Pro Leu Ala Val Lys Lys Leu
785                 790                 795                 800

Lys Asp Phe Asp Asp Asn Leu Lys Arg Asp Leu Leu Glu Tyr Ile Asp
                805                 810                 815
```

-continued

```
Thr Asn Glu Leu Tyr Leu Leu Asp Glu Val Asn Ile Leu Lys Ser Lys
                820                 825                 830

Val Asn Arg His Leu Lys Asp Ser Ile Pro Phe Asp Leu Ser Leu Tyr
            835                 840                 845

Thr Lys Asp Thr Ile Leu Ile Gln Val Phe Asn Asn Tyr Ile Ser Asn
        850                 855                 860

Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
                885                 890                 895

Ile Phe Asn Asp Ile Gly Asn Gly Gln Phe Lys Leu Asn Asn Ser Glu
            900                 905                 910

Asn Ser Asn Ile Thr Ala His Gln Ser Lys Phe Val Val Tyr Asp Ser
        915                 920                 925

Met Phe Asp Asn Phe Ser Ile Asn Phe Trp Val Arg Thr Pro Lys Tyr
    930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
                965                 970                 975

Arg Ile Ile Trp Thr Leu Ile Asp Val Asn Ala Lys Ser Lys Ser Ile
            980                 985                 990

Phe Phe Glu Tyr Ser Ile Lys Asp  Asn Ile Ser Asp Tyr  Ile Asn Lys
        995                 1000                1005

Trp Phe Ser Ile Thr Ile Thr  Asn Asp Arg Leu Gly  Asn Ala Asn
    1010                1015                1020

Ile Tyr  Ile Asn Gly Ser Leu  Lys Lys Ser Glu Lys  Ile Leu Asn
    1025                1030                1035

Leu Asp  Arg Ile Asn Ser Ser  Asn Asp Ile Asp Phe  Lys Leu Ile
    1040                1045                1050

Asn Cys  Thr Asp Thr Thr Lys  Phe Val Trp Ile Lys  Asp Phe Asn
    1055                1060                1065

Ile Phe  Gly Arg Glu Leu Asn  Ala Thr Glu Val Ser  Ser Leu Tyr
    1070                1075                1080

Trp Ile  Gln Ser Ser Thr Asn  Thr Leu Lys Asp Phe  Trp Gly Asn
    1085                1090                1095

Pro Leu  Arg Tyr Asp Thr Gln  Tyr Tyr Leu Phe Asn  Gln Gly Met
    1100                1105                1110

Gln Asn  Ile Tyr Ile Lys Tyr  Phe Ser Lys Ala Ser  Met Gly Glu
    1115                1120                1125

Thr Ala  Pro Arg Thr Asn Phe  Asn Asn Ala Ala Ile  Asn Tyr Gln
    1130                1135                1140

Asn Leu  Tyr Leu Gly Leu Arg  Phe Ile Ile Lys Lys  Ala Ser Asn
    1145                1150                1155

Ser Arg  Asn Ile Asn Asn Asp  Asn Ile Val Arg Glu  Gly Asp Tyr
    1160                1165                1170

Ile Tyr  Leu Asn Ile Asp Asn  Ile Ser Asp Glu Ser  Tyr Arg Val
    1175                1180                1185

Tyr Val  Leu Val Asn Ser Lys  Glu Ile Gln Thr Gln  Leu Phe Leu
    1190                1195                1200

Ala Pro  Ile Asn Asp Asp Pro  Thr Phe Tyr Asp Val  Leu Gln Ile
    1205                1210                1215

Lys Lys  Tyr Tyr Glu Lys Thr  Thr Tyr Asn Cys Gln  Ile Leu Cys
```

```
                1220              1225              1230
Glu Lys Asp Thr Lys Thr Phe Gly Leu Phe Gly Ile Gly Lys Phe
    1235              1240              1245

Val Lys Asp Tyr Gly Tyr Val Trp Asp Thr Tyr Asp Asn Tyr Phe
    1250              1255              1260

Cys Ile Ser Gln Trp Tyr Leu Arg Arg Ile Ser Glu Asn Ile Asn
    1265              1270              1275

Lys Leu Arg Leu Gly Cys Asn Trp Gln Phe Ile Pro Val Asp Glu
    1280              1285              1290

Gly Trp Thr Glu
    1295

<210> SEQ ID NO 29
<211> LENGTH: 1297
<212> TYPE: PRT
<213> ORGANISM: Clostridium botulinum
<300> PUBLICATION INFORMATION:
<308> DATABASE ACCESSION NUMBER: S39791

<400> SEQUENCE: 29

Met Pro Val Asn Ile Lys Asn Phe Asn Tyr Asn Asp Pro Ile Asn Asn
1               5                   10                  15

Asp Asp Ile Ile Met Met Glu Pro Phe Asn Asp Pro Gly Pro Gly Thr
                20                  25                  30

Tyr Tyr Lys Ala Phe Arg Ile Asp Arg Ile Trp Ile Val Pro Glu
            35                  40                  45

Arg Phe Thr Tyr Gly Phe Gln Pro Asp Gln Phe Asn Ala Ser Thr Gly
    50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
    130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
    210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
```

-continued

```
                275                 280                 285
Tyr Asn Lys Ala Leu Gln Asn Phe Gln Asp Ile Ala Asn Arg Leu Asn
290                 295                 300
Ile Val Ser Ser Ala Gln Gly Ser Gly Ile Asp Ile Ser Leu Tyr Lys
305                 310                 315                 320
Gln Ile Tyr Lys Asn Lys Tyr Asp Phe Val Glu Asp Pro Asn Gly Lys
                325                 330                 335
Tyr Ser Val Asp Lys Asp Lys Phe Asp Lys Leu Tyr Lys Ala Leu Met
                340                 345                 350
Phe Gly Phe Thr Glu Thr Asn Leu Ala Gly Glu Tyr Gly Ile Lys Thr
                355                 360                 365
Arg Tyr Ser Tyr Phe Ser Glu Tyr Leu Pro Pro Ile Lys Thr Glu Lys
370                 375                 380
Leu Leu Asp Asn Thr Ile Tyr Thr Gln Asn Glu Gly Phe Asn Ile Ala
385                 390                 395                 400
Ser Lys Asn Leu Lys Thr Glu Phe Asn Gly Gln Asn Lys Ala Val Asn
                405                 410                 415
Lys Glu Ala Tyr Glu Glu Ile Ser Leu Glu His Leu Val Ile Tyr Arg
                420                 425                 430
Ile Ala Met Cys Lys Pro Val Met Tyr Lys Asn Thr Gly Lys Ser Glu
                435                 440                 445
Gln Cys Ile Ile Val Asn Asn Glu Asp Leu Phe Phe Ile Ala Asn Lys
                450                 455                 460
Asp Ser Phe Ser Lys Asp Leu Ala Lys Ala Glu Thr Ile Ala Tyr Asn
465                 470                 475                 480
Thr Gln Asn Asn Thr Ile Glu Asn Asn Phe Ser Ile Asp Gln Leu Ile
                485                 490                 495
Leu Asp Asn Asp Leu Ser Ser Gly Ile Asp Leu Pro Asn Glu Asn Thr
                500                 505                 510
Glu Pro Phe Thr Asn Phe Asp Asp Ile Asp Ile Pro Val Tyr Ile Lys
                515                 520                 525
Gln Ser Ala Leu Lys Lys Ile Phe Val Asp Gly Asp Ser Leu Phe Glu
                530                 535                 540
Tyr Leu His Ala Gln Thr Phe Pro Ser Asn Ile Glu Asn Leu Gln Leu
545                 550                 555                 560
Thr Asn Ser Leu Asn Asp Ala Leu Arg Asn Asn Asn Lys Val Tyr Thr
                565                 570                 575
Phe Phe Ser Thr Asn Leu Val Glu Lys Ala Asn Thr Val Val Gly Ala
                580                 585                 590
Ser Leu Phe Val Asn Trp Val Lys Gly Val Ile Asp Asp Phe Thr Ser
                595                 600                 605
Glu Ser Thr Gln Lys Ser Thr Ile Asp Lys Val Ser Asp Val Ser Ile
                610                 615                 620
Ile Ile Pro Tyr Ile Gly Pro Ala Leu Asn Val Gly Asn Glu Thr Ala
625                 630                 635                 640
Lys Glu Asn Phe Lys Asn Ala Phe Glu Ile Gly Gly Ala Ala Ile Leu
                645                 650                 655
Met Glu Phe Ile Pro Glu Leu Ile Val Pro Ile Val Gly Phe Phe Thr
                660                 665                 670
Leu Glu Ser Tyr Val Gly Asn Lys Gly His Ile Ile Met Thr Ile Ser
                675                 680                 685
Asn Ala Leu Lys Lys Arg Asp Gln Lys Trp Thr Asp Met Tyr Gly Leu
690                 695                 700
```

```
Ile Val Ser Gln Trp Leu Ser Thr Val Asn Thr Gln Phe Tyr Thr Ile
705                 710                 715                 720

Lys Glu Arg Met Tyr Asn Ala Leu Asn Asn Gln Ser Gln Ala Ile Glu
            725                 730                 735

Lys Ile Ile Glu Asp Gln Tyr Asn Arg Tyr Ser Glu Gly Asp Lys Met
            740                 745                 750

Asn Ile Asn Ile Asp Phe Asn Asp Ile Asp Phe Lys Leu Asn Gln Ser
            755                 760                 765

Ile Asn Leu Ala Ile Asn Asn Ile Asp Asp Phe Ile Asn Gln Cys Ser
770                 775                 780

Ile Ser Tyr Leu Met Asn Arg Met Ile Pro Leu Ala Val Lys Lys Leu
785                 790                 795                 800

Lys Asp Phe Asp Asp Asn Leu Lys Arg Asp Leu Leu Glu Tyr Ile Asp
            805                 810                 815

Thr Asn Glu Leu Tyr Leu Leu Asp Glu Val Asn Ile Leu Lys Ser Lys
            820                 825                 830

Val Asn Arg His Leu Lys Asp Ser Ile Pro Phe Asp Leu Ser Leu Tyr
            835                 840                 845

Thr Lys Asp Thr Ile Leu Ile Gln Val Phe Asn Asn Tyr Ile Ser Asn
850                 855                 860

Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
            885                 890                 895

Ile Phe Asn Asp Ile Gly Asn Gly Gln Phe Lys Leu Asn Asn Ser Glu
            900                 905                 910

Asn Ser Asn Ile Thr Ala His Gln Ser Lys Phe Val Val Tyr Asp Ser
            915                 920                 925

Met Phe Asp Asn Phe Ser Ile Asn Phe Trp Val Arg Thr Pro Lys Tyr
930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
            965                 970                 975

Arg Ile Ile Trp Thr Leu Ile Asp Val Asn Ala Lys Ser Lys Ser Ile
            980                 985                 990

Phe Phe Glu Tyr Ser Ile Lys Asp Asn Ile Ser Asp Tyr Ile Asn Lys
            995                 1000                1005

Trp Phe Ser Ile Thr Ile Thr Asn Asp Arg Leu Gly Asn Ala Asn
            1010                1015                1020

Ile Tyr Ile Asn Gly Ser Leu Lys Lys Ser Glu Lys Ile Leu Asn
            1025                1030                1035

Leu Asp Arg Ile Asn Ser Ser Asn Asp Ile Asp Phe Lys Leu Ile
            1040                1045                1050

Asn Cys Thr Asp Thr Thr Lys Phe Val Trp Ile Lys Asp Phe Asn
            1055                1060                1065

Ile Phe Gly Arg Glu Leu Asn Ala Thr Glu Val Ser Ser Leu Tyr
            1070                1075                1080

Trp Ile Gln Ser Ser Thr Asn Thr Leu Lys Asp Phe Trp Gly Asn
            1085                1090                1095

Pro Leu Arg Tyr Asp Thr Gln Tyr Tyr Leu Phe Asn Gln Gly Met
            1100                1105                1110
```

-continued

```
Gln Asn Ile Tyr Ile Lys Tyr Phe Ser Lys Ala Ser Met Gly Glu
1115                1120                1125

Thr Ala Pro Arg Thr Asn Phe Asn Asn Ala Ala Ile Asn Tyr Gln
1130                1135                1140

Asn Leu Tyr Leu Gly Leu Arg Phe Ile Ile Lys Lys Ala Ser Asn
1145                1150                1155

Ser Arg Asn Ile Asn Asn Asp Asn Ile Val Arg Glu Gly Asp Tyr
1160                1165                1170

Ile Tyr Leu Asn Ile Asp Asn Ile Ser Asp Glu Ser Tyr Arg Val
1175                1180                1185

Tyr Val Leu Val Asn Ser Lys Glu Ile Gln Thr Gln Leu Phe Leu
1190                1195                1200

Ala Pro Ile Asn Asp Asp Pro Thr Phe Tyr Asp Val Leu Gln Ile
1205                1210                1215

Lys Lys Tyr Tyr Glu Lys Thr Thr Tyr Asn Cys Gln Ile Leu Cys
1220                1225                1230

Glu Lys Asp Thr Lys Thr Phe Gly Leu Phe Gly Ile Gly Lys Phe
1235                1240                1245

Val Lys Asp Tyr Gly Tyr Val Trp Asp Thr Tyr Asp Asn Tyr Phe
1250                1255                1260

Cys Ile Ser Gln Trp Tyr Leu Arg Arg Ile Ser Glu Asn Ile Asn
1265                1270                1275

Lys Leu Arg Leu Gly Cys Asn Trp Gln Phe Ile Pro Val Asp Glu
1280                1285                1290

Gly Trp Thr Glu
1295
```